US009137973B2

(12) United States Patent
Boyall et al.

(10) Patent No.: US 9,137,973 B2
(45) Date of Patent: Sep. 22, 2015

(54) PYRAZOLOPYRIDINE KINASE INHIBITORS

(75) Inventors: Dean Boyall, Faringdon (GB); Guy Brenchley, West Hanney (GB); Damien Fraysse, Abingdon (GB); Juan-Miguel Jimenez, Abingdon (GB); Luca Settimo, Oxford (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 217 days.

(21) Appl. No.: 13/308,609

(22) Filed: Dec. 1, 2011

(65) Prior Publication Data
US 2012/0184524 A1 Jul. 19, 2012

Related U.S. Application Data

(63) Continuation of application No. PCT/US2009/051413, filed on Jul. 22, 2009.

(60) Provisional application No. 61/082,929, filed on Jul. 23, 2008, provisional application No. 61/140,101, filed on Dec. 23, 2008, provisional application No. 61/163,176, filed on Mar. 25, 2009.

(51) Int. Cl.
| | |
|---|---|
| *A01N 43/00* | (2006.01) |
| *A61K 31/00* | (2006.01) |
| *A01N 43/62* | (2006.01) |
| *A61K 31/55* | (2006.01) |
| *A61K 31/50* | (2006.01) |
| *A61K 31/497* | (2006.01) |
| *A61K 31/44* | (2006.01) |
| *C07D 241/02* | (2006.01) |
| *C07D 401/00* | (2006.01) |
| *C07D 403/00* | (2006.01) |
| *C07D 513/02* | (2006.01) |
| *C07D 243/08* | (2006.01) |
| *A01K 39/01* | (2006.01) |

(52) U.S. Cl.
CPC ..................................... *A01K 39/01* (2013.01)

(58) Field of Classification Search
USPC .......... 514/303, 210.21, 218, 252.11, 253.04; 540/575; 544/357, 362, 405; 546/119
See application file for complete search history.

(56) References Cited

U.S. PATENT DOCUMENTS

| | | | |
|---|---|---|---|
| 3,853,898 A | 12/1974 | Hardtmann et al. |
| 4,783,472 A | 11/1988 | Fabre et al. |
| 5,001,137 A | 3/1991 | Oe et al. |
| 5,100,768 A | 3/1992 | Niki et al. |
| 5,202,224 A | 4/1993 | Yamakawa et al. |
| 5,308,854 A | 5/1994 | Hoffman et al. |
| 5,385,880 A | 1/1995 | Miyazaki et al. |
| 5,439,916 A | 8/1995 | Ganguly et al. |
| 5,476,750 A | 12/1995 | Chu et al. |
| 5,643,744 A | 7/1997 | Nitta et al. |
| 5,646,330 A | 7/1997 | Shieh et al. |
| 5,760,032 A | 6/1998 | Kitajima et al. |
| 5,817,670 A | 10/1998 | Takayama et al. |
| 5,885,935 A | 3/1999 | Gates et al. |
| 6,136,810 A | 10/2000 | Takayama et al. |
| 6,194,581 B1 | 2/2001 | Cosford et al. |
| 6,225,329 B1 | 5/2001 | Richter et al. |
| 6,303,655 B1 | 10/2001 | Takehana et al. |
| 6,436,961 B1 | 8/2002 | Watson et al. |
| 6,452,008 B2 | 9/2002 | Muraoka et al. |
| 6,638,935 B2 | 10/2003 | Emig et al. |
| 6,673,789 B2 | 1/2004 | Dickinson et al. |
| 6,770,662 B2 | 8/2004 | Nishide et al. |
| 6,831,175 B2 | 12/2004 | Li et al. |
| 8,188,071 B2 | 5/2012 | Maltais et al. |
| 2002/0115642 A1 | 8/2002 | Chan et al. |
| 2003/0187026 A1 | 10/2003 | Li et al. |
| 2004/0058903 A1 | 3/2004 | Takasugi et al. |
| 2004/0142982 A1 | 7/2004 | Jimenez Mayorga et al. |
| 2004/0176355 A1 | 9/2004 | Sasikumar et al. |
| 2004/0176395 A1 | 9/2004 | Flynn et al. |
| 2005/0004125 A1 | 1/2005 | Freyne et al. |
| 2005/0049274 A1 | 3/2005 | Wall et al. |
| 2005/0203067 A1 | 9/2005 | Hresko et al. |
| 2005/0277640 A1 | 12/2005 | Dixon et al. |
| 2005/0288286 A1 | 12/2005 | Flynn et al. |
| 2006/0020039 A1 | 1/2006 | Zhu et al. |
| 2006/0030583 A1 | 2/2006 | Arnold et al. |
| 2006/0122185 A1* | 6/2006 | Green et al. .................. 514/248 |

(Continued)

FOREIGN PATENT DOCUMENTS

| | | |
|---|---|---|
| EP | 0359547 | 3/1990 |
| GB | 2208862 | 4/1989 |
| WO | 9857957 | 12/1998 |
| WO | 02072571 | 9/2002 |
| WO | 03099773 | 12/2003 |
| WO | 2004014368 | 2/2004 |
| WO | 2005000813 | 1/2005 |

(Continued)

OTHER PUBLICATIONS

Martinez-Viturro, et al., "Synthesis of aza analogues of the anticancer agent batracylin", www.sciencedirect.com , Tetrahedron letters 48 (2007) 4707-4710.
Geng, et al., "Potent and selective inhibitors of *Helicobacter pylori* glutamate racemase (Murl): Pyridodiazepine amines", Bioorganic & Medicinal Chemistry Letters (2009) vol. 19, Issue 3, p. 930.
Gungor et al., "Metallation Regioselective en Serie Pyridinique: Synthese Originale D'Amino-2 Aroyl-3 Pyridines", J Organomet Chem 215(): 139-150 1981.
International Search Report Received in the corresponding PCT Application No. PCT/US2008/051413.

*Primary Examiner* — Paul Zarek
*Assistant Examiner* — George W Kosturko
(74) *Attorney, Agent, or Firm* — Min Lin

(57) ABSTRACT

The present invention relates to compounds useful as inhibitors of protein kinase. The invention also provides pharmaceutically acceptable compositions comprising said compounds and methods of using the compositions in the treatment of various disease, conditions, or disorders. The invention also provides processes for preparing compounds of the inventions.

20 Claims, No Drawings

(56) References Cited

U.S. PATENT DOCUMENTS

| | | |
|---|---|---|
| 2006/0167251 A1 | 7/2006 | Fleming et al. |
| 2006/0205739 A1 | 9/2006 | Eberle et al. |
| 2006/0217387 A1 | 9/2006 | McArthur et al. |
| 2006/0252764 A1 | 11/2006 | Guillemont et al. |
| 2006/0276510 A1 | 12/2006 | Abu-Shakra et al. |
| 2007/0037794 A1 | 2/2007 | Ungashe et al. |
| 2007/0037811 A1 | 2/2007 | Lewi et al. |
| 2007/0043068 A1 | 2/2007 | Arnold et al. |
| 2007/0078140 A1 | 4/2007 | Borzilleri et al. |
| 2007/0275954 A1 | 11/2007 | Basarab et al. |
| 2007/0287711 A1 * | 12/2007 | Arnold et al. ........... 514/249 |
| 2008/0039477 A1 | 2/2008 | Freyne et al. |
| 2009/0030017 A1 | 1/2009 | Hanada et al. |
| 2009/0143352 A1 | 6/2009 | Arnold et al. |
| 2009/0227799 A1 | 9/2009 | Nakamoto et al. |
| 2011/0118248 A1 | 5/2011 | Ungashe et al. |

FOREIGN PATENT DOCUMENTS

| | | |
|---|---|---|
| WO | 2005028479 | 3/2005 |
| WO | 2005103050 | 11/2005 |
| WO | 2008124849 | 10/2008 |

* cited by examiner

PYRAZOLOPYRIDINE KINASE INHIBITORS

CROSS REFERENCE TO RELATED APPLICATION

This application is a continuation application of International Patent Application No. PCT/US2009/051413, filed on Jul. 22, 2009, which in turn claims the benefit under 35 U.S.C. §119, of U.S. provisional application Ser. Nos. 61/082,929, filed Jul. 23, 2008, 61/140,101, filed Dec. 23, 2008, and 61/163,176, filed Mar. 25, 2009, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Mar. 6, 2012 is named VPI08130.txt and is 1,021 bytes in size.

BACKGROUND OF THE INVENTION

Protein kinases constitute a large family of structurally related enzymes that are responsible for the control of a variety of signal transduction processes within the cell (see Hardie, G. and Hanks, S. *The Protein Kinase Facts Book, I and II*, Academic Press, San Diego, Calif.: 1995).

In general, protein kinases mediate intracellular signaling by affecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g. shock, heat shock, ultraviolet radiation, bacterial endotoxin, and $H_2O_2$), cytokines (e.g. interleukin-1 (IL-1) and tumor necrosis factor alpha (TNF-a), and growth factors (e.g. granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Kinases may be categorized into families by the substrates they phosphorylate (e.g. protein-tyrosine, protein-serine/threonine, lipids etc). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al, *Cell* 1992, 70, 419-429; Kunz et al, *Cell* 1993, 73, 585-596; Garcia-Bustos et al, *EMBO J* 1994, 13, 2352-2361).

A serine/threonine kinase, protein kinase C-theta (PKC-theta), is a member of the novel, calcium independent PKC subfamily that is, selectively expressed in T cells and skeletal muscle. Several lines of evidence indicate that PKC-theta has an essential role in T cell activation. Upon antigen stimulation of T cells, PKC-theta, but not other PKC isoforms, rapidly translocates from the cytoplasm to the site of cell contact between the T cell and antigen-presenting cell (APC), where it localizes with the T cell receptor (TCR) in a region termed the central supramolecular activation cluster (cSMAC) (Monks et al., 1997, Nature, 385: 83-86; Monks et al., 1998, Nature, 395: 82-86).

It has been reported that PKC-theta selectively activates the transcription factors AP-1 and NF-κB and integrates TCR and CD28 co-stimulatory signals leading to the activation of the CD28 response element (CD28RE) in the IL-2 promotor (Baier-Bitterlich et al., 1996, Mol. Cell. Biol., 16: 1842-1850; Coudronniere et al., 2000, PNAS, 97: 3394-3399). The specific role for PKC-theta in CD3/CD28 co-stimulation of T cells is highlighted in a study where expression of a kinase-dead PKC-theta mutant, or anti-sense PKC-theta dose-dependently inhibited CD3/CD28 co-stimulated NF-κB activation, but not TNF-alpha-stimulated NF-κB activation. This was not seen with other PKC isoforms (Lin et al., 2000, Mol. Cell. Biol., 20: 2933-2940). Recruitment of PKC-theta to the SMAC is reported to be mediated by its N-terminal regulatory domain and is necessary for T cell activation, as an over-expressed PKC-theta catalytic fragment did not translocate and was unable to activate NF-κB, whereas a PKC-theta catalytic domain-Lck membrane-binding domain chimera was able to reconstitute signaling (Bi et al., 2001, Nat. Immunol., 2:556-563).

Translocation of PKC-theta to the SMAC appears to be mediated by a largely PLC-gamma/DAG-independent mechanism, involving Vav and PI3-kinase (Villalba et al., 2002, JCB 157: 253-263), whilst activation of PKC-theta requires input from several signaling components including Lck, ZAP-70, SLP-76, PLC-gamma, Vav and PI3-kinase (Liu et al., 2000, JBC, 275: 3606-3609; Herndon et al., 2001, J. Immunol., 166: 5654-5664; Dienz et al., 2002, J. Immunol., 169: 365-372; Bauer et al., 2001 JBC., 276: 31627-31634). These biochemical studies in human T cells have gained credence from studies in PKC-theta knockout mice, which have confirmed a crucial role for this enzyme in T cell function. PKC-theta-/- mice are healthy and fertile, have a normally developed immune system, but exhibit profound defects in mature T cell activation (Sun et al., 200, Nature, 404:402-407). Proliferative responses to TCR and TCR/CD28 co-stimulation were inhibited (>90%) as were in vivo responses to antigen. In agreement with studies on human T cells, activation of the transcription factors AP-1 and NF-κB was abrogated, resulting in a severe deficit in IL-2 production and IL-2 R upregulation (Baier-Bitterlich et al., 1996, MBC, 16, 1842; Lin et al., 2000, MCB, 20, 2933; Courdonniere, 2000, 97, 3394). More recently, studies in PKC-theta-deficient mice have indicated a role for PKC-theta in the development of mouse models of autoimmune diseases, including multiple sclerosis (MS), rheumatoid arthritis (RA) and irritable bowel disease (IBD) (Salek-Ardakani et al., 2006; Tan et al., 2006; Healy et al., 2006; Anderson et al., 2006). In these models, PKC-theta-deficient mice exhibited a marked reduction in disease severity that was associated with a profound defect in the development and effector function of autoreactive T cells.

In addition to its role in T cell activation, PKC-theta is reported to mediate the phorbol ester-triggered survival signal that protects T cells from Fas- and UV-induced apoptosis (Villalba et al., 2001, J. Immunol. 166: 5955-5963; Berttolotto et al., 2000, 275: 37246-37250). This pro-survival role is of interest because the human PKC-theta gene has been mapped to chromosome 10 (10p15), a region associated with mutations leading to T cell leukaemias and lymphomas (Erdel et al., 1995, Genomics 25: 295-297; Verma et al., 1987, J. Cancer Res. Clin. Oncol., 113: 192-196).

In vivo, the role for PKC-theta in immune responses to infection is dependent on the type of pathogen encountered. PKC-theta deficient mice elicit normal Th1 and cytotoxic T cell-mediated responses to several viral infections and the protozoan parasite, *Leishmania major* and effectively clear these infections (Marsland et al., 2004; Berg-Brown et al., 2004; Marsland et al., 2005; Giannoni et al., 2005). However, PKC-theta deficient mice are unable to wage normal Th2 T cell responses against the parasite *Nippostrongylus brasiliensis* and certain allergens (Marsland, et al., 2004; Salek-Ardakani et al., 2004) and are unable to clear *Listeria monocytogenes* infection (Sakowicz-Burkiewicz et al., 2008). Clearly in some circumstances, the requirement for PKC-theta in T cell activation can be bypassed and this is likely to involve the provision of additional signals to T cells, either from cells of the innate immune system, or directly from the pathogen in the form of pathogen associated molecular patterns (PAMPs) (Marsland et al., 2007).

More recently, studies in PKC-theta-deficient mice have indicated a role for PKC-theta in the development of mouse models of autoimmune diseases, including multiple sclerosis, rheumatoid arthritis and inflammatory bowel disease. In all cases where examined, PKC-theta-deficient mice exhibited a marked reduction in disease severity that was associated with a profound defect in the development of a newly discovered class of T cells, Th17 cells (Salek-Ardakani et al., 2006; Tan et al., 2006; Healy et al., 2006; Anderson et al., 2006; Nagahama et al., 2008). PKC-theta therefore appears to be essential for the development of pathogenic autoreactive Th17 cells in the context of autoimmunity. These observations support the notion that targeting PKC-theta will provide a way to target autoimmune T cell responses, leaving many T cell responses (e.g., to viral infections) intact.

In addition to its role in T cell activation, PKC-theta mediates the phorbol ester-triggered survival signal that protects T cells from Fas- and UV-induced apoptosis (Villalba et al., 2001, J. Immunol. 166: 5955-5963; Berttolotto et al., 2000, 275: 37246-37250). This pro-survival role is of interest because the human PKC-theta gene has been mapped to chromosome 10 (10p15), a region associated with mutations leading to T cell leukaemias and lymphomas (Erdel et al., 1995, Genomics 25: 295-297; Verma et al., 1987, J. Cancer Res. Clin. Oncol., 113: 192-196).

Together, these data indicate that PKC-theta is an attractive target for therapeutic intervention in inflammatory disorders, immune disorders, lymphomas and T cell leukaemias.

Accordingly, there is a great need to develop compounds useful as inhibitors of protein kinases. In particular, it would be desirable to develop compounds that are useful as inhibitors of PKC-theta, particularly given the inadequate treatments currently available for the majority of the disorders' implicated in their activation.

SUMMARY OF THE INVENTION

This invention provides, in general, compounds that are useful as kinase inhibitors.

In one embodiment the compounds of the present invention are represented by structural formula I:

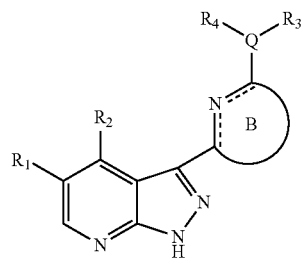

or a pharmaceutically acceptable salt thereof.

$R_1$ is —H, halogen, —OR', —N(R')$_2$, —C(O)OR', —C(O)N(R')$_2$, —NR'C(O)R', —CN, —NO$_2$, C1-C10 aliphatic optionally and independently substituted with one or more $J_a$, or C3-C8 cycloaliphatic optionally and independently substituted with one or more $J_b$.

$R_2$ is —H, halogen, —OR', —N(R')$_2$, —C(O)OR', —C(O)N(R')$_2$, —NR'C(O)R', —NR'C(O)OR', —CN, —NO$_2$, C1-C10 aliphatic optionally and independently substituted with one or more $J_a$, or C3-C8 cycloaliphatic optionally and independently substituted with one or more $J_b$.

Q is —N—, —O—, or —S—.

Ring B is a 6-membered monocyclic heteroaromatic ring optionally fused to an aromatic or non-aromatic ring; and ring B is optionally substituted with one Y and independently further optionally and independently substituted with one or more $J_c$.

Y is —Y1-Q1.

Y1 is absent, or C1-10 aliphatic, wherein up to three methylene units of Y1 are optionally and independently replaced with G' wherein G' is —O—, —C(O)—, —N(R')—, or —S(O)$_p$—; and Y1 is optionally and independently substituted with one or more $J_d$.

Q1 is absent, or a C3-8 membered saturated, partially unsaturated, or fully unsaturated monocyclic ring having 0-3 heteroatoms independently selected from nitrogen, oxygen, and sulfur; and Q1 is optionally and independently substituted with one or more $J_b$; wherein when B is substituted with Y then Y1 and Q1 are not both absent.

$R_3$ is absent, —H, or C1-C6 alkyl optionally and independently substituted with one or more $J_a$.

$R_4$ is a C1-10 aliphatic, wherein up to three methylene units of $R_4$ are optionally and independently replaced by G' wherein G' is —O—, —C(O)—, —N(R')—, or —S(O)$_p$—; and $R_4$ is optionally and independently substituted with one ring C and independently further optionally and independently substituted with one or more $J_a$; or $R_4$ is ring C.

Ring C is a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur optionally and independently substituted with one Z or independently further optionally and independently substituted with one or more $J_b$.

Z is —Y2-Q2.

Y2 is absent, or C1-10 aliphatic, wherein up to three methylene units of Y2 are optionally and independently replaced with G' wherein G' is —O—, —C(O)—, —N(R')—, or —S(O)$_p$—; and Y2 is optionally and independently substituted with one or more $J_d$.

Q2 is absent, C3-8 membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur; and Q2 is optionally and independently substituted with one or more $J_e$; wherein when C is substituted with Z then Y2 and Q2 are not both absent.

Each R' is independently —H, or C1-C6 alkyl optionally and independently substituted with one or more $J_a$.

Each $J_a$ is independently halogen, —OR, —N(R)$_2$, —C(O)R, —C(O)OR, —C(O)N(R)$_2$, —NRC(O)R, —NRC(O)OR, —CN, —NO$_2$, or oxo.

Each $J_b$ is independently halogen, —OR, —N(R)$_2$, —C(O)R, —C(O)OR, —C(O)N(R)$_2$, —NRC(O)R, —NRC(O)OR, —CN, —NO$_2$, oxo, or C1-C6 alkyl optionally and independently substituted with one or more J$_a$.

Each J$_d$ is independently halogen, —OR', —N(R')$_2$, —C(O)R, —C(O)OR', —C(O)N(R')$_2$, —NR'C(O)R', —NR'C(O)OR', —CN, —NO$_2$, or C1-C10 aliphatic optionally and independently substituted with one or more J$_a$, or C3-C8 cycloaliphatic optionally and independently substituted with one or more J$_b$.

Each J$_d$ is independently halogen, —OH, —NH$_2$, —C(O)H, —C(O)OH, —C(O)NH$_2$, —NHC(O)H, —NHC(O)OH, —CN, or —NO$_2$.

Each J$_e$ is independently halogen, —OH, —NH$_2$, —C(O)H, —C(O)OH, —C(O)NH$_2$, —NHC(O)H, —NHC(O)OH, —CN, —NO$_2$, oxo, C1-10 aliphatic, wherein up to three methylene units are optionally and independently replaced with G' wherein G' is —O—, —C(O)—, —N(R')—, or —S(O)$_p$— and the aliphatic group is optionally and independently substituted with one or more J$_d$, or J$_e$ is C3-8 cycloaliphatic optionally and independently substituted with one or more J$_b$.

Each R is independently —H or C1-C6 alkyl.

Each p is independently 0, 1, or 2.

In one embodiment, the present invention is a method of treating or preventing protein kinase-mediated condition in a subject, comprising administering to the subject an effective amount of a compound, a pharmaceutically acceptable salt thereof, or composition of the present invention.

In one embodiment the present invention is the manufacture of a compound, a pharmaceutically acceptable salt thereof, or composition of the present invention for use in treating or preventing a protein kinase-mediated condition in a subject.

In another embodiment, the compounds, pharmaceutically acceptable salts thereof, and compositions of the present invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

This invention relates to compounds, pharmaceutically acceptable salts thereof, and compositions (such as, pharmaceutical compositions) useful as protein kinase inhibitors.

In one embodiment, the compounds, pharmaceutically acceptable salts thereof, and compositions of the present invention are effective as inhibitors of PKCtheta.

Compounds of this invention include those described generally herein, and are further illustrated by the classes, subclasses, and species disclosed herein. As used herein, the definitions defined herein shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

In one embodiment the compounds of the present invention are represented by structural formula I:

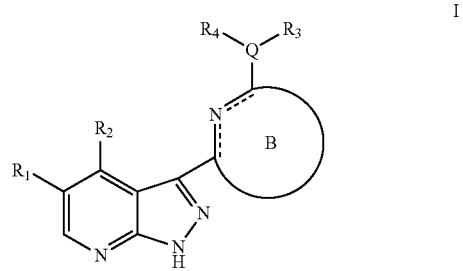

or a pharmaceutically acceptable salt thereof.

R$_1$ is —H, halogen, —OR', —N(R')$_2$, —C(O)OR', —C(O)N(R')$_2$, —NR'C(O)R', —NR'C(O)OR', —CN, —NO$_2$, C1-C10 aliphatic optionally and independently substituted with one or more J$_a$, or C3-C8 cycloaliphatic optionally and independently substituted with one or more J$_b$.

R$_2$ is —H, halogen, —OR', —N(R')$_2$, —C(O)OR', —C(O)N(R')$_2$, —NR'C(O)R', —NR'C(O)OR', —CN, —NO$_2$, C1-C10 aliphatic optionally and independently substituted with one or more J$_a$, or C3-C8 cycloaliphatic optionally and independently substituted with one or more J$_b$.

Q is —N—, —O—, or —S—.

Ring B is a 6-membered monocyclic heteroaromatic ring optionally fused to an aromatic or non-aromatic ring; and ring B is optionally substituted with one Y and independently further optionally and independently substituted with one or more J$_c$.

Y is —Y1-Q1.

Y1 is absent, or C1-10 aliphatic, wherein up to three methylene units of Y1 are optionally and independently replaced with G' wherein G' is —O—, —C(O)—, —N(R')—, or —S(O)$_p$—; and Y1 is optionally and independently substituted with one or more J$_d$.

Q1 is absent, or a C3-8 membered saturated, partially unsaturated, or fully unsaturated monocyclic ring having 0-3 heteroatoms independently selected from nitrogen, oxygen, and sulfur; and Q1 is optionally and independently substituted with one or more J$_b$; wherein when B is substituted with Y then Y1 and Q1 are not both absent.

R$_3$ is absent, —H, or C1-C6 alkyl optionally and independently substituted with one or more J$_a$.

R$_4$ is a C1-10 aliphatic, wherein up to three methylene units of R$_4$ are optionally and independently replaced by G' wherein G' is —O—, —C(O)—, —N(R')—, or —S(O)$_p$—; and R$_4$ is optionally and independently substituted with one ring C and independently further optionally and independently substituted with one or more J$_a$; or R$_4$ is ring C.

Ring C is a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur optionally and independently substituted with one Z or independently further optionally and independently substituted with one or more J$_b$.

Z is —Y2-Q2.

Y2 is absent, or C1-10 aliphatic, wherein up to three methylene units of Y2 are optionally and independently replaced with G' wherein G' is —O—, —C(O)—, —N(R')—, or —S(O)$_p$—; and Y2 is optionally and independently substituted with one or more J$_d$.

Q2 is absent, C3-8 membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur; and Q2 is optionally and independently substituted with one or more $J_e$; wherein when C is substituted with Z then Y2 and Q2 are not both absent.

Each R' is independently —H, or C1-C6 alkyl optionally and independently substituted with one or more $J_a$.

Each $J_a$ is independently halogen, —OR, —N(R)$_2$, —C(O)OR, —C(O)N(R)$_2$, —NRC(O)R, —NRC(O)OR, —CN, —NO$_2$, or oxo.

Each $J_b$ is independently halogen, —OR, —N(R)$_2$, —C(O)OR, —C(O)N(R)$_2$, —NRC(O)R, —NRC(O)OR, —CN, —NO$_2$, oxo, or C1-C6 alkyl optionally and independently substituted with one or more $J_a$.

Each $J_c$ is independently halogen, —OR', —N(R')$_2$, —C(O)OR', —C(O)N(R')$_2$, —NR'C(O)R', —NR'C(O)OR', —CN, —NO$_2$, or C1-C10 aliphatic optionally and independently substituted with one or more $J_a$, or C3-C8 cycloaliphatic optionally and independently substituted with one or more $J_b$.

Each $J_d$ is independently halogen, —OH, —NH$_2$, —C(O)H, —C(O)OH, —C(O)NH$_2$, —NHC(O)H, —NHC(O)OH, —CN, or —NO$_2$.

Each $J_e$ is independently halogen, —OH, —NH$_2$, —C(O)H, —C(O)OH, —C(O)NH$_2$, —NHC(O)H, —NHC(O)OH, —CN, —NO$_2$, oxo, C1-10 aliphatic, wherein up to three methylene units are optionally and independently replaced with G' wherein G' is —O—, —C(O)—, —N(R')—, or —S(O)$_p$— and the aliphatic group is optionally and independently substituted with one or more $J_d$, or $J_e$ is C3-8 cycloaliphatic optionally and independently substituted with one or more $J_b$.

Each R is independently —H or C1-C6 alkyl.

Each p is independently 0, 1, or 2.

In one embodiment the compounds of the present invention are represented by structural formula I:

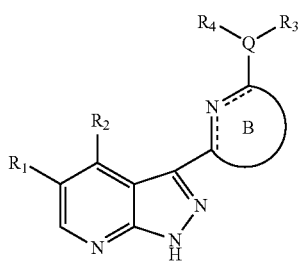

I or a pharmaceutically acceptable salt thereof.

R$_1$ is —H, halogen, —OR', —N(R')$_2$, —C(O)OR', —C(O)N(R')$_2$, —NR'C(O)R', —NR'C(O)OR', —CN, —NO$_2$, C1-C10 aliphatic optionally and independently substituted with one or more $J_a$, or C3-C8 cycloaliphatic optionally and independently substituted with one or more $J_b$.

R$_2$ is —H, halogen, —OR', —N(R')$_2$, —C(O)OR', —C(O)N(R')$_2$, —NR'C(O)R', —NR'C(O)OR', —CN, —NO$_2$, C1-C10 aliphatic optionally and independently substituted with one or more $J_a$, or C3-C8 cycloaliphatic optionally and independently substituted with one or more $J_b$.

Q is —N—, —O—, or —S—.

Ring B is a 6-membered monocyclic heteroaromatic ring optionally fused to an aromatic or non-aromatic ring; and ring B is optionally substituted with one Y and independently further optionally and independently substituted with one or more $J_c$.

Y is —Y1-Q1.

Y1 is absent, or C1-10 aliphatic, wherein up to three methylene units of Y1 are optionally and independently replaced with G' wherein G' is —O—, —C(O)—, —N(R')—, or —S(O)$_p$—; and Y1 is optionally and independently substituted with one or more $J_d$.

Q1 is absent, or a C3-8 membered saturated, partially unsaturated, or fully unsaturated monocyclic ring having 0-3 heteroatoms independently selected from nitrogen, oxygen, and sulfur; and Q1 is optionally and independently substituted with one or more $J_b$; wherein Y1 and Q1 are not both absent.

R$_3$ is absent, —H, or C1-C6 alkyl optionally and independently substituted with one or more $J_a$.

R$_4$ is a C1-10 aliphatic, wherein up to three methylene units of R$_4$ are optionally and independently replaced by G' wherein G' is —O—, —C(O)—, —N(R')—, or —S(O)$_2$—; and R$_4$ is optionally and independently substituted with one ring C and independently further optionally and independently substituted with one or more $J_a$; or R$_4$ is ring C.

Ring C is a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, and ring C is optionally substituted with one Z or independently further optionally and independently substituted with one or more $J_b$.

Z is —Y2-Q2.

Y2 is absent, or C1-10 aliphatic, wherein up to three methylene units of Y2 are optionally and independently replaced with G' wherein G' is —O—, —C(O)—, —N(R')—, or —S(O)$_p$—; and Y2 is optionally and independently substituted with one or more $J_d$.

Q2 is absent, C3-8 membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur; and Q2 is optionally and independently substituted with one or more $J_e$; wherein Y2 and Q2 are not both absent.

Each R' is independently —H, or C1-C6 alkyl optionally and independently substituted with one or more $J_a$.

Each $J_a$ is independently halogen, —OR, —N(R)$_2$, —C(O)OR, —C(O)N(R)$_2$, —NRC(O)R, —NRC(O)OR, —CN, —NO$_2$, or oxo.

Each $J_b$ is independently halogen, —OR, —N(R)$_2$, —C(O)OR, —C(O)N(R)$_2$, —NRC(O)R, —NRC(O)OR, —CN, —NO$_2$, oxo, or C1-C6 alkyl optionally and independently substituted with $J_a$.

Each $J_c$ is independently halogen, —OR', —N(R')$_2$, —C(O)OR', —C(O)N(R')$_2$, —NR'C(O)R', —NR'C(O)OR', —CN, —NO$_2$, or C1-C10 aliphatic optionally and independently substituted with one or more $J_a$, or C3-C8 cycloaliphatic optionally and independently substituted with one or more $J_b$.

Each $J_d$ is independently halogen, —CN, or —NO$_2$.

Each $J_e$ is independently halogen, —CN, —NO$_2$, oxo, C1-10 aliphatic, wherein up to three methylene units are optionally and independently replaced with G' wherein G' is —O—, —C(O)—, —N(R')—, or —S(O)$_p$— and the aliphatic group is optionally and independently substituted with one or more $J_d$, or $J_e$ is C3-8 cycloaliphatic optionally and independently substituted with one or more $J_b$.

Each R is independently —H or C1-C6 alkyl.

Each p is independently 0, 1, or 2.

In one embodiment the compounds of the present invention are represented by structural formula I:

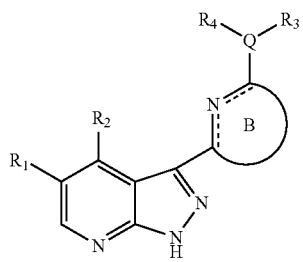

or a pharmaceutically acceptable salt thereof.

$R_1$ is —H, halogen, —OR', —N(R')$_2$, —C(O)OR', —C(O)N(R')$_2$, —NR'C(O)R', —NR'C(O)OR', —CN, —NO$_2$, C1-C10 aliphatic optionally and independently substituted with one or more $J_a$, or C3-C8 cycloaliphatic optionally and independently substituted with one or more $J_b$.

$R_2$ is —H, halogen, —OR', —N(R')$_2$, —C(O)OR', —C(O)N(R')$_2$, —NR'C(O)R', —NR'C(O)OR', —CN, —NO$_2$, C1-C10 aliphatic optionally and independently substituted with one or more $J_a$, or C3-C8 cycloaliphatic optionally and independently substituted with one or more $J_b$.

Q is —N—, —O—, or —S—.

Ring B is a 6-membered monocyclic heteroaromatic ring optionally fused to an aromatic or non-aromatic ring; and ring B is optionally substituted with one Y and independently further optionally and independently substituted with one or more $J_c$.

Y is —Y1-Q1.

Y1 is absent, or C1-10 aliphatic, wherein up to three methylene units of Y1 are optionally and independently replaced with G' wherein G' is —O—, —C(O)—, —N(R')—, or —S(O)$_p$—; and Y1 is optionally and independently substituted with one or more $J_d$.

Q1 is absent, or a C3-8 membered saturated, partially unsaturated, or fully unsaturated monocyclic ring having 0-3 heteroatoms independently selected from nitrogen, oxygen, and sulfur; and Q1 is optionally and independently substituted with one or more $J_b$; wherein Y1 and Q1 are not both absent.

$R_3$ is absent, —H, or C1-C6 alkyl optionally and independently substituted with one or more $J_a$.

$R_4$ is a C1-10 aliphatic, wherein up to three methylene units of $R_4$ are optionally and independently replaced by G' wherein G' is —O—, —C(O)—, —N(R')—, or —S(O)$_p$—; and $R_4$ is optionally and independently substituted with one ring C or independently further optionally and independently substituted with one or more $J_a$; or $R_4$ is ring C.

Ring C is a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, and ring C is optionally substituted with one Z or independently further optionally and independently substituted with one or more $J_b$.

Z is —Y2-Q2.

Y2 is absent, or C1-10 aliphatic, wherein up to three methylene units of Y2 are optionally and independently replaced with G' wherein G' is —O—, —C(O)—, —N(R')—, or —S(O)$_p$—; and Y2 is optionally and independently substituted with one or more $J_d$.

Q2 is absent, C3-8 membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur; and Q2 is optionally and independently substituted with one or more $J_e$; wherein Y2 and Q2 are not both absent.

Each R' is independently —H, or C1-C6 alkyl optionally and independently substituted with one or more $J_a$.

Each $J_a$ is independently halogen, —OR, —N(R)$_2$, —C(O)OR, —C(O)N(R)$_2$, —NRC(O)R, —NRC(O)OR, —CN, —NO$_2$, or oxo.

Each $J_b$ is independently halogen, —OR, —N(R)$_2$, —C(O)OR, —C(O)N(R)$_2$, —NRC(O)R, —NRC(O)OR, —CN, —NO$_2$, oxo, or C1-C6 alkyl optionally and independently substituted with $J_a$.

Each $J_c$ is independently halogen, —OR', —N(R')$_2$, —C(O)OR', —C(O)N(R')$_2$, —NR'C(O)R', —NR'C(O)OR', —CN, —NO$_2$, or C1-C10 aliphatic optionally and independently substituted with one or more $J_a$, or C3-C8 cycloaliphatic optionally and independently substituted with one or more $J_b$.

Each $J_d$ is independently halogen, —CN, or —NO$_2$.

Each $J_e$ is independently halogen, —CN, —NO$_2$, oxo, C1-10 aliphatic, wherein up to three methylene units are optionally and independently replaced with G' wherein G' is —O—, —C(O)—, —N(R')—, or —S(O)$_p$— and the aliphatic group is optionally and independently substituted with one or more $J_d$, or $J_e$ is C3-8 cycloaliphatic optionally and independently substituted with one or more $J_b$.

Each R is independently —H or C1-C6 alkyl.

Each p is independently 0, 1, or 2.

In a first embodiment the present invention is a compound represented by structural formula I wherein, $R_1$ is —H, halogen, C1-C10 aliphatic optionally and independently substituted with one or more $J_a$, or C3-C8 cycloaliphatic optionally and independently substituted with one or more $J_b$;

$R_2$ is —H, halogen, C1-C10 aliphatic optionally and independently substituted with one or more $J_a$, or C3-C8 cycloaliphatic optionally and independently substituted with one or more $J_b$; and the remainder of the varaibales are as described above. In certain embodiments $R_1$ is not Cl.

In a second embodiment the present invention is a compound represented by structural formula I wherein, $R_2$ is —H and the remainder of the varaibales are as described above or for the first embodiment.

In a third embodiment the present invention is a compound represented by structural formula I wherein, $R_1$ is —H, halogen or C1-C10 haloalkyl and the remainder of the varaibales are as described above or for the first or second embodiment. In certain embodiments $R_1$ is not Cl.

In a fourth embodiment the present invention is a compound represented by structural formula II or III:

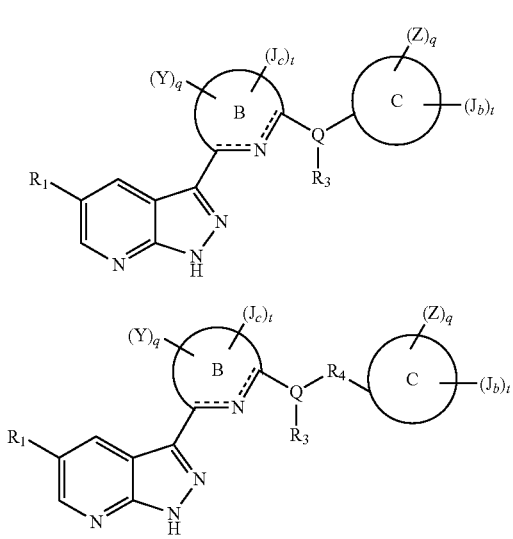

or a pharmaceutically acceptable salt thereof, wherein, $R_4$ is a C1-10 aliphatic, wherein up to three methylene units of $R_4$ are optionally and independently replaced by G' wherein G' is —O—, —C(O)—, —N(R')—, or —S(O)$_p$—; and $R_4$ is optionally and independently substituted with one or more $J_a$.

Each q is independently 0 or 1.

Each t is independently 0, 1, or 2 or alternatively t is 0 or 1-4 and the remainder of the varaibales are as described above or for the first through third embodiments.

In a fifth embodiment the present invention is a compound represented by structural formula I, II or III wherein, ring B is pyridyl, pyrazinyl, pyrimidinyl, isoquinolyl, quinazolinyl, pyridopyridyl, pyridopyradazinyl, pyrrolopyridiyl, pyrazolopyridiyl, pyrolopyrimidinyl, or pyrrolopyrazinyl, wherein ring B is optionally substituted with one Y and independently further and optionally and independently substituted with one or more 0.1, and the remainder of the varaibales are as described above or for the first through fourth embodiments.

In a sixth embodiment the present invention is a compound represented by structural formula I, II or III wherein, ring B is pyridyl, pyrazinyl, pyrimidinyl, isoquinolyl, pyrrolopyridiyl, pyrazolopyridiyl, pyrolopyrimidinyl, or pyrrolopyrazinyl, wherein ring B is optionally substituted with one Y and independently further and optionally and independently substituted with one or more $J_c$ and the remainder of the varaibales are as described above or for the first through fourth embodiments.

In a seventh embodiment the present invention is a compound represented by structural formula I, II or III wherein, ring B is pyridyl optionally substituted with one Y and independently further and optionally and independently substituted with one or more $J_c$ and the remainder of the varaibales are as described above or for the first through fourth embodiments.

In an eighth embodiment the present invention is a compound represented by structural formula I, II or III wherein, ring B is pyrazinyl optionally substituted with one Y and independently further and optionally and independently substituted with one or more $J_c$ and the remainder of the varaibales are as described above or for the first through fourth embodiments.

In a ninth embodiment the present invention is a compound represented by structural formula I, II or III wherein, ring C is selected from the group consisting of cyclopropyl, cyclopentyl, cyclobutyl, cyclohexyl, cyclohexenyl, phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, indolyl, indazolyl, benzimidazolyl, quinolyl, quinoxalyl, indolinyl, oxazolidinyl, isoxazolidinyl, thiazolidinyl, isothiazolidinyl, oxazocanyl, oxazepanyl, azabicyclopentyl, azabicyclohexyl, azabicycloheptyl, azabicyclooctyl, azabicyclononyl, azabicyclodecyl, diazabicyclohexyl, diazabicycloheptyl, azetidinyl, isoindolinyl, isoindolyl, dihydroindazolyl, dihydrobenzimidazolyl, morpholinyl, tetrahydropyridyl, dihydropyridyl, tetrahydropyrazinyl, dihydropyrazinyl, tetrahydropyrimidinyl, dihydropyrimidinyl, dihydropyrrolyl, dihydropyrazolyl, dihydroimidazolyl, octahydropyrrolopyrazyl, octahydropyrrolopyridyl, octahydropyridopyrazyl, octahydropyridopyridyl, diazabicyclooctyl, diazabicyclononyl, diazabicyclodecyl, thiazepanyl, and thiazocanyl wherein each ring is optionally substituted with one Z and independently further optionally and independently substituted with one or more $J_b$ and the remainder of the varaibales are as described above or for the fifth through eighth embodiments.

In a tenth embodiment the present invention is a compound represented by structural formula I, II or III wherein, ring C is selected from the group consisting of cyclohexyl, diazabicyclooctyl, phenyl, pyridyl, pyrazinyl, pyrimidinyl, pyrrolyl, imidazolyl, pyrazolyl, oxazalolyl, oxadiazolyl, thiazolyl, azetidinyl, morpholinyl, azepanyl, diazabicycloheptyl, diazabicyclooctyl, indolyl, tetrahydropyridyl, dihydropyridyl, octahydropyrrolopyrazyl, octahydropyrrolopyridyl, octahydropyridopyrazyl, octahydropyridopyridyl, thiadiazolyl, piperidinyl, piperazinyl, pyrrolidinyl, diazepanyl, and oxazepanyl wherein each ring is independently optionally substituted with one Z and independently further optionally and independently substituted with one or more $J_b$ and the remainder of the varaibales are as described above or for the fifth through eighth embodiments.

In an eleventh embodiment the present invention is a compound represented by structural formula I, II or III wherein, ring C is selected from the group consisting of cyclohexyl, 3,8-diazabicyclo[3.2.1.]octane, phenyl, pyridyl, piperidinyl, piperazinyl, diazapanyl, pyrrolidinyl, pyrrolyl, pyrrazolyl, azetidinyl, morpholinyl, azepanyl, 2,5 diazabicycloheptyl, diazabicyclooctyl, indolyl, tetrahydropyridyl, octahydro-1H-pyrrolo[2,3-b]pyrazyl, octahydropyrrolo[1,2-a]pyrazyl, and oxazepanyl wherein each ring is optionally substituted with one Z and independently further optionally and independently substituted with one or more $J_b$ and the remainder of the varaibales are as described above or for the fifth through eighth embodiments.

In a twelfth embodiment the present invention is a compound represented by structural formula I, II or III wherein, ring C is selected from the group consisting of cyclohexyl, phenyl, piperidinyl, piperazinyl, diazapanyl, pyrrolidinyl, azetidinyl, and azepanyl, wherein each ring is optionally substituted with one Z and independently further optionally and independently substituted with one or more $J_b$ and the remainder of the varaibales are as described above or for the fifth through eighth embodiments.

In a thirteenth embodiment the present invention is a compound represented by structural formula I, II or III wherein, ring C is represented a structural formula selected from the group consisting of:

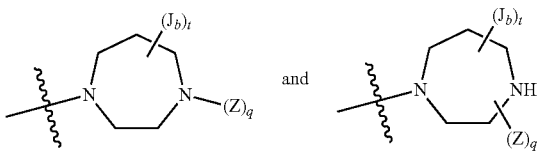

q is 0 or 1.

t is 0, 1 or 2 or alternatively t is 0, 1 or more or alternatively t is 0 or 1-4 and the remainder of the varaibales are as described above or for the fifth through eighth embodiments.

In a fourteenth embodiment the present invention is a compound represented by structural formula I, II or III wherein, ring C is represented by a structural formula selected from the group consisting of:

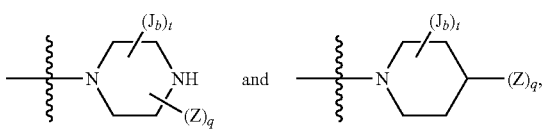

q is 0 or 1.

t is 0, 1 or 2 or alternatively t is 0, 1 or more or alternatively t is 0 or 1-4 and the remainder of the varaibales are as described above or for the fifth through eighth embodiments.

In a fifteenth embodiment the present invention is a compound represented by structural formula I, II or III wherein, ring C is represented by a structural formula represented by:

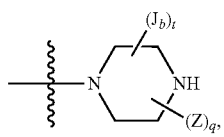

q is 0 or 1.

t is 0 or 1 or alternatively t is 0, 1 or more or alternatively t is 0 or 1-4 and the remainder of the varaibales are as described above or for the fifth through eighth embodiments.

In a sixteenth embodiment the present invention is a compound represented by structural formula I, II or III wherein, ring C is represented by a structural formula selected from the group consisting of:

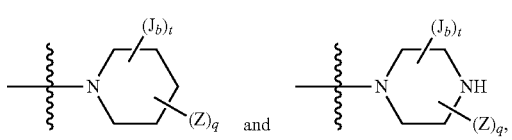

q is 0 or 1.

t is 0, 1 or 2 or alternatively t is 0, 1 or more or alternatively t is 0 or 1-4 and the remainder of the varaibales are as described above or for the fifth through eighth embodiments.

In a seventeenth embodiment the present invention is a compound represented by structural formula I, II or III wherein, ring C is represented by a structural formula represented by:

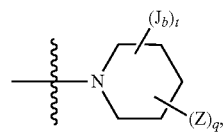

q is 0 or 1; and t is 0 or 1 or alternatively t is 0, 1 or more or alternatively t is 0 or 1-4 and the remainder of the varaibales are as described above or for the fifth through eighth embodiments.

In an eighteenth embodiment the present invention is a compound represented by structural formula I, II or III wherein, ring C is represented by a structural formula represented by:

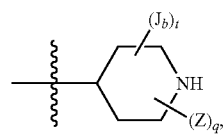

q is 0 or 1; and t is 0 or 1 or alternatively t is 0, 1 or more or alternatively t is 0 or 1-4 and the remainder of the varaibales are as described above or for the fifth through eighth embodiments. In the structural formulas herein when, for example, $(Z)_q$ is attached to N, when q is 0 then N is NH.

In a nineteenth embodiment the present invention is a compound represented by structural formula I, II or III wherein, $R_4$ is a C1-10 aliphatic, wherein up to three methylene units of $R_4$ are optionally and independently replaced by G' wherein G' is —O—, —C(O)—, —N(R')—, or —S(O)$_p$—; and $R_4$ is optionally and independently substituted with one or more $J_a$ and the remainder of the varaibales are as described above or for the first through eighteenth embodiments.

In a twentieth embodiment the present invention is a compound represented by structural formula I, II or Ill wherein, $R_4$ is a C2-10 aliphatic, wherein up to three methylene units of $R_4$ are optionally and independently replaced by G' wherein G' is —O—, or —N(R')—; and $R_4$ is optionally and independently substituted with one or more $J_a$ and the remainder of the variables are as described above or for the first, second or nineteenth embodiment.

As used herein "one or more" means, for example, that all substitutable carbon atoms can be substituted, for example, up to 6 carbons atoms, up to 5 carbon atoms, up to 3 carbon atoms, up to 2 carbon atoms, or one carbon atom can be substituted.

As described herein, a specified number range of atoms includes any integer therein. For example, a group having from 1-4 atoms could have 1, 2, 3, or 4 atoms.

As used here the terms "absent" and "a bond" can be used interchangeably to mean the variable does not exits in that embodiment, that is the variable does not represent an atom or groups of atoms.

The term "stable", as used herein, refers to compounds that are not substantially altered when subjected to conditions to allow for their production, detection, recovery, storage, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), or branched, hydrocarbon chain that is completely saturated or that contains one or more units of unsaturation but is non-aromatic.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds.

The term "cycloaliphatic" (or "carbocycle" or "carbocyclyl" or "carbocyclic") refers to a non-aromatic monocyclic carbon containing ring which can be saturated or contain one or more units of unsaturation, having three to fourteen ring carbon atoms. The term includes polycyclic fused, spiro or bridged carbocyclic ring systems. The term also includes polycyclic ring systems in which the carbocyclic ring can be fused to one or more non-aromatic carbocyclic or heterocyclic rings or one or more aromatic rings or combination thereof, wherein the radical or point of attachment is on the carbocyclic ring. Fused bicyclic ring systems comprise two rings which share two adjoining ring atoms, bridged bicyclic group comprise two rings which share three or four adjacent ring atoms, Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, cyclopropyl and cyclobutyl.

The term "heterocycle" (or "heterocyclyl", or "heterocyclic") as used herein means refers to a non-aromatic monocyclic ring which can be saturated or contain one or more units of unsaturation, having three to fourteen ring atoms in which one or more ring carbons is replaced by a heteroatom such as, N, S, or O. The term includes polycyclic fused, Spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 3-piperazinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, dihydro-benzimidazol-2-onyl, and 1,3-dihydro-imidazol-2-onyl, azabicyclopentyl, azabicyclohexyl, azabicycloheptyl, azabicyclooctyl, azabicyclononyl, azabicyclodecyl, diazabicyclohexyl, diazabicycloheptyl, dihydroindazolyl, dihydrobenzimidazolyl, tetrahydropyridyl, dihydropyridyl, tetrahydropyrazinyl, dihydropyrazinyl, tetrahydropyrimidinyl, dihydropyrimidinyl, dihydropyrrolyl, dihydropyrazolyl, dihydroimidazolyl, octahydropyrrolopyrazyl, octahydropyrrolopyridyl, octahydropyridopyrazyl, octahydropyridopyridyl, diazabicyclooctyl, diazabicyclononyl, and diazabicyclodecyl.

As used herein, unless otherwise stated, bicyclic rings can be fused, prior and bridged.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the molecule through an oxygen ("alkoxy" e.g., —O-alkyl) or sulfur ("thioalkyl" e.g., —S-alkyl) atom.

The terms "haloalkyl", "haloalkenyl", "haloaliphatic", and "haloalkoxy" (or "aminoalkyl", "hydroxyalkyl" etc.,) mean alkyl, alkenyl or alkoxy, as the case may be, substituted with one or more halogen atoms. This term includes perfluorinated alkyl groups, such as $—CF_3$ and $—CF_2CF_3$.

The terms "halogen", "halo", and "hal" mean F, CI, Br, or I. The term haloaliphatic and —O (haloaliphatic) include, mono- di- and tri-halo substituted aliphatic groups.

The term "aryl" used alone or as part of a larger moiety as in "aralkyl", "aralkoxy", "aryloxyalkyl", or "heteroaryl" refers to carbocyclic and or heterocyclic aromatic ring systems. The term "aryl" may be used interchangeably with the term "aryl ring".

Carbocyclic aromatic ring groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is fused to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, where indicated a methylene unit of an aliphatic chain is optionally replaced with another atom or group. Examples of such atoms or groups include, but are not limited to, G which includes, —N(R')—, —O—, —C(O)—, —C(=N—CN)—, —C(=NR')— —C(=NOR')—, —S—, —S(O)—, and —S(O)$_2$—. These atoms or groups can be combined to form larger groups. Examples of such larger groups include, but are not limited to, —OC(O)—, —C(O)CO—, —CO$_2$—, —C(=N—CN), —N(R')C(O)—, —N(R')C(O)O—, —S(O)$_2$N(R')—, —N(R)SO$_2$—, —N(R')C(O)N(R')—, —OC(O)N(R')—, and —N(R')SO$_2$N(R')—, wherein R' is defined herein.

Only those replacement and combinations of groups that result in a stable structure are contemplated. Optional replacements can occur both within the chain and/or at either end of the chain; i.e. both at the point of attachment and/or also at the terminal end. Two optional replacements can also be adjacent to each other within a chain so long as it results in a chemically stable compound.

In some embodiments the optional replacements can also completely replace all of the carbon atoms in a chain. For example, a $C_3$ aliphatic can be optionally replaced by —N(R')—, —C(O)—, and —N(R')— to form —N(R)C(O)N(R')— (a urea), or a $C_1$ aliphatic can be optionally be replaced by, for example, —O—, —NH— etc. In certain instances of these embodiments the chain is a linker.

Unless otherwise indicated, if the replacement occurs at the terminal end, the replacement atom is bound to an H on the terminal end. For example, if —CH$_2$CH$_2$CH$_3$ were optionally replaced with —O—, the resulting compound could be —OCH$_2$CH$_3$, —CH$_2$OCH$_3$, or —CH$_2$CH$_2$OH, or if —CH$_2$CH$_3$ were optionally replaced with —O—, the resulting compound could be —OCH$_3$, or —CH$_2$CH$_2$OH, or if —CH$_2$CH$_3$ were optionally replaced with —C(O)—, the resulting compound could be —C(O)CH$_3$, or —CH$_2$C(O)H.

In an alternative embodiment where specified herein, aliphatic chains in which up to three (0-3) methylene groups are optionally replaced by G', wherein G' is —N(R')—, —O—, —C(O)—, or —S(O)$_p$—, (wherein R' and p are as defined herein) require at least one unreplaced methylene group (—CH(substituent)- or —CH$_2$—) in the chain. For example, the methylene group in a $C_1$ aliphatic cannot be replaced by, for example, —OH, —NH$_2$ etc., to give —OH and —NH$_2$ as the substituent without any methylene group in the chain, or ii) two methylene groups in a $C_2$ aliphatic groups cannot be replaced by —C(O)— and —O— to give —C(O)OH. In certain instances of these alternative embodiment the chain is not a linker but rather a substituent only joined to the rest of the molecule in one place. These aliphatic groups are further substituted as defined herein.

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

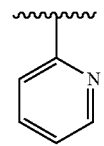

also represents

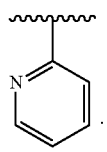

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As described herein, where indicated compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position.

Only those choices and combinations of substituents that result in a stable structure are contemplated. Such choices and combinations will be apparent to those of ordinary skill in the art and may be determined without undue experimentation.

The term "ring atom" is an atom such as C, N, O or S that is in the ring of an aromatic group, cycloalkyl group or non-aromatic heterocyclic ring.

A "substitutable ring atom" in an aromatic or non-aromatic ring group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

An optionally substituted aryl group as defined herein may contain one or more substitutable ring atoms, which may be bonded to a suitable substituent. Examples of suitable substituents on a substitutable ring carbon atom of an aryl group includes $R^@$. $R^@$ is —Ra, —Br, —Cl, —I, —F, —ORa, —SRa, —O—CORa, —CORa, —CSRa, —CN, —NO$_2$, —NCS, —SO$_3$H, —N(RaRb), —COORa, —NRcNRcCORa, —NRcRcCO$_2$Ra, —CHO, —CON(RaRb), —OC(O)N(RaRb), —CSN(RaRb), —NRcCORa, —NRcCOORa, —NRcCSRa, —NRcCON(RaRb), —NRcNRcC(O)N(RaRb), —NRcCSN(RaRb), —C(=NRc)—N(RaRb), —C(=S)N(RaRb), —NRd—C(=NRc)—N(RaRb), —NRcNRaRb, —S(O)$_p$NRaRb, —NRcSO$_2$N(RaRb), —NRcS(O)$_p$Ra, —S(O)$_p$Ra, —OS(O)$_p$NRaRb or —OS(O)$_p$Ra; wherein p is 1 or 2.

Ra-Rd are each independently —H, an aliphatic group, aromatic group, non-aromatic carbocyclic or heterocyclic group or —N(RaRb), taken together, form a non-aromatic heterocyclic group. The aliphatic, aromatic and non-aromatic heterocyclic group represented by Ra-Rd and the non-aromatic heterocyclic group represented by —N(RaRb) are each optionally and independently substituted with one or more groups represented by Preferably Ra-Rd are unsubstituted.

$R^\#$ is halogen, $R^+$, —O$R^+$, —S$R^+$, —NO$_2$, —CN, —N($R^+$)$_2$, —CO$R^+$, —COO$R^+$, —NHCO$_2R^+$, —NHC(O)$R^+$, —NHNHC(O)$R^+$, —NHC(O)N($R^+$)$_2$, —NHNHC(O)N($R^+$)$_2$, —NHNHCO$_2R^+$, —C(O)N($R^+$)$_2$, —OC(O)$R^+$, —OC(O)N($R^+$)$_2$, —S(O)$_2R^+$, —SO$_2$N($R^+$)$_2$, —S(O)$R^+$, —NHSO$_2$N($R^+$)$_2$, —NHSO$_2R^+$, —C(=S)N($R^+$)$_2$, or —C(=NH)—N(R)$_2$.

$R^+$ is —H, a C1-C4 alkyl group, a monocyclic aryl group, a non-aromatic carbocyclic or heterocyclic group each optionally substituted with alkyl, haloalkyl, alkoxy, haloalkoxy, halogen, —CN, —NO$_2$, amine, alkylamine or dialkylamine. Preferably R+ is unsubstituted.

An optionally substituted aliphatic or a non-aromatic heterocyclic or carbocyclic group as used herein may contain one or more substituents. Examples of suitable substituents for an aliphatic group or a ring carbon of a non-aromatic heterocyclic group is R". R" includes those substituents listed above for $R^@$ and =O, =S, =NNHR, =NN(R)2, =NNHC(O)R, =NNHCO2 (alkyl), =NNHSO2 (alkyl), =NR, spiro cycloalkyl group or fused cycloalkyl group. Each R is independently selected from hydrogen, an unsubstituted alkyl group or a substituted alkyl group. Examples of substituents on the alkyl group represented by R include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

A preferred position for substitution of a non-aromatic nitrogen-containing heterocyclic group is the nitrogen ring atom. Suitable substituents on the nitrogen of a non-aromatic heterocyclic group or heteroaryl group include —R^, —N(R^)$_2$, C(O)R^, CO$_2$R^, —C(O)C(O)R^, —SO$_2$R^, SO$_2$N(R^)$_2$, C(=S)N(R^)$_2$, C(=NH)—N(R^)$_2$, and —NR^SO$_2$R^; wherein R^ is hydrogen, an aliphatic group, a substituted aliphatic group, aryl, substituted aryl, heterocyclic or carbocyclic ring or a substituted heterocyclic or carbocyclic ring. Examples of substituents on the group represented by R^ include alkyl, haloalkoxy, haloalkyl, alkoxyalkyl, sulfonyl, alkylsulfonyl, halogen, nitro, cyano, hydroxy, aryl, carbocyclic or heterocyclic ring, oxo, amino, alkylamino, dialkylamino, aminocarbonyl, alkylaminocarbonyl, dialkylaminocarbonyloxy, alkoxy, carboxy, alkoxycarbonyl, or alkylcarbonyl. Preferably R^ is not substituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

As used herein an optionally substituted aralkyl can be substituted on both the alkyl and the aryl portion. Unless otherwise indicated as used herein optionally substituted aralkyl is optionally substituted on the aryl portion.

The compounds of the invention are defined herein by their chemical structures and/or chemical names. Where a compound is referred to by both a Chemical structure and a chemical name, and the chemical structure and chemical name conflict, the chemical structure is determinative of the compound's identity.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds of this invention, pharmaceutically acceptable solvates (e.g., hydrates) and clathrates of the compounds of this invention may also be employed in compositions to treat or prevent the herein identified disorders.

As used herein, the term "pharmaceutically acceptable solvate," is a solvate formed from the association of one or more pharmaceutically acceptable solvent molecules to one of the compounds the invention. The term solvate includes hydrates (e.g., hemihydrate, monohydrate, dihydrate, trihydrate, tetrahydrate, and the like).

As used herein, the term "hydrate" means a compound of the present invention or a salt thereof, that further includes a stoichiometric or non-stoichiometric amount of water bound by non-covalent intermolecular forces.

As used herein, he term "clathrate" means a compound of the present invention or a salt thereof in the form of a crystal lattice that contains spaces (e.g., channels) that have a guest molecule (e.g., a solvent or water) trapped within.

In addition to the compounds of this invention, pharmaceutically acceptable derivatives or prodrugs of the compounds of this invention may also be employed in compositions to treat or prevent the herein identified disorders.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of the invention that comprise —NO, —NO2, —ONO, or —ONO2 moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" includes any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

In one embodiment the present invention is a pharmaceutical composition comprising a compound of the present invention and a pharmaceutically acceptable carrier, diluent, adjuvant or vehicle. In one embodiment the present invention is a pharmaceutical composition comprising an effective amount of compound of the present invention and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to a subject as defined herein. These pharmaceutical compositions, which comprise an amount of the protein inhibitor effective to treat or prevent a protein kinase-mediated condition and a pharmaceutically acceptable carrier, are another embodiment of the present invention.

In one embodiment the present invention is a method of treating or preventing a protein kinase-mediated disorder in a subject in need thereof, comprising administering to the subject an effective amount of a compound composition or a pharmaceutically acceptable salt of the present invention as described herein. In another embodiment, the present invention is the use of an effective amount of a compound, composition or a pharmaceutically acceptable salt described herein for treating or preventing a disease or disorder, described herein, in a subject in need thereof. In yet another embodiment, the present invention is the use of an effective amount of a compound, composition or a pharmaceutically acceptable salt described herein for the manufacture of a medicament method for the treatment or prevention of a disease or disorder, described herein, in a subject in need thereof. In one embodiment the protein kinase mediated disease is a protein kinase C (PKC) mediated disease. In another embodiment the protein kinase mediated disease is a protein kinase C theta (PKCtheta)-mediated disease.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, an "effective amount" refers to an amount sufficient to elicit the desired biological response. In the present invention the desired biological response is to reduce or ameliorate the severity, duration, progression, or onset of a protein kinase-mediated condition, prevent the advancement of a protein kinase-mediated condition, cause the regression of a protein kinase-mediated condition, prevent the recurrence, development, onset or progression of a symptom associated with a protein kinase-mediated condition, or enhance or improve the prophylactic or therapeutic effect(s) of another therapy. The precise amount of compound administered to a subject will depend on the mode of administration, the type and severity of the disease or condition and on the characteristics of the subject, such as general health, age, sex, body weight and tolerance to drugs. It will also depend on the degree, severity and type of protein kinase-mediated condition, and the mode of administration. The skilled artisan will be able to determine appropriate dosages depending on these and other factors. When co-administered with other agents, e.g., when co-administered with an protein kinase-mediated condition agent, an "effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

As used herein, the terms "treat", "treatment" and "treating" refer to the reduction or amelioration of the progression, severity and/or duration of a protein kinase-mediated condition, or the amelioration of one or more symptoms (preferably, one or more discernible symptoms) of a protein kinase-mediated condition resulting from the administration of one or more therapies (e.g., one or more therapeutic agents such as a compound of the invention). In specific embodiments, the terms "treat", "treatment" and "treating" refer to the amelioration of at least one measurable physical parameter of a protein kinase-mediated condition. In other embodiments the terms "treat", "treatment" and "treating" refer to the inhibition of the progression of a protein kinase-mediated condition, either physically by, e.g., stabilization of a discernible symptom, physiologically by, e.g., stabilization of a physical parameter, or both. In other embodiments the terms "treat", "treatment" and "treating" refer to the reduction or stabilization of a protein kinase-mediated condition.

As used herein, the terms "prevent", "prevention" and "preventing" refer to the reduction in the risk of acquiring or developing a given protein kinase-mediated condition, or the reduction or inhibition of the recurrence or a protein kinase-mediated condition. In one embodiment, a compound of the invention is administered as a preventative measure to a patient, preferably a human, having a genetic predisposition to any of the conditions, diseases or disorders described herein.

As used herein, the terms, "disease", "disorder" and "condition" may be used interchangeably here to refer to a protein kinase-mediated condition.

In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor. In some embodiments, said protein kinase inhibitor is a PKCtheta inhibitor.

The term "protein kinase-mediated condition", as used herein means any disease or other deleterious condition in which a protein kinase plays a role. Such conditions include, without limitation, autoimmune diseases, inflammatory diseases, proliferative and hyperproliferative diseases, immunologically-mediated diseases, immuno-deficiency disorders, immunomodulatory or immunosuppressive disorder, bone diseases, metabolic diseases, neurological and neurodegenerative diseases, cardiovascular diseases, hormone related diseases, diabetes, allergies, asthma, and Alzheimer's disease.

The term "PKC-mediated condition", as used herein means any disease or other deleterious condition in which PKC plays a role. Such conditions include, without limitation, those listed above, and in particular, T-cell mediated diseases, including without limitation autoimmune diseases, chronic or acute inflammatory diseases, and proliferative and hyperproliferative diseases.

The term "PKCtheta-mediated condition", as used herein means any disease or other deleterious condition in which PKCtheta plays a role. Such conditions include, diseases, without limitation, those listed above, and in particular, autoimmune diseases, chronic or acute inflammatory diseases, and proliferative and hyperproliferative diseases.

As used herein, the term "inflammatory disease" or "inflammatory disorder" refers to pathological states resulting in inflammation, typically caused by leukocyte infiltration. Examples of such disorders include inflammatory skin diseases, including, without limitation, psoriasis and atopic dermatitis; systemic scleroderma and sclerosis; responses associated with inflammatory bowel disease (IBD) (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); dermatitis; meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue or organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; etc.

Proliferative or hyperproliferative diseases are characterized by excessive or abnormal cell proliferation. Such diseases include, without limitation, cancer and myeloproliferative disorders.

The term "cancers" includes, but is not limited to, the following cancers: epidermoid Oral: Cardiac: Lung: Gastrointestinal: Genitourinary tract: Liver: Bone: Nervous system: Gynecological: Hematologic: Thyroid gland: and Adrenal glands. Hematologic cancers include: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, and psoriasis. Thus, the term "cancerous cell" as provided herein, includes a cell afflicted by any one of the above-identified conditions.

The term "myeloproliferative disorders", includes disorders such as polycythemia vera, thrombocythemia, myeloid metaplasia with myelofibrosis, hypereosinophilic syndrome, juvenile myelomonocytic leukaemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Examples of neurodegenerative diseases include, without limitation, Alzheimer's disease Huntington's disease, Parkinson's disease, AIDS-associated dementia, and bipolar disorder.

In one embodiment the PKCtheta mediated disease includes, without limitation, chronic inflammation, autoimmune diabetes, rheumatoid arthritis (RA), rheumatoid spondylitis, gouty arthritis and other arthritic conditions, multiple sclerosis (MS), asthma, systemic lupus erythrematosis, adult respiratory distress syndrome, Behcet's disease, psoriasis, chronic pulmonary inflammatory disease, graft versus host reaction, Crohn's Disease, ulcerative colitis, inflammatory bowel disease (IBD), which includes celiac disease and irritable bowel syndrome; Alzheimer's disease, T-cell leukaemia, lymphoma, transplant rejection, cancer and pyresis, along with any disease or disorder that relates to inflammation and related disorders.

In one embodiment the PKCtheta mediated disease includes, such as, arthritis, rheumatoid arthritis, osteoarthritis, joint inflammation, lupus, multiple sclerosis, asthma, psoriasis, cancer, T-cell lymphomas, leukaemia, diabetes type I or II, and inflammatory bowel diseases, transplant rejection, Crohn's disease and colitis.

Examples of autoimmune diseases include, without limitation, multiple sclerosis, rheumatoid arthritis and irritable bowel disease.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The dosage regimen utilizing the compounds of Structural Formula I, II or III can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compound of Structural Formula I, II or III required to treat, for example, to prevent, inhibit (fully or partially) or arrest the progress of the disease.

Dosages of the compounds of Structural Formula I, II or III can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosings such as twice, three or four times per day.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

An effective amount can be achieved in the method or pharmaceutical composition of the invention employing a compound of Structural Formula I, II or III or a pharmaceutically acceptable salt or solvate (e.g., hydrate) thereof alone or in combination with an additional suitable therapeutic agent, for example, a cancer-therapeutic agent. When combination therapy is employed, an effective amount can be achieved using a first amount of a compound of Structural Formula I, II or III or a pharmaceutically acceptable salt or solvate (e.g., hydrate) thereof and a second amount of an additional suitable therapeutic agent.

In one embodiment, the compound of Structural Formula I, II or III and the additional therapeutic agent, are each administered in an effective amount (i.e., each in an amount which would be therapeutically effective if administered alone). In another embodiment, the compound of Structural Formula I, II or III and the additional therapeutic agent, are each administered in an amount which alone does not provide a therapeutic effect (a sub-therapeutic dose). In yet another embodiment, the compound of Structural Formula I, II or III can be administered in an effective amount, while the additional therapeutic agent is administered in a sub-therapeutic dose. In still another embodiment, the compound of Structural Formula I, II or III can be administered in a sub-therapeutic dose, while the additional therapeutic agent, for example, a suitable cancer-therapeutic agent is administered in an effective amount.

As used herein, the terms "in combination" or "coadministration" can be used interchangeably to refer to the use of more than one therapies (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manlier, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

When coadministration involves the separate administration of the first amount of a compound of Structural Formula I, II or III and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Structural Formula I, II or III and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of coadministration of a first amount of a compound of Structural Formula I, II or III and a second amount of an additional therapeutic agent can result in an enhanced or synergistic therapeutic effect, wherein the combined effect is greater than the additive effect that would result from separate administration of the first amount of the compound of Structural Formula I, II or III and the second amount of the additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

In some embodiments, said additional therapeutic agent is selected from a cancer-therapeutic agent, such as, an anti-cancer agent, an anti-proliferative agent, or a chemotherapeutic agent.

In some embodiments, said additional therapeutic agent is selected from camptothecin, the MEK inhibitor: U0126, a KSP (kinesin spindle protein) inhibitor, adriamycin, interferons, and platinum derivatives, such as Cisplatin.

In other embodiments, said additional therapeutic agent is selected from taxanes; inhibitors of bcr-abl (such as Gleevec, dasatinib, and nilotinib); inhibitors of EGFR (such as Tarceva and Iressa); DNA damaging agents (such as cisplatin, oxaliplatin, carboplatin, topoisomerase inhibitors, and anthracyclines); and antimetabolites (such as AraC and 5-FU).

In yet other embodiments, said additional therapeutic agent is selected from camptothecin, doxorubicin, idarubicin, Cisplatin, taxol, taxotere, vincristine, tarceva, the MEK inhibitor, U0126, a KSP inhibitor, vorinostat, Gleevec, dasatinib, and nilotinib.

In another embodiment, said additional therapeutic agent is selected from Her-2 inhibitors (such as Herceptin); HDAC inhibitors (such as vorinostat), VEGFR inhibitors (such as Avastin), c-KIT and FLT-3 inhibitors (such as sunitinib), BRAF inhibitors (such as Bayer's BAY 43-9006) MEK inhibitors (such as Pfizer's PD0325901); and spindle poisons (such as Epothilones and paclitaxel protein-bound particles (such as Abraxane®).

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the compounds of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

As inhibitors of protein kinases, the compounds and compositions of this invention are also useful in biological samples. One aspect of the invention relates to inhibiting protein kinase activity in a biological sample, which method comprises contacting said biological sample with a compound of formula I, II or III or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention is set forth in the Examples below.

Another aspect of this invention relates to the use of the compounds described here (in particular those with moderate observed affinity for biochemical targets (IC50 1-10 μM)) as start points for chemistry optimisation. In particular, one aspect of this invention relates to routine inhibition studies against a target enzyme for chemical optimisation.

Another aspect of this invention relates to the use of the compounds described herein for crystallography (in particular those with moderate observed affinity for biochemical targets): In particular, the one aspect of this invention relates to the generation of co-complex crystal structures with compounds described herein.

Another aspect of this invention relates to the use of the compounds described herein as chemical tools to probe target biology in vitro and in vivo: In particular inhibitors with moderate affinity in biochemical assays can be used to probe the biological impact of inhibiting a target enzyme in cells and in whole animal models of disease.

Another aspect of the invention provides a method for modulating enzyme activity by contacting a compound of formula I, II or III with a protein kinase.

ABBREVIATIONS

The following abbreviations are used:
DMSO dimethyl sulfoxide
TCA trichloroacetic acid
ATP adenosine triphosphate
BSA bovine serum albumin
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time In some embodiments, the compounds of this invention are represented in Table 1. In certain embodiments, the variables used herein are as defined in the specific embodiments as shown in Table 1.

TABLE 1

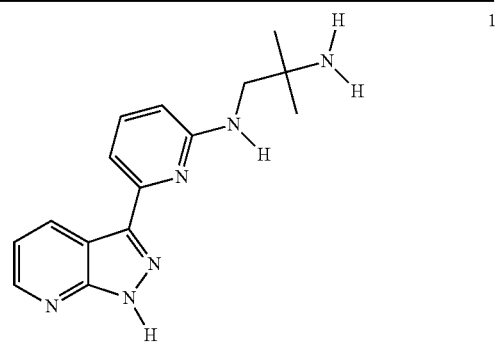

1

TABLE 1-continued
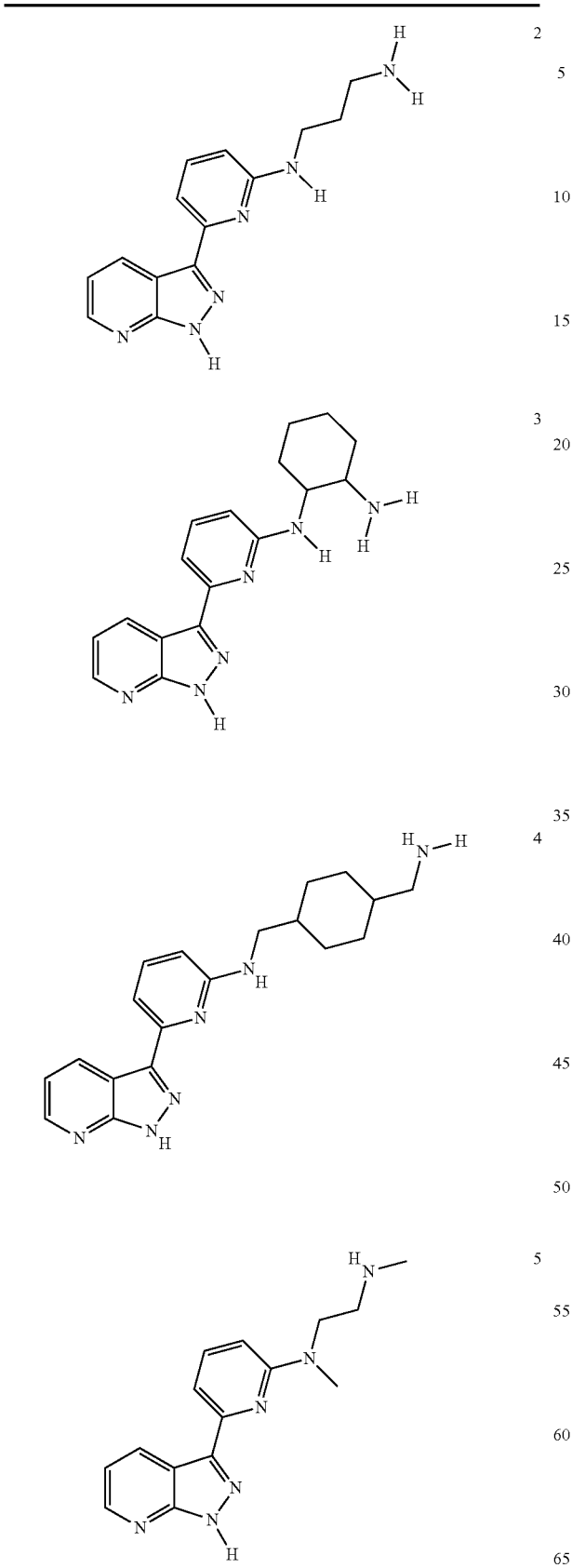
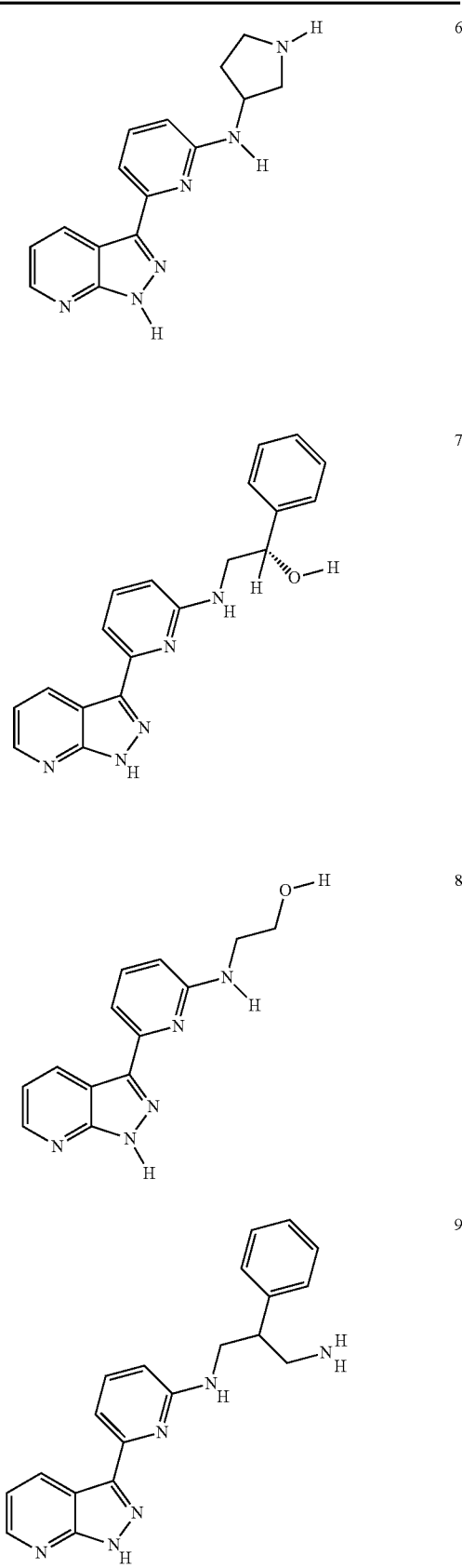

TABLE 1-continued
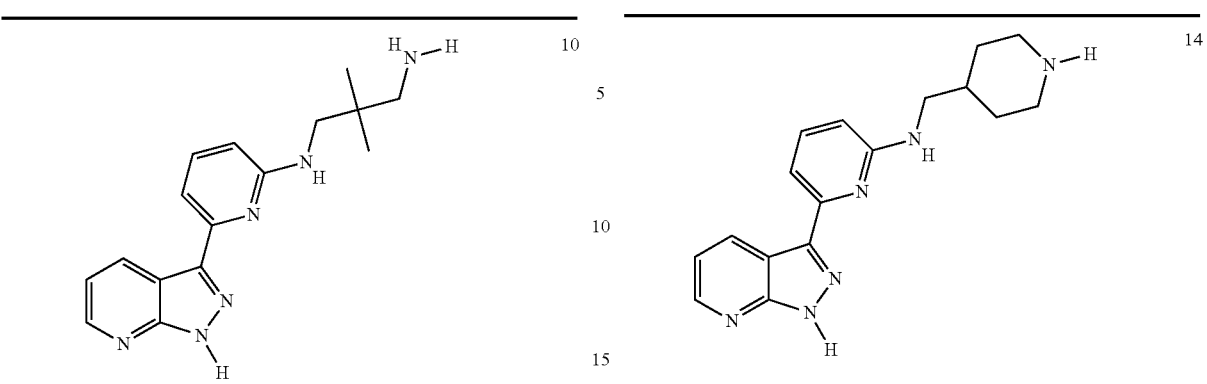
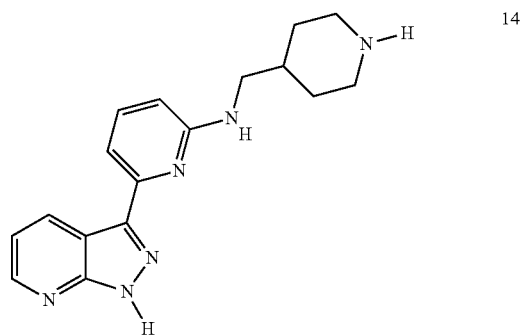
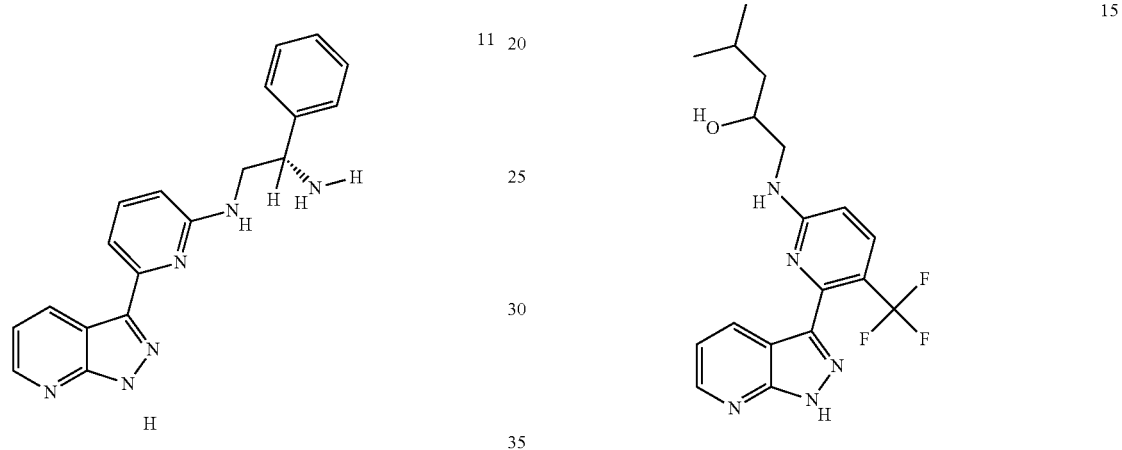
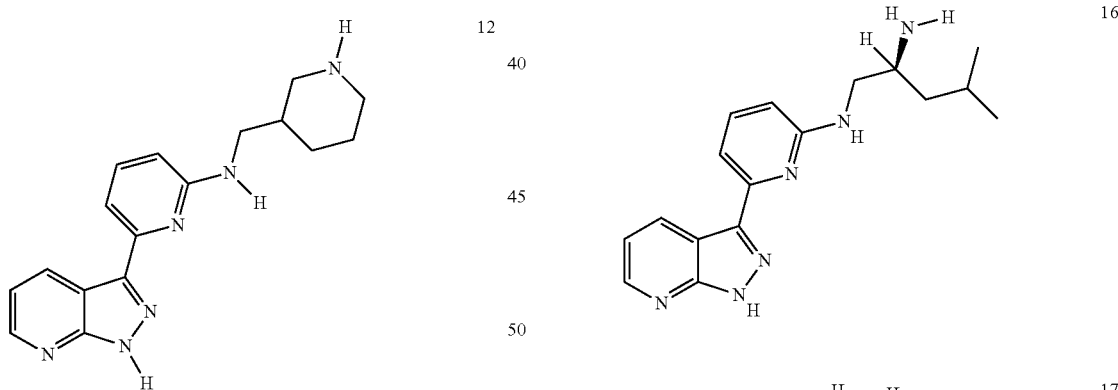
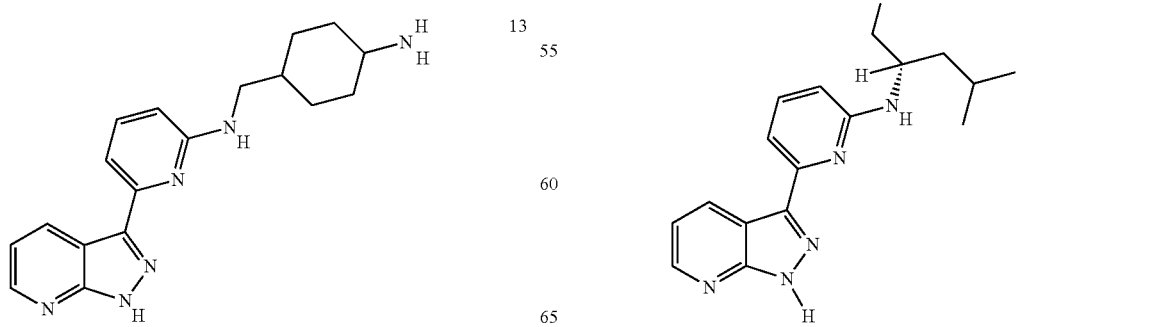

TABLE 1-continued
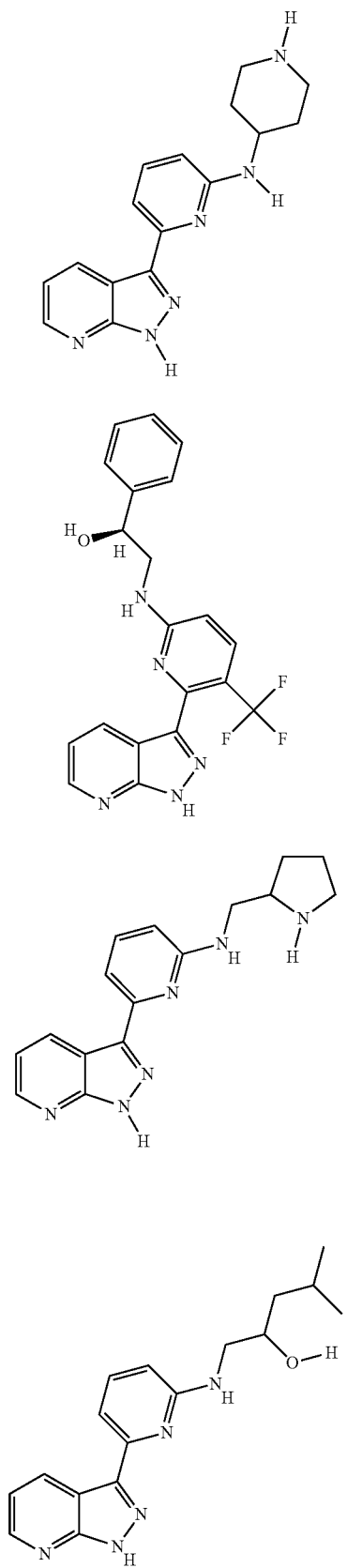
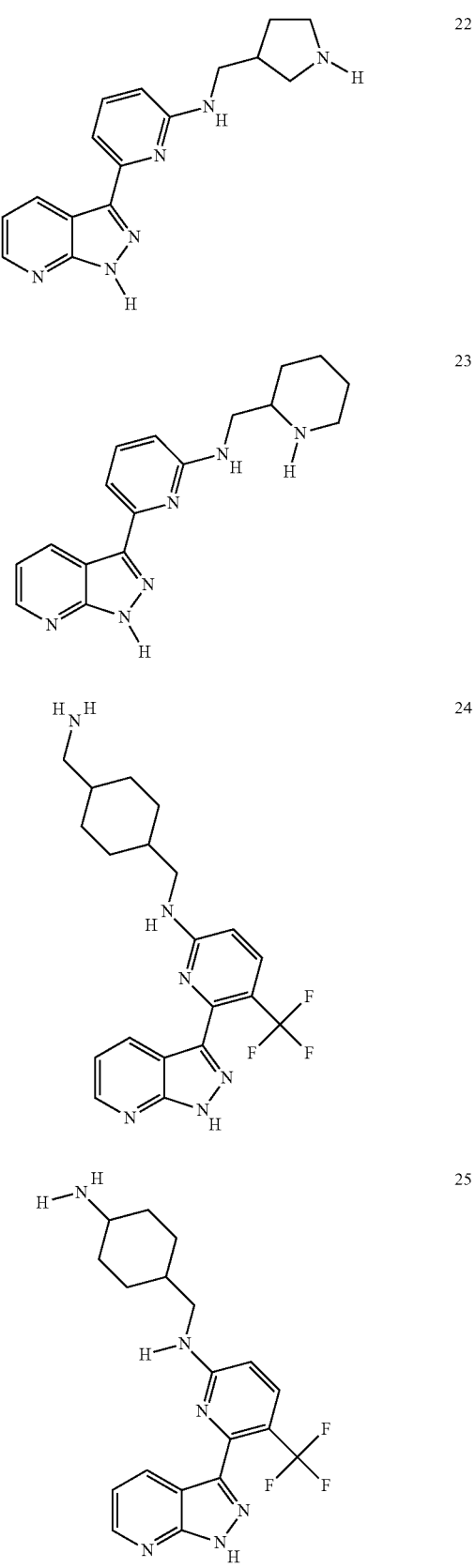

TABLE 1-continued
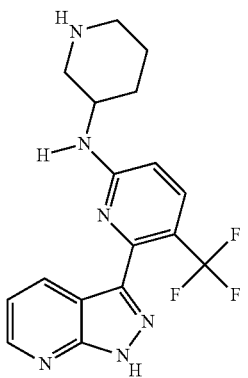 26
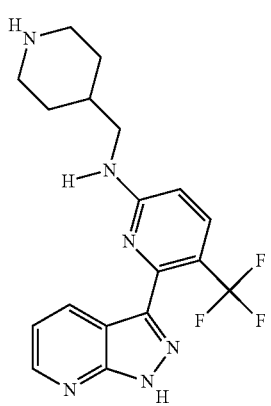 27
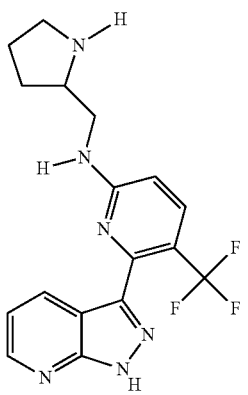 28
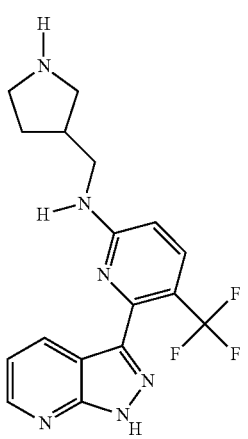 29
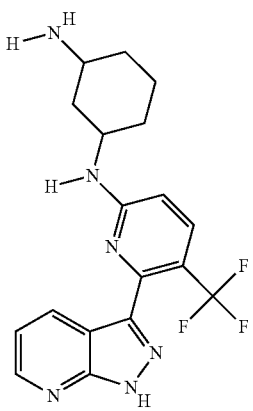 30
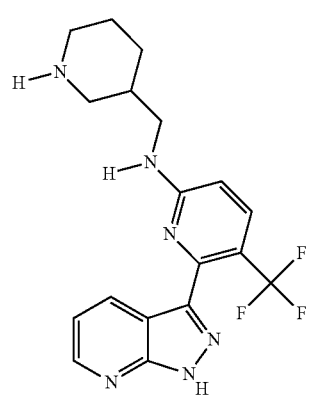 31
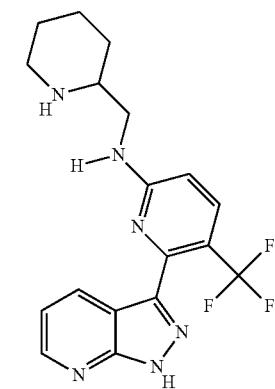 32
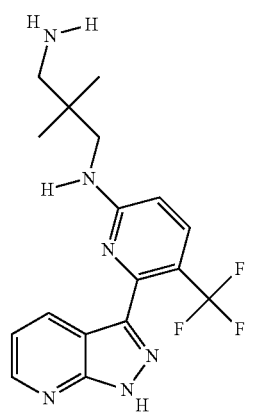 33

TABLE 1-continued
34
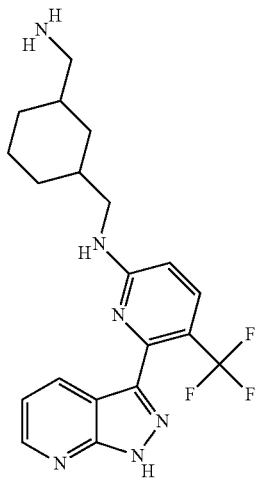
35
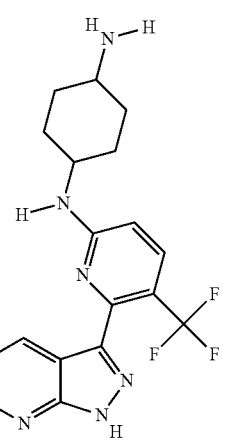
36
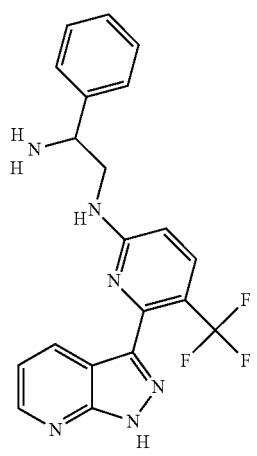
TABLE 1-continued
37
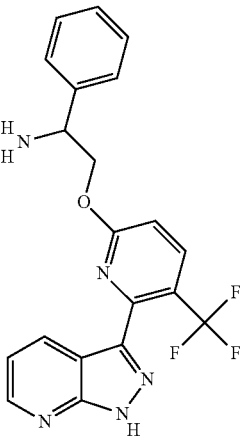
38
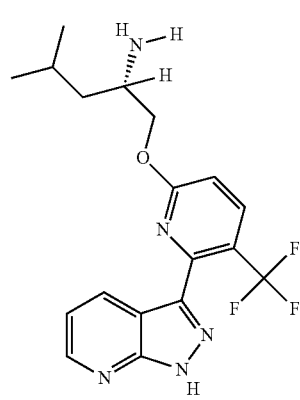
39
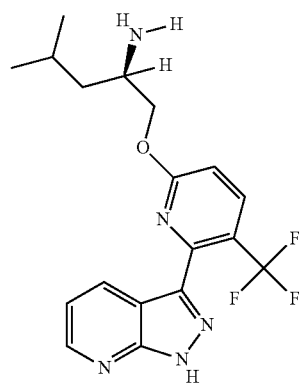
40
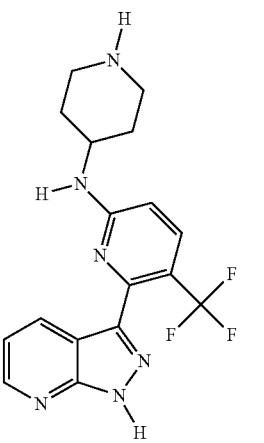 [SMILES: FC(F)(F)c1ccc(NC2CCNCC2)nc1-c1n[nH]c2ncccc12]

TABLE 1-continued
| 41 | 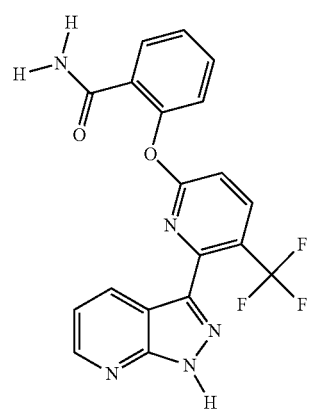 [SMILES: NC(=O)c1ccccc1Oc1ccc(C(F)(F)F)c(-c2n[nH]c3ncccc23)n1] |
| 42 | 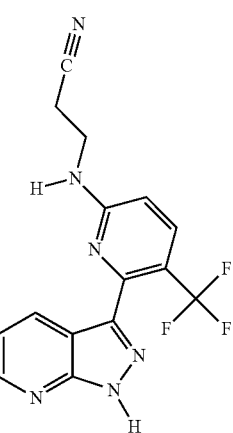 |
| 43 | 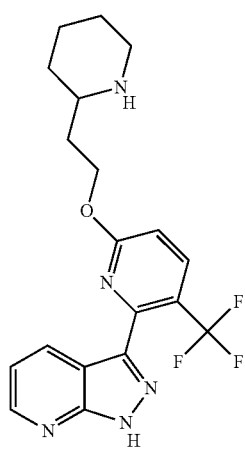 |
TABLE 1-continued
| 44 | 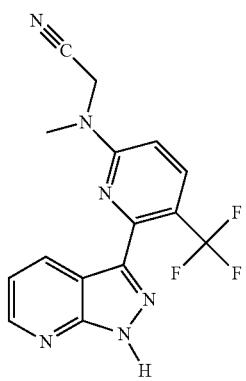 [SMILES: CN(CC#N)c1ccc(C(F)(F)F)c(-c2n[nH]c3ncccc23)n1] |
| 45 | 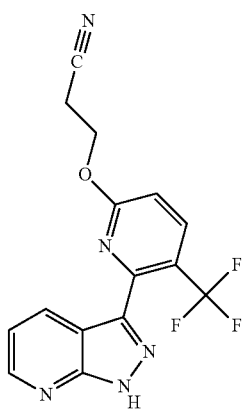 |
| 46 | 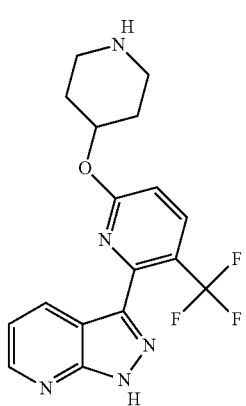 |
| 47 | |

TABLE 1-continued
| | |
|---|---|
| 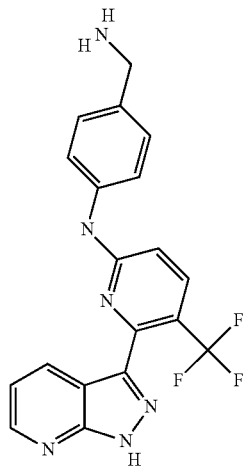 48 | 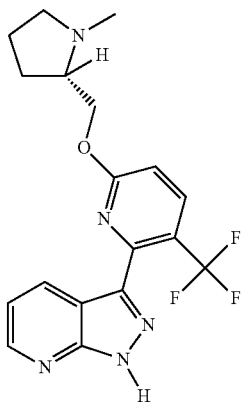 [SMILES: CN1CCC[C@H]1COc1ccc(C(F)(F)F)c(-c2n[nH]c3ncccc23)n1] 51 |
| 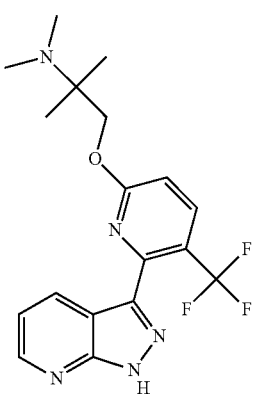 49 | 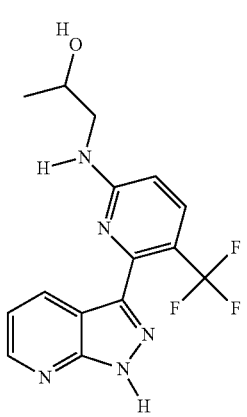 52 |
| | 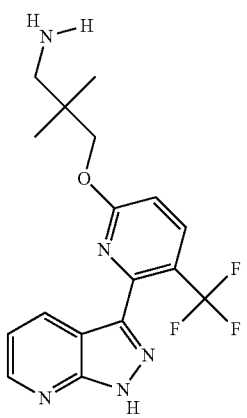 53 |
| 50 | 54 |

TABLE 1-continued
| | |
|---|---|
| 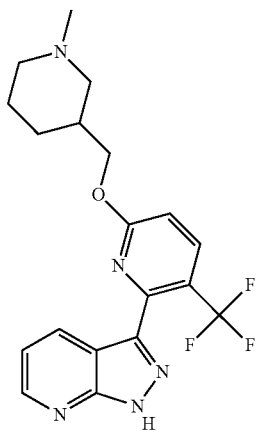 | 55 |
| 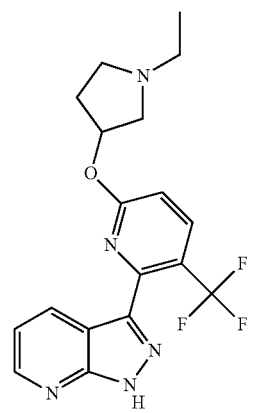 | 56 |
| 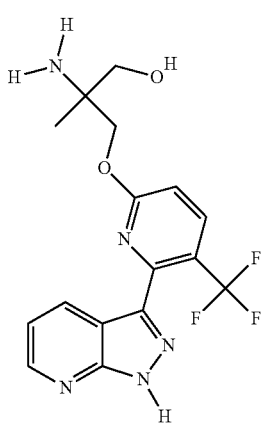 | 57 |
| 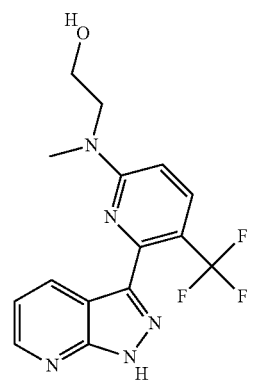 | 58 |
TABLE 1-continued
| | |
|---|---|
| 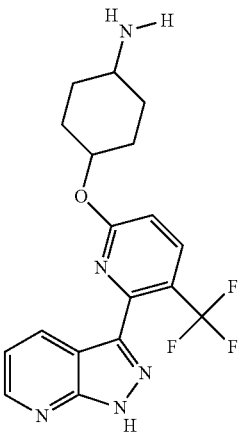 | 59 |
| 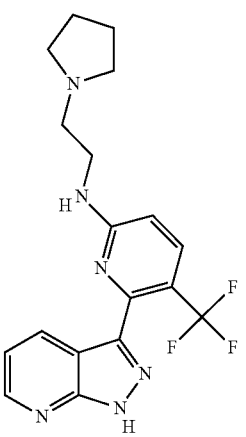 | 60 |
| 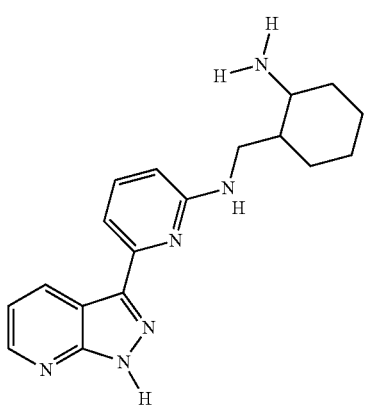 | 61 |
| 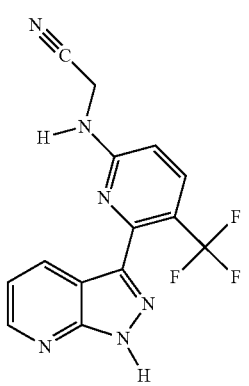 [SMILES: N#CCNc1ccc(C(F)(F)F)c(-c2n[nH]c3ncccc23)n1] | 62 |

TABLE 1-continued
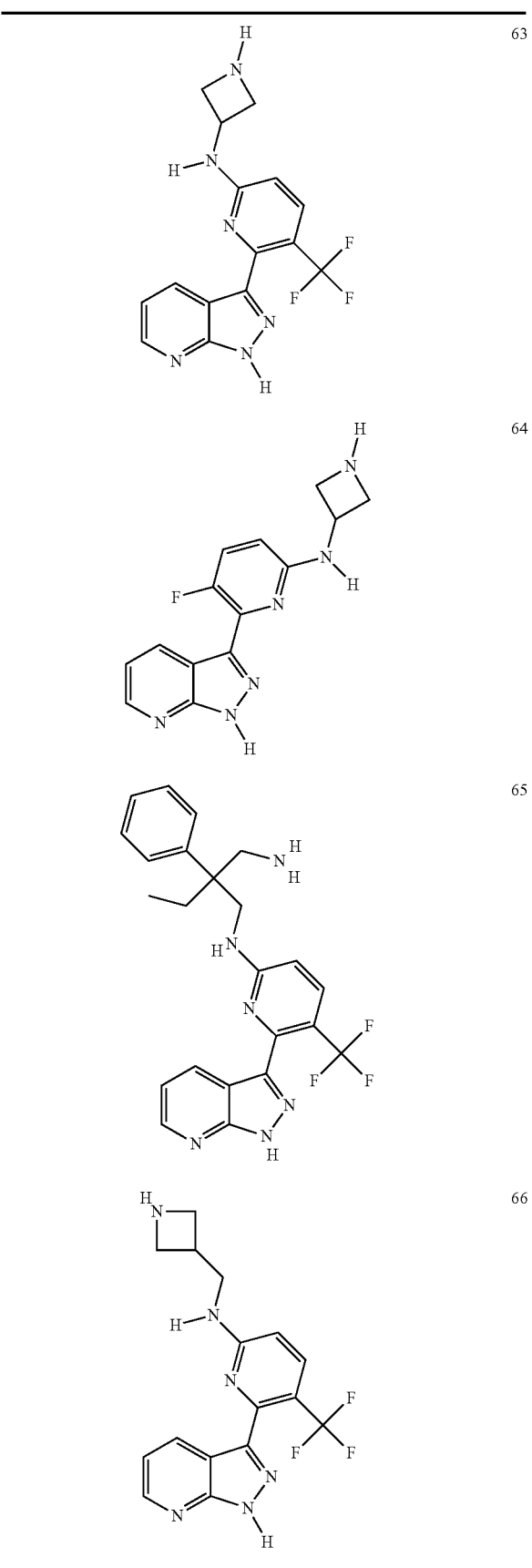
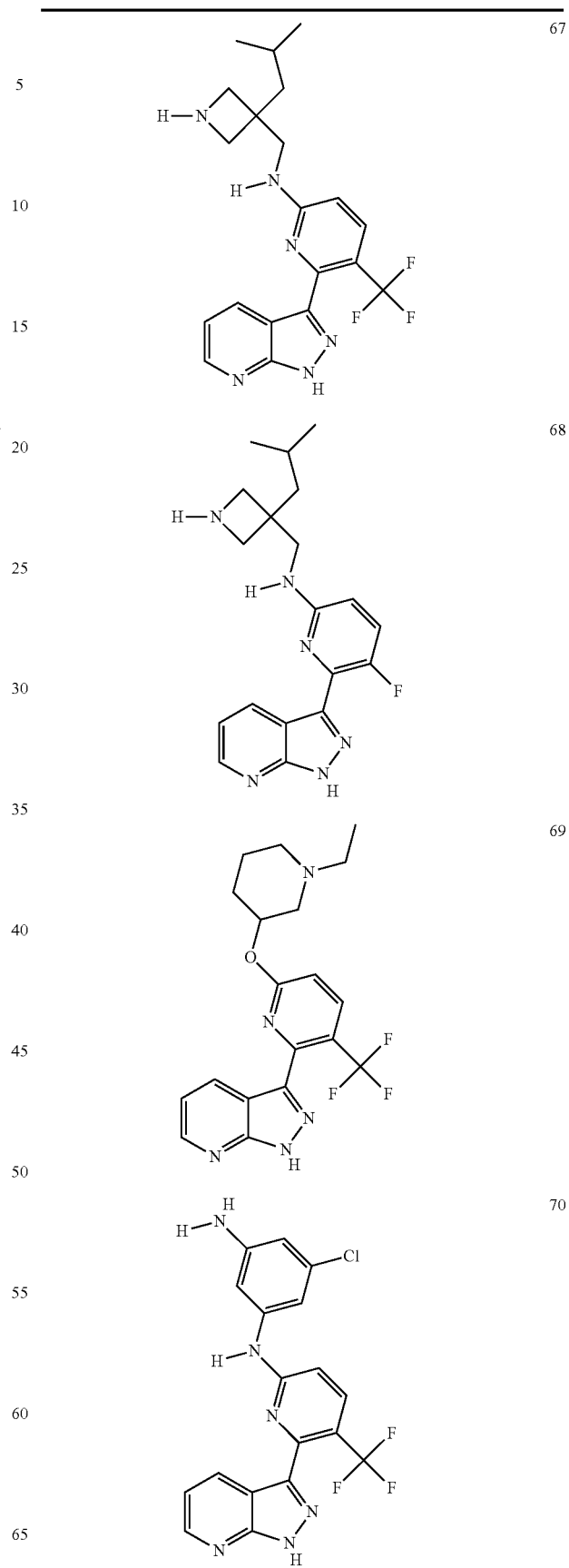

TABLE 1-continued
| | |
|---|---|
| 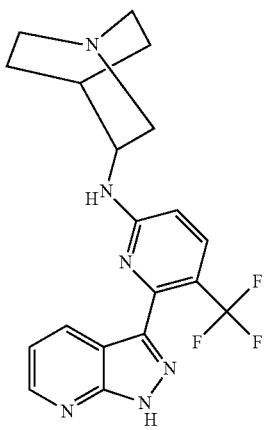 71 | 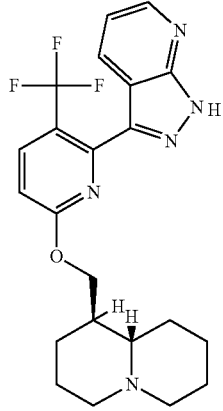 74 |
| 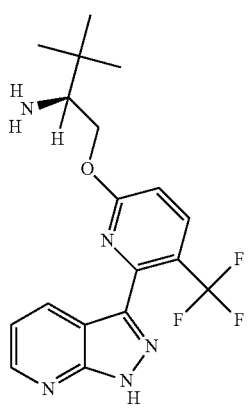 72 | 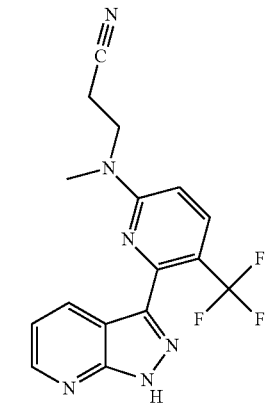 75 |
| 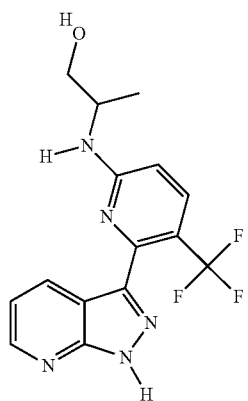 73 | 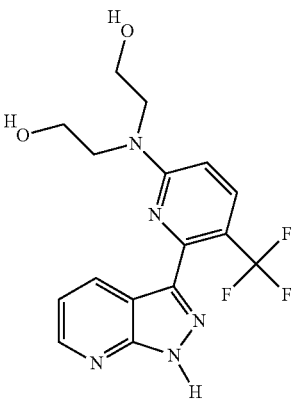 76 |

TABLE 1-continued
77 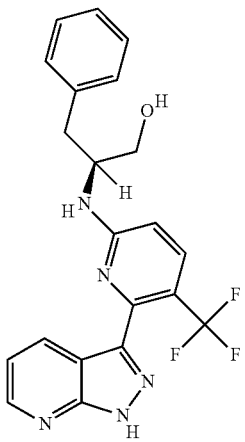
78 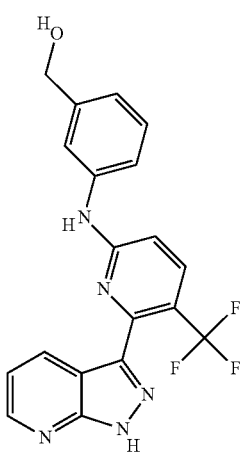
79 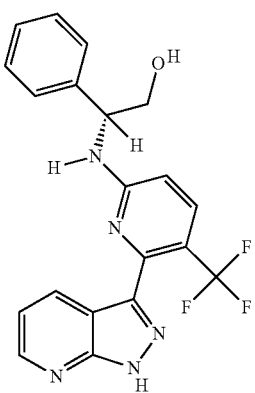
TABLE 1-continued
80 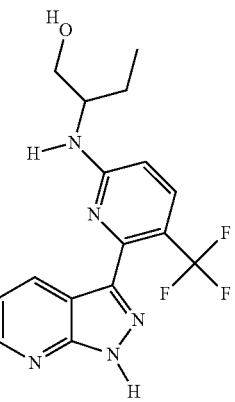
81 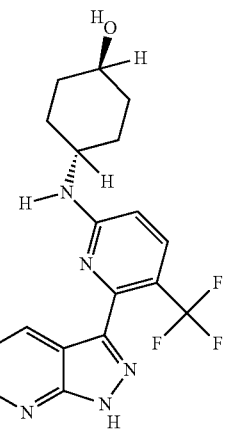
82 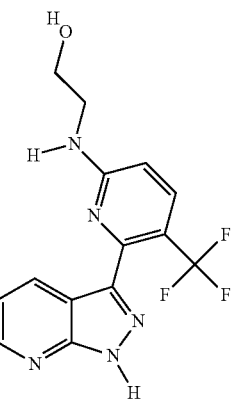
83 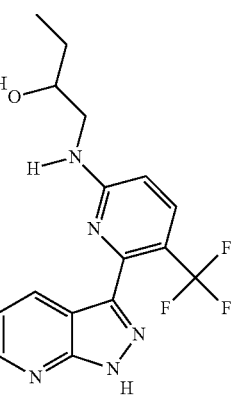

TABLE 1-continued

| | |
|---|---|
| 84 | 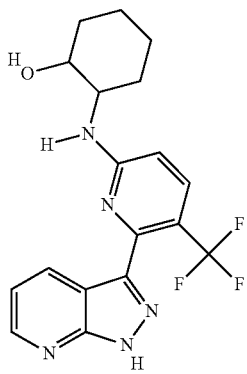 |
| 85 | 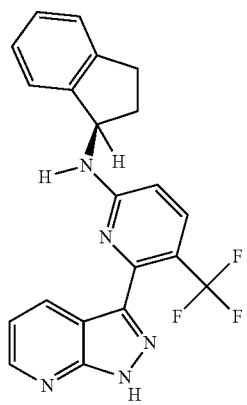 |
| 86 | 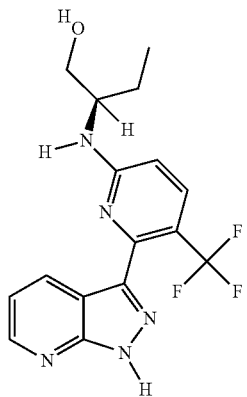 |

General Synthetic Methodology

The compounds of this invention may be prepared in light of the specification using steps generally known to those of ordinary skill in the art. Those compounds may be analyzed by known methods, including but not limited to LCMS (liquid chromatography mass spectrometry) HPLC and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein.
General Schemes:

EXAMPLES

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture. Method A: Column gradient conditions were 5%-100% acetonitrile-methanol over 3.5 mins gradient time and 4.8 mins run time on an ACE5C8 3.0×75 mm column. Flow rate was 1.2 ml/min. Method B: Column gradient were 5%-100% acetonitrile-methanol over 10 mins gradient time and 12 mins run time on a ACE5C8 4.6×150 mm column. Flow rate was 1.5 mL/min. As used herein, the term "Rt(min)" refers to the LCMS retention time, in minutes, associated with the compound. Unless otherwise indicated, the LCMS method utilized to obtain the reported retention time is as detailed above. If the Rt(min) is <5 min method A was used, if the Rt(min) is >5 min then method B was used.

1H-NMR spectra were recorded at 400 MHz using a Bruker DPX 400 instrument.

The following compounds of formula I, II or III can be prepared and analyzed as follows:

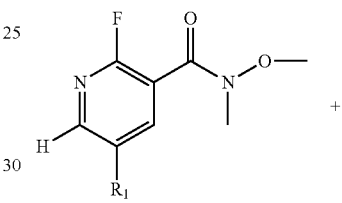

A

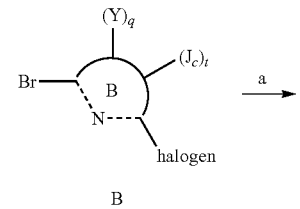

B

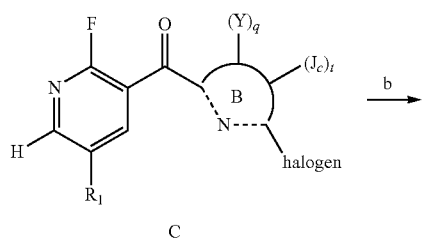

C

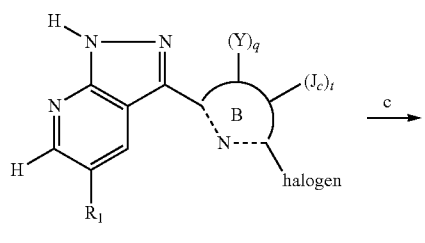

D

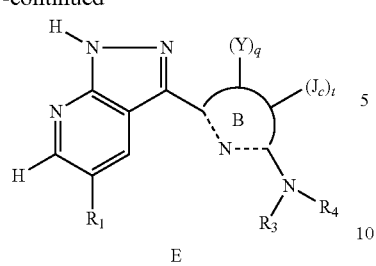

Reagents and conditions: a) n-BuLi or Grignard reagent, −78° C. to 0° C., THF; b) NH2NH2, THF, 80° C.; c) i. TrCl, NaH in DMF; ii. K2CO3, DMF, 110° C. or Pd(OAc)2, NaOtBu, DME, ligand, 90° C.; iii. TFA, Et3SiH, DCM.

Scheme I above shows a general route for the preparation of compounds of formula E, wherein the variables, are as defined herein. The weinreb amide A is couple with compound B in the presence of n-butyl lithium or Grignard reagent to form a compound of formula C. Compound C is then heated in the presence of hydrazine to yield intermediate D. The compound of formula D displaced by an optionally protected amine in the presence of suitable base, such as, potassium carbonate, diisopropylethylamine (DIPEA), triethylamine, 1,8-diazabicyclo[5.4.0]undec-7-ene (DBU) etc., in a suitable solvent, such as for example, dimethylformamide, dimethylsulfoxide (DMSO), n-butanol (n-Bu-OH) etc., at about 70° C. to about 110° C., about 80° C. to about 100° C., about 90° C. to about 100° C. to form an amine substituted heteroaroyl pyrazolopyridine. Alternatively the displacement can be perform using Buchwall type condition using Pd as catalyst and a series of bases and ligands well known by those skilled in the art. Subsequently, acidic conditions are used to remove the protenting groups to yield the desired compound E.

Example 1

N-((4-aminocyclohexyl)methyl)-6-(1H-pyrazolo[3,4-b]pyridin-3-yl)pyridin-2-amine

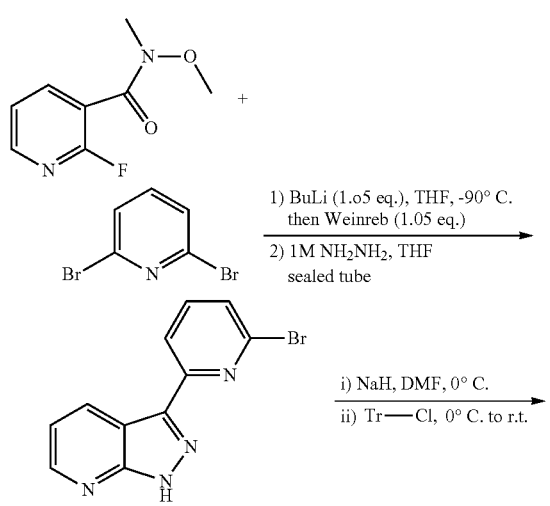

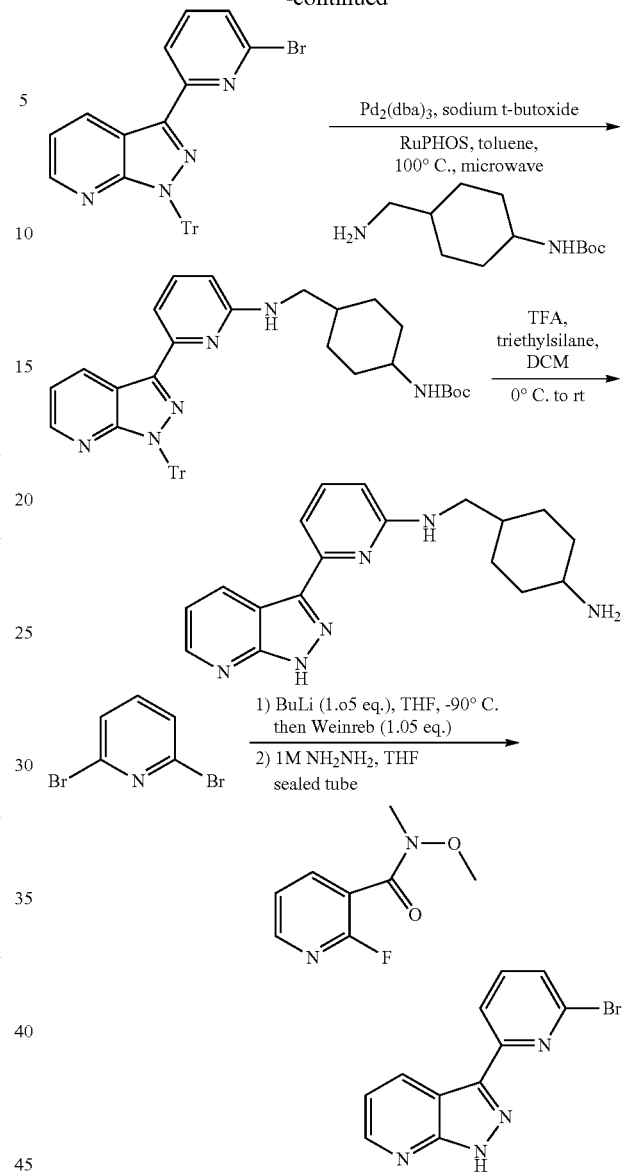

3-(6-bromopyridin-2-yl)-1H-pyrazolo[3,4-b]pyridine

A 2.5M BuLi solution in hexane (55 ml, 131 mmol, 1.05 eq.) was added dropwise over 20 minutes to a grey suspension of dibromopyridine (31 g, 137 mmol, 1 eq) in THF (300 ml), cooled to T<−90° C. under N2 (liq.N₂/Et2O bath). Temperature was kept at −95° C.<T<−90° C. during the addition. Before the end of the addition, the suspension turned into a straw yellow coloured solution. It was stirred at T<−90° C. for 10 min. A solution of the Weinreb (25 g, 137 mmol, 1.05 eq.) derivative in THF (20 ml) was added dropwise over 15 min. It was stirred at −90° C. for 1 h. The reaction mixture was quenched at −90° C. with a saturated NH₄Cl aqueous solution (20 ml). The reaction mixture was diluted with diethyl ether (400 ml) and washed with a saturated sodium bicarbonate aqueous solution (100 ml) and brine (100 ml). The organic layer was dried over magnesium sulfate and concentrated in vacuo. The yellow solid obtained was triturated in a PE/Et₂O (8-2) mixture and filtered. The residue was taken up in a solution of 1M hydrazine in THF (~250 ml) and stirred in a sealed tube at 80° C. overnight. A solid had precipitated and was filtered off (filtrate 1). The solid was triturated in methanol and filtered off (solid 1). The filtrate 1 was concentrated, triturated in methanol and filtered off to give solid 2. All remaining filtrates were concentrated and a solid was triturated in MeOH and filtered off (solid 3).

The solids were combined and dried in vacuo to afford 23 g of product. (off white powder; yield: 63%) 1H NMR (DMSO-d6) 7.36-7.39 (1H, m), 7.65-7.67 (1H, d), 7.87-8.91 (1H, t), 8.19-8.24 (1H, m), 8.61-8.63 (1H, m), 8.76-8.79 (1H, d). MS (ES+) 276 [MH+].

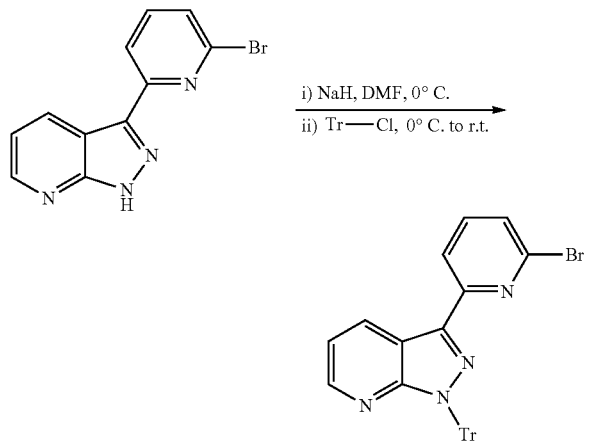

3-(6-bromopyridin-2-yl)-1-trityl-1H-pyrazolo[3,4-b]pyridine

A stirred suspension of 3-(6-bromo-2-pyridyl)-1H-pyrazolo[5,4-b]pyridine (3.00 g, 10.90 mmol) in dry DMF (30.00 mL) was cooled in an ice-bath. Sodium hydride (479.6 mg, 11.99 mmol) was added in one portion and the resulting mixture changed to a yellow solution and was stirred at 0° C. for 30 minutes. Trityl chloride (3.189 g, 11.44 mmol) was added in one portion and the resulting yellow suspension was stirred at RT for 60 minutes, by which time it was a bright yellow suspension. Analysis by LCMS showed presence of desired product.

The mixture was concentrated under reduced pressure to remove DMF to give a yellow solid. Trituration with DCM/MeOH gave the product as a pale yellow solid. The remaining filtrate was evaporated to dryness but further attempted triturations failed in cleaning the material so this was purified by column chromatography eluting with a 0-20% MeOH in DCM solvent system to give the desired product as a white solid (5.64 g, 79%). MS (ES+)=518.93. 1H NMR (400.0 MHz, DMSO) 7.39 (m, 16H), 7.69 (m, 1H), 7.85 (m, 2H), 8.45 (m, 1H), 8.75 (m, 1H).

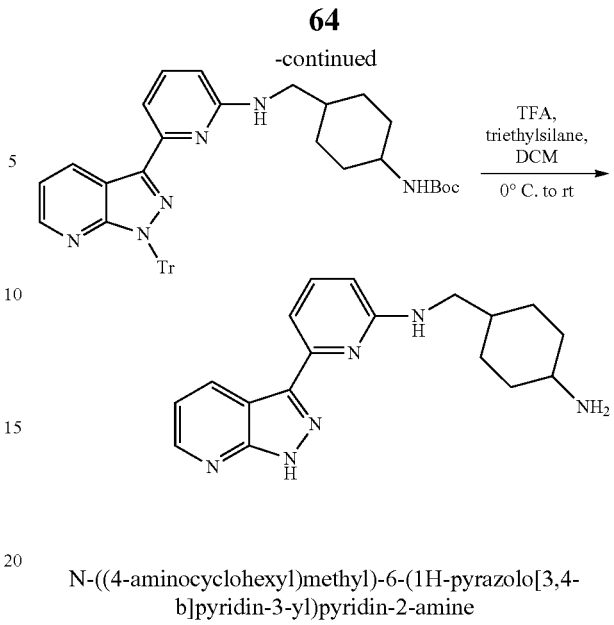

N-((4-aminocyclohexyl)methyl)-6-(1H-pyrazolo[3,4-b]pyridin-3-yl)pyridin-2-amine

To a stirred solution of 3-(6-bromo-2-pyridyl)-1-trityl-pyrazolo[5,4-b]pyridine (100 mg, 0.1933 mmol) and tert-butyl N-[4-(aminomethyl)cyclohexyl]carbamate (52.97 mg, 0.232 mmol) in DME (1.5 mL) was added Palladium acetate (4.340 mg, 0.01933 mmol) followed by dicyclohexyl-[2-(o-tolyl)phenyl]phosphane (7.046 mg, 0.01933 mmol) and sodium t-butoxide (27.87 mg, 0.2900 mmol). The reaction mixture was allowed to stir at 120 degrees in the microwave for 2 hours at which time consumption of the SM was observed. The mixture was diluted with DCM and filtered through a 2.5 g celite cartridge, combined washings were evaporated down to a smaller volume (5 ml) and the resultant solution was cooled to 0 degrees (with the aid of an ice bath) and treated with triethylsilane (0.4 mL, excess) followed by TFA (0.8 mL, excess). The reaction was allowed to stir at 0 degrees for 3 hours at which time LCMS analysis showed presence of product. The mixture was evaporated to dryness, taken up in DMSO and purified by the Fractionlynx system. Relavant fractions were collated together and filtered through a NaHCO3 cartridge to give the free base. The washings were evaporated to dryness, taken up in a small amount of MeCN/water and freeze-dried to give the required product as a white solid (19.5 mg, 31%).

MS (ES+)=323.12. 1H NMR (400.0 MHz, DMSO) d 0.92-1.07 (m, 4H), 1.61 (d, J=3.1 Hz, 1H), 1.77-1.86 (m, 4H), 2.48 (m, 1H), 3.22 (t, J=6.1 Hz, 2H), 6.45 (d, J=8.3 Hz, 1H), 6.74 (t, J=5.4 Hz, NH), 7.21-7.30 (m, 2H), 7.45 (t, J=7.8 Hz, 1H), 8.52 (dd, J=1.5, 4.5 Hz, 1H) and 8.92 (dd, J=1.4, 8.0 Hz, 1H) ppm.

Example 2

N1-(6-(1H-pyrazolo[3,4-b]pyridin-3-yl)pyridin-2-yl)-2-methylpropane-1,2-diamine (Compound 1)

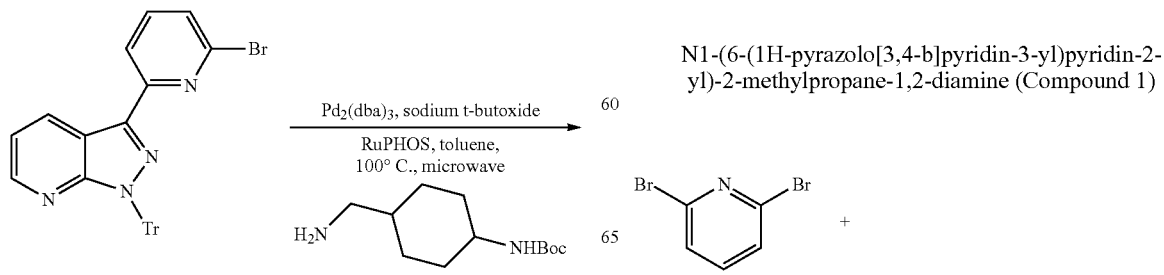

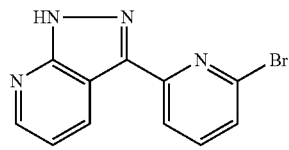 [SMILES: Brc1cccc(-c2n[nH]c3ncccc23)n1]

and concentrated under reduced pressure to give the required product as a white solid. Yield=9 g, 45%.

ES+ 282.85, 1H NMR (400.0 MHz, CDCl₃) d 7.35 (m, 1H), 7.71 (m, 1H), 7.80 (m, 1H), 8.05 (m, 1H), 8.21 (m, 1H) and 8.42 (m, 1H) ppm

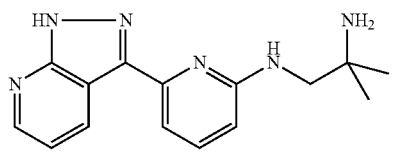 [SMILES: CC(C)(N)CNc1cccc(-c2n[nH]c3ncccc23)n1]

A mixture of (6-bromo-2-pyridyl)-(2-fluoro-3-pyridyl) methanone (10 g, 35.6 mmol) and 1M hydrazine in THF (39.14 ml, 39.14 mmol) was combined and stirred at 80° C. overnight in a sealed tube. A solid precipitated out and the mixture was allowed to cool and treated with a small amount of ⁱPropanol. The mixture was filtered to give the desired product as an off-white solid. Yield=7.0 g, 72%.

ES+ 276.87, 1H NMR (400.0 MHz, DMSO) d 7.36 (m, 1H), 7.67 (m, 1H), 7.90 (m, 1H), 8.20 (m, 1H), 8.61 (m, 1H) and 8.78 (m, 1H) ppm A mixture of 3-(6-bromo-2-pyridyl)-1H-pyrazolo[5,4-b] pyridine (50 mg,), potassium carbonate (150.6 mg, 1.09 mmol) and 2-methylpropane-1,2-diamine (40.1 mg, 0.45 mmol) in DMF (0.7 mL) was heated at 150° C. for 24 hours. The mixture was allowed to cool, filtered and the resultant filtrate purified by reverse phase preparative HPLC [Waters Sunfire C18, 10 uM, 100 A column, gradient 10%-95% B (solvent A: 0.05% TFA in water, solvent B: CH₃CN) over 16 minutes at 25 mL/min]. The fractions were collected, passed through a sodium bicarbonate cartridge and freeze-dried to give the title compound as a white solid (33.5 mg, 36% Yield).

ES+ 283

A 2.5M BuLi solution in hexane (30 ml, 75 mmol) was added dropwise over 20 minutes to a grey suspension of dibromopyridine (16.92 g, 71.43 mmol) in THF (300 ml), cooled to T<-90° C. under nitrogen. The temperature was maintained at -95° C.<T<-90° C. during the addition and then allowed to stir at T<90° C. for 30 minutes. A solution of the Weinreb derivative (13.81 g, 75 mmol) in THF (20 ml) was added dropwise over 15 minutes and the reaction mixture stirred at 90° C. for 1 hour. The mixture was quenched at ⁻90° C. with saturated NH₄Cl solution and diluted with diethyl ether, washed with saturated aqueous sodium bicarbonate and brine and dried over MgSO₄. The mixture was purified by flash chromatography (Companion; 330 g SiO2; Petroleum ether/EtOAc 0 to 50%). Relevant fractions were combined

Example 3

N-((4-aminocyclohexyl)methyl)-6-(1H-pyrazolo[3,4-b]pyridin-3-yl)-5-(trifluoromethyl)pyridin-2-amine (Compound 25)

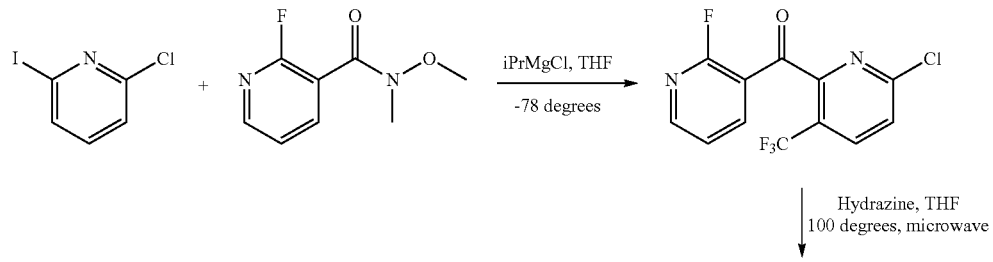

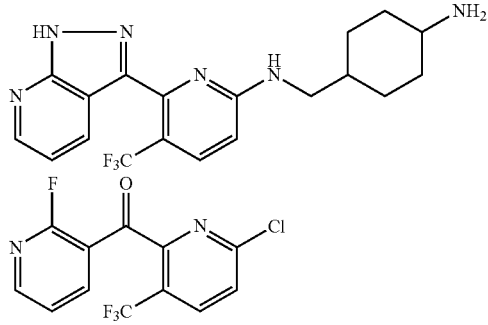
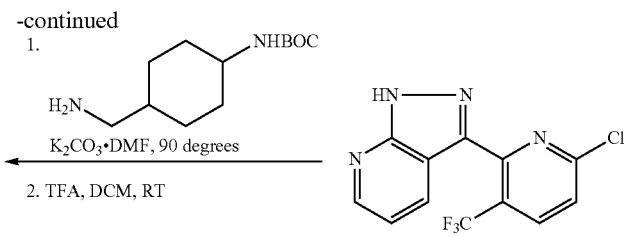

To a solution of 6-chloro-2-iodo-3-(trifluoromethyl)pyridine (2.2 g, 7.156 mmol) in THF (20.51 mL), cooled to −78° C., was added isopropyl magnesium chloride 2M in THF (3.649 mL of 2 M, 7.299 mmol) and the solution stirred for 15 mins. A solution of 2-fluoro-N-methoxy-N-methyl-pyridine-3-carboxamide (1.450 g, 7.872 mmol) in THF (4.631 mL) was added (over approx 1 min) and the resultant brown solution stirred at −78° C. for 1 hr. Reaction was quenched at −78° C. by addition of saturated NH₄Cl and diluted with ethyl acetate. Organic layer was washed with brine, dried (MgSO₄) and concentrated to give a yellow oil. Purified by column chromatography eluting with a 0-30% EtOAc/Pet ether system. Relavant fractions collated and evaporated to dryness to give the required product as a yellow oil. Yield=1.13 g, 52%.

ES+ 304.90, 1H NMR (400.0 MHz, CDCl₃) d 7.44 (m, 1H), 7.65 (m, 1H), 8.12 (m, 1H), 8.49 (m, 2H) ppm

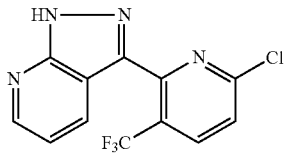 [SMILES: FC(F)(F)c1ccc(Cl)nc1-c1n[nH]c2ncccc12]

A solution of [6-chloro-3-(trifluoromethyl)-2-pyridyl]-(2-fluoro-3-pyridyl)methanone (224 mg, 0.7353 mmol) in THF (1.824 mL) was treated with hydrazine (1.0M in THF) (735.3 µL of 1 M, 0.7353 mmol), a bright yellow colour resulted which changed to a deep orange (no real temperature rise observed). The reaction was allowed to heat at 100 degrees for 3 hours and then concentrated in vacuo to give a yellow solid. Yield=207 mg, 90%.

ES+ 299.90, 1H NMR (400.0 MHz, CDCl₃) d 7.36 (m, 1H), 7.82 (m, 1H), 8.31 (m, 1H), 8.52 (m, 1H), 8.64 (m, 1H) ppm.

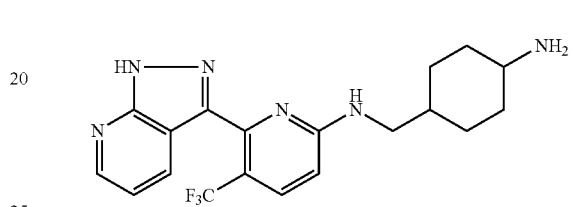

A mixture of 3-(6-chloro-3-(trifluoromethyl)pyridin-2-yl)-1H-pyrazolo[3,4-b]pyridine (100 mg, 0.33 mmol), K₂CO₃ (55.53 mg, 0.40 mmol) and tert-butyl N-[4-aminomethyl)cyclohexyl]carbamate (86.11 mg, 0.40 mmol) in DMF (1 mL) were heated at 115° C. for 8 hours. The reaction was worked up by diluting with DCM, washing with saturated aqueous bicarbonate and brine. After drying over MgSO4, the mixture was filtered and evaporated to dryness to give an orange residue. The residue was taken up in TFA/DCM (1 ml/3 ml) and stirred at RT for 2 hours. Reaction mixture was concentrated and the resultant residue was purified by reverse phase preparative HPLC [Waters Sunfire C18, 10 uM, 100 A column, gradient 10%-95% B (solvent A: 0.05% TFA in water, solvent B: CH₃CN) over 16 minutes at 25 mL/min]. The fractions were collected, passed through a sodium bicarbonate cartridge and freeze-dried to give the title compound as a white solid (29 mg, 17% Yield).

ES+ 391, 1H NMR (400.0 MHz, DMSO) d 1.01 (d, J=10.7 Hz, 2H), 1.21-1.30 (m, 2H), 1.56-1.59 (m, 1H), 1.84 (d, J=12.1 Hz, 4H), 2.95 (d, J=3.9 Hz, 1H), 3.31 (t, J=6.9 Hz, 2H), 6.62 (d, J=8.9 Hz, 1H), 7.28 (dd, J=4.5, 8.1 Hz, 1H), 7.53 (NH), 7.72 (NH2), 7.80 (d, J=8.9 Hz, 1H), 8.48 (d, J=7.6 Hz, 1H), 8.59 (dd, J=1.6, 4.4 Hz, 1H) and 13.94 (NH) ppm Table 2 below depicts data for Compounds 7-14, 18, 20-21, and 23 made in general by a similar route to that outlined in Example 1.

Table 2 below depicts data for Compounds 1-6, 16-17 61, 64, and 68 made in general by a similar route to that outlined in Example 2.

Table 2 below depicts data for Compounds 15, 19, 24-40, 41-60, 62, 63, 65, 66, 67, and 69-86 and made in general by a similar route to that outlined in Example 3.

TABLE 2

| No. | M + 1 (obs) | RT (min) | 1H-NMR |
|---|---|---|---|
| 1 | 283 | 5.99 | |
| 2 | 269 | 5.62 | |
| 3 | 309 | 6.72 | |
| 4 | 337 | 6.93 | |
| 5 | 283 | 6.4 | |

TABLE 2-continued

| No. | M + 1 (obs) | RT (min) | 1H-NMR |
|---|---|---|---|
| 6 | 281.07 | 2.47 | (DMSO) 1.40 (2H, m), 2.33 (1H, m), 3.44 (2H, m), 3.69 (1H, m), 3.72 (1H, m), 6.52 (1H, m), 7.27 (1H, m), 7.45 (1H, m), 7.69 (1H, m), 8.57 (1H, m) and 8.92 (1H, m) |
| 7 | 332.08 | 3.17 | 1H NMR (400.0 MHz, DMSO) d 3.41-3.48 (m, 1H), 3.71-3.76 (m, 1H), 4.85 (br s, 1H), 5.57 (br s, 1H), 6.56 (d, 1H), 6.83 (t, 1H), 7.20 (dd, 1H), 7.27 (t, 1H), 7.31-7.38 (m, 3H), 7.42 (d, 2H), 7.50 (t, 1H), 8.55 (dd, 1H) and 8.92 (d, 1H) ppm |
| 8 | 256 | 2.54 | 1H NMR (400.0 MHz, DMSO) d 3.47-3.51 (m, 2H), 3.63-3.68 (m, 2H), 4.77 (t, 1H), 6.51 (d, 1H), 6.68 (t, 1H), 7.28 (dd, 1H), 7.32 (d, 1H), 7.48 (t, 1H), 8.55 (dd, 1H), 8.93 (dd, 1H) and 13.75 (br s, 1H) ppm |
| 9 | 345.12 | 2.8 | 1H NMR (400.0 MHz, DMSO) d 2.85 (dd, 0.8H), 2.95-3.07 (m, 1.6H), 3.19-3.24 (m, 0.8H), 3.19-3.41 (masked signal, 3H), 3.63-3.70 (m, 2H), 6.44-6.48 (m, 1H), 6.65 (br s, 0.3H), 6.73 (t, 0.3 H), 6.83 (t, 0.7H), 7.09 (dd, 0.7 H), 7.16 (dd, 0.3 H), 7.22-7.41 (m, 6.6H), 7.44-7.49 (m, 1H), 8.53 (dd, 1H) and 8.84-8.89 (m, 1H) ppm |
| 10 | 297.11 | 2.55 | 1H NMR (400.0 MHz, DMSO) d 0.89 (d, 6H), 2.42 (s, 1H), 2.93 (d, 1H), 3.32-3.37 (masked signal, 4H), 6.53 (t, 1H), 6.67 (t, 1H), 6.80 (t, 0.4H), 7.27-7.34 (m, 2H), 7.46 (t, 1H), 8.53-8.55 (m, 1H) and 8.96-8.99 (m, 1H) ppm |
| 11 | 331.09 | 2.84 | 1H NMR (400.0 MHz, DMSO) d 3.33-3.39 (m, 3H), 3.66-3.72 (m, 1H), 4.18 (dd, 1H), 6.52 (d, 1H), 6.85 (t, 1H), 7.20 (dd, 1H), 7.23-7.27 (m, 1H), 7.32-7.37 (m, 3H), 7.44-7.51 (m, 3H), 8.55 (dd, 1H) and 8.95 (dd, 1H) ppm |
| 12 | 309.11 | 2.45 | 1H NMR (400.0 MHz, DMSO) d 1.37 (m, 3H), 1.57 (m, 1H), 1.81 (m, 2H), 2.25 (m, 2H), 2.78 (m, 1H), 3.01 (m, 1H), 3.22 (m, 1H), 6.46 (m, 1H), 6.72 (NH), 7.24 (NH), 7.30 (m, 2H), 7.46 (m, 1H), 8.52 (m, 1H) and 8.92 (m, 1H) ppm |
| 13 | 323.12 | 2.55 | 1H NMR (400.0 MHz, DMSO) d 0.92-1.07 (m, 4H), 1.61 (d, J = 3.1 Hz, 1H), 1.77-1.86 (m, 4H), 2.48 (m, 1H), 3.22 (t, J = 6.1 Hz, 2H), 6.45 (d, J = 8.3 Hz, 1H), 6.74 (t, J = 5.4 Hz, NH), 7.21-7.30 (m, 2H), 7.45 (t, J = 7.8 Hz, 1H), 8.52 (dd, J = 1.5, 4.5 Hz, 1H) and 8.92 (dd, J = 1.4, 8.0 Hz, 1H) ppm |
| 14 | 309.11 | 2.37 | 1H NMR (400.0 MHz, DMSO) d 1.08-1.11 (m, 2H), 1.71-1.76 (m, 3H), 2.37-2.43 (m, 2H), 2.94 (d, J = 11.6 Hz, 1H), 3.26 (t, J = 6.0 Hz, 2H), 4.11 (m 1H), 6.47 (d, J = 8.3 Hz, 1H), 6.76 (d, J = 5.3 Hz, NH), 7.23 (m, NH), 7.23-7.30 (m, 2H), 7.46 (t, J = 7.8 Hz, 1H), 8.53 (dd, J = 1.4, 4.4 Hz, 1H) and 8.93 (dd, J = 1.4, 8.0 Hz, 1H) ppm |
| 15 | 380.1 | 3.43 | 1H NMR (400.0 MHz, DMSO) d 0.81 (dd, 6H), 1.16-1.23 (m, 1H), 1.27-1.34 (m, 1H), 1.08-1.70 (m, 1H), 3.15-3.23 (m, 1H), 3.42-3.45 (br m, 1H), 3.71-3.74 (m, 1H), 4.70 (d, 1H), 6.68 (d, 1H), 7.26 (dd, 1H), 7.46 (br s, 1H), 7.79 (d, 1H), 8.47 (d, 1H), 8.57 (dd, 1H) and 13.90 (br s, 1H) ppm |
| 16 | 311.12 | 2.77 | 1H NMR (400.0 MHz, DMSO) d 0.82-0.91 (m, 6H), 1.18-1.34 (m, 2H), 1.79-1.85 (m, 1H), 2.97-3.10 (m, 2H), 3.33-3.50 (masked signal, 3H), 6.49-6.52 (m, 1H), 6.74 (t, 1H), 7.27 (dd, 1H), 7.31 (d, 1H), 7.45-7.50 (m, 1H), 8.53-8.56 (m, 1H) and 8.93-8.97 (m, 1H) ppm |
| 17 | 311.12 | 2.92 | 1H NMR (400.0 MHz, DMSO) d 0.80-0.94 (m, 6H), 1.39-1.46 (m, 2H), 1.70-1.77 (m, 1H), 2.70 (d, 2H), 4.10-4.32 (br s, 1H), 6.41 (d, 1H), 6.48 (d, 1H), 7.24-7.30 (m, 2H), 7.44-7.48 (m, 1H), 8.54 (dd, 1H) and 8.94-8.99 (m, 1H) ppm |
| 18 | 295.1 | 2.3 | 1H NMR (400.0 MHz, DMSO) d 1.28 (m, 3H), 1.86 (m, 2H), 2.51 (q, J = 1.8 Hz, 2H), 3.02 (m, 1H), 3.85 (NH), 4.09 (m, 1H), 6.39 (m, 1H), 6.51 (NH), 7.21 (m, 1H), 7.31 (m, 1H), 7.43 (m, 1H), 8.48 (m, 1H), 8.89 (m, 1H) and 13.71 (NH) ppm |
| 19 | 400.09 | 3.34 | 1H NMR (400.0 MHz, DMSO) d 3.40 (m, 1H), 3.68 (m, 1H), 4.78 (m, 1H), 5.56 (NH), 6.69 (m, 1H), 7.30 (m, 6H), 7.56 (NH), 7.77 (m, 1H), 8.48 (m, 2H) and 13.95 (NH) ppm |
| 20 | 295.05 | 2.54 | final NMR after column 1H NMR (400.0 MHz, DMSO) d 1.51 (m, 1H), 1.73 (m, 2H), 1.90 (m, 2H), 2.85-2.93 (m, 2H), 3.44 (m, 2H), 6.53 (d, J = 8.0 Hz, 1H), 6.78 (NH), 7.28-7.34 (m, 2H), 7.50 (t, J = 7.8 Hz, 1H), 8.55 (dd, J = 1.6, 4.5 Hz, 1H) and 8.91 (dd, J = 1.5, 8.0 Hz, 1H) ppm |

TABLE 2-continued

| No. | M + 1 (obs) | RT (min) | 1H-NMR |
|---|---|---|---|
| 21 | 312.12 | 3.34 | 1H NMR (400.0 MHz, DMSO) d 0.84 (d, 3H), 0.91 (d, 3H), 1.27-1.41 (m, 2H), 1.80-1.85 (m, 1H), 3.18-3.25 (m, 1H), 3.47-3.53 (m, 1H), 3.81 (br m, 1H), 4.69 (br s, 1H), 6.53 (d, 1H), 6.68 (t, 1H), 7.26 (dd, 1H), 7.31 (d, 1H), 7.47 (t, 1H), 8.54 (dd, 1H), 8.92 (dd, 1H) and 13.70 (br s, 1H) ppm |
| 22 | 295.1 | 2.35 | 1H NMR (400.0 MHz, DMSO) d 1.43 (m, 1H), 1.55(m, 1H), 1.95(m, 2H), 2.51(m, 1H), 2.67(m, 1H), 2.95(m, 1H) <3.05(m, 1H), 3.20(m, 1H), 6.46(m, 1H), 6.83(m, 1H), 7.26(m, 1H), 7.30 (2NH), 7.48(m, 1H), 8.51(m, 1H), 8.92(m, 1H) |
| 23 | 309.11 | 2.6 | 1H NMR (400.0 MHz, DMSO) d 1.12 (m, 1H), 1.28 (m, 2H), 1.49 (m, 1H), 1.70 (m, 2H), 2.76 (m, 1H), 3.00 (m, 1H), 3.25 (m, 1H), 4.11 (d, J = 5.3 Hz, 2H), 6.48 (m, 1H), 6.72 (NH), 7.31 (m, 2H), 7.48 (m, 1H), 8.55 (m, 1H), 8.96 (m, 1H) and 13.69 (NH) ppm |
| 24 | 405.18 | 3.04 | 1H NMR (400.0 MHz, DMSO) d 0.82 (d, J = 11.4 Hz, 1H), 1.33-1.43 (m, 5H), 1.79 (d, J = 12.2 Hz, 2H), 2.33-2.40 (m, 1H), 2.84 (s, 1H), 3.20 (s, 1H), 3.34 (4H), 6.59 (d, J = 8.9 Hz, 1H), 7.21-7.25 (m, 1H), 7.47 (d, J = 4.4 Hz, 1H), 7.76-7.80 (m, 1H), 8.49 (N H) and 8.55 (d, J = 4.0 Hz, 1H) ppm |
| 25 | 391.12 | 2.79 | 1H NMR (400.0 MHz, DMSO) d 1.01 (d, J = 10.7 Hz, 2H), 1.21-1.30 (m, 2H), 1.56-1.59 (m, 1H), 1.84 (d, J = 12.1 Hz, 4H), 2.95 (d, J = 3.9 Hz, 1H), 3.31 (t, J = 6.9 Hz, 2H), 6.62 (d, J = 8.9 Hz, 1H), 7.28 (dd, J = 4.5, 8.1 Hz, 1H), 7.53 (NH), 7.72 (NH2), 7.80 (d, J = 8.9 Hz, 1H), 8.48 (d, J = 7.6 Hz, 1H), 8.59 (dd, J = 1.6, 4.4 Hz, 1H) and 13.94 (NH) ppm |
| 26 | 363.05 | 2.68 | 1H NMR (400.0 MHz, DMSO) d 1.57 (m, 2H), 1.86 (m, 1H), 2.04 (m, 1H), 2.88 (m, 2H), 3.16 (m, 1H), 3.35 (m, 1H), 4.19 (m, 1H), 6.67 (m, 1H), 7.29 (m, 1H), 7.51 (m, 1H), 7.89 (m, 1H), 8.40 (NH), 8.52 (NH2), 8.58 (m, 1H) and 13.95 (NH) ppm |
| 27 | 377.07 | 2.68 | 1H NMR (400.0 MHz, DMSO) d 1.34 (d, J = 11.2 Hz, 2H), 1.89 (dd, J = 9.2, 12.8 Hz, 3H), 2.84 (dd, J = 12.4, 23.5 Hz, 2H), 3.19 (d, J = 12.5 Hz, 4H), 6.64 (d, J = 8.9 Hz, 1H), 7.29 (dd, J = 4.5, 8.1 Hz, 1H), 7.61 (NH), 7.82 (d, J = 8.9 Hz, 1H), 8.10 (NH), 8.48 (d, J = 7.6 Hz, 1H), 8.59 (dd, J = 1.5, 4.5 Hz, 1H) and 13.94 (NH) ppm |
| 28 | 363.08 | 2.68 | 1H NMR (400.0 MHz, DMSO) d 1.55-1.64 (m, 1H), 1.71-2.00 (m, 3H), 2.99-3.13 (m, 2H), 3.46-3.53 (m, 1H), 3.57-3.73 (m, 2H), 6.67 (d, J = 8.9 Hz, 1H), 7.22 (dd, J = 4.5, 8.1 Hz, 1H), 7.83 (d, J = 8.9 Hz, 1H), 8.36 (d, J = 8.0 Hz, 1H), 8.52 (dd, J = 1.5, 4.5 Hz, 1H) and 13.91 (NH) ppm |
| 29 | 363.08 | 2.75 | 1H NMR (400.0 MHz, DMSO) d 1.40 (m, 1H), 1.55 (m, 2H), 1.95 (m, 2H), 2.35 (m, 1H), 2.67 (d, J = 1.8 Hz, 1H), 2.97 (m, 1H), 3.15 (d, J = 9.1 Hz, 1H), 6.62 (d, J = 8.9 Hz, 1H), 7.21-7.27 (m, 1H), 7.56 (m, 1H), 7.78-7.82 (m, 1H) and 8.55 (d, J = 4.3 Hz, 1H) ppm |
| 30 | 377.12 | 2.87 | 1H NMR (400.0 MHz, DMSO) d 1.05 (m, 2H), 1.25 (m, 1H), 1.73 (m, 2H), 2.10 (m, 2H), 2.65 (m, 1H), 3.10 (m, 1H), 3.80 (1H, m), 6.55 (d, J = 8.9 Hz, 1H), 7.22 (m, 1H), 7.77 (d, J = 9.0 Hz, 1H), 8.45 (m, 1H) and 8.54 (d, J = 5.6 Hz, 1H) ppm |
| 31 | 377.12 | 2.75 | 1H NMR (400.0 MHz, DMSO) 1.05 (m, 1H), 1.39 (m, 1H), 1.76 (m, 2H), 1.86 (m, 1H), 2.49 (qn, J = 1.7 Hz, 3H), 3.02 (m, 3H), 6.44 (d, J = 8.9 Hz, 1H), 7.09 (dd, J = 4.5, 8.1 Hz, 1H), 7.41 (NH), 7.65 (m, 1H), 8.26 (m, 1H), 8.39 (dd, J = 1.5, 4.5 Hz, 1H) and 13.75 (NH) ppm |
| 32 | 377.07 | 2.72 | 1H NMR (400.0 MHz, DMSO) 1.41 (m, 4H), 1.77 (m, 3H), 2.84 (m, 1H), 3.45 (m, 2H), 3.60 (m, 1H), 6.73 (d, J = 8.8 Hz, 1H), 7.29 (m, 1H), 7.64 (NH), 7.91 (d, J = 8.9 Hz, 1H), 8.44 (m, 1H) 8.60 (m, 1H) and 13.97 (NH) ppm |
| 33 | 365.07 | 2.85 | 1H NMR (400.0 MHz, DMSO) d 0.97 (s, 6H), 2.81 (m, 2H), 3.33-3.35 (m, 2H), 6.76 (d, J = 8.9 Hz, 1H), 7.31 (m, 1H), 7.64 (NH), 7.86 (d, J = 9.0 Hz, 1H), 8.45 (m, 1H), 8.60 (dd, J = 1.5, 4.5 Hz, 1H) and 13.98 (NH) ppm |
| 34 | 405.12 | 3.1 | 1H NMR (400.0 MHz, DMSO) 0.67 (m, 1H), 0.90 (m, 2H), 1.21 (m, 1H), 1.39 (m, 3H), 1.74 (m, 3H), 2.52 (m, 2H), 3.17 (m, 2H), 6.61 (m, 1H), 7.33 (m, 1H), 7.51 (NH), 7.69 (NH), 7.84 (m, 1H), 8.47 (m, 1H), 8.62 (m, 1H) and 13.94 (NH) ppm |

TABLE 2-continued

| No. | M + 1 (obs) | RT (min) | 1H-NMR |
|---|---|---|---|
| 35 | 377.09 | 2.84 | 1H NMR (400.0 MHz, DMSO) 1.39 (m, 4H), 2.03 (m, 4H), 2.81 (m, 1H), 3.75 (m, 1H), 6.61 (m, 1H), 7.30 (m, 1H), 7.43 (NH), 7.70 (NH), 7.76 (m, 1H), 8.50 (m, 1H), 8.60 (m, 1H) and 13.94 (NH) ppm |
| 36 | 399.08 | 3.17 | 1H NMR (400.0 MHz, DMSO) 1.98 (m, 1H), 3.60 (m, 1H), 4.10 (m, 1H), 6.61 (m, 1H), 7.22 (d, J = 7.0 Hz, 4H), 7.38 (d, J = 7.5 Hz, 2H), 7.57 (NH), 7.83 (m, 1H), 8.55 (m, 2H), and 13.922 (NH) ppm |
| 37 | 400.08 | 3.37 | 1H NMR (400.0 MHz, DMSO) 4.31 (m, 1H), 4.41 (m, 1H), 4.49 (m, 1H), 7.00 (m, 1H), 7.22 (m, 2H), 7.32 (m, 2H), 7.45 (d, J = 7.2 Hz, 2H), 8.21 (m, 1H) and 8.50 (m, 2H) ppm |
| 38 | 380.1 | 3.25 | 1H NMR (400.0 MHz, DMSO) d 0.86 (dd, J = 6.6, 12.8 Hz, 6H), 1.25 (m, 2H), 1.82 (m, 1H), 3.08 (m, 1H), 4.13 (m, 1H), 4.29 (m, 1H), 7.05 (d, J = 8.8 Hz, 1H), 7.30 (m, 1H), 8.21 (d, J = 8.9 Hz, 1H), 8.51 (m, 1H) and 8.53-8.55 (m, 1H) ppm |
| 39 | 380.1 | 3.22 | 1H NMR (400.0 MHz, DMSO) d 0.82 (dd, J = 6.6, 12.6 Hz, 6H), 1.18-1.26 (m, 2H), 1.75-1.79 (m, 1H), 3.04-3.08 (m, 1.H), 4.11 (dd, J = 6.8, 10.2 Hz, 1H), 4.27 (dd, J = 4.9, 10.2 Hz, 1H), 7.02 (d, J = 8.8 Hz, 1H), 7.29 (dd, J = 4.5, 8.1 Hz, 1H), 8.18 (d, J = 8.9 Hz, 1H), 8.50 (dd, J = 1.5, 8.1 Hz, 1H) and 8.57 (dd, J = 1.5, 4.5 Hz, 1H) ppm |
| 40 | 363.05 | 2.67 | 1H NMR (400.0 MHz, CDCl3/MeOH) d 1.62 (m, 2H), 2.00 (d, J = 12.8 Hz, 2H), 2.78 (m, 2H), 3.05 (t, J = 1.4 Hz, 1H), 3.19 (d, J = 12.6 Hz, 2H), 3.94 (s, 1H), 6.42 (d, J = 8.8 Hz, 1H), 7.03 (dd, J = 4.6, 8.0 Hz, 1H), 7.52 (d, J = 8.9 Hz, 1H), 8.05 (d, J = 8.0 Hz, 1H) and 8.33 (d, J = 4.2 Hz, 1H) ppm |
| 41 | | | 14.15 (s, 1H), 11.78 (s, 1H), 11.32 (s, 1H), 8.61 (m, 2H), 8.41 (dd, 2H), 7.99 (dd, 1H), 7.46 (t, 1H), 7.30 (dd, 1H), 7.02 (dd, 2H) |
| 42 | | | |
| 43 | | | |
| 44 | | | |
| 45 | | | |
| 46 | | | 14.15 (s, 1H), 8.59 (dd, 1H), 8.51 (dd, 1H), 8.21 (d, 1H), 7.30 (dd, 1H), 7.05 (d, 1H), 4.39 (dd, 1H), 4.27 (dd, 1H), 3.37 (d, 1H), 3.25 (d, 1H), 2.79 (dd, 2H), 2.33-2.22 (br, 1H), 1.81 (d, 2H), 1.63 (m, 1H), 1.35 (m, 1H) |
| 47 | | | 13.90 (s, 1H), 8.55 (dd, 1H), 8.47 (dd, 1H), 7.75 (d, 1H), 7.25 (dd, 1H), 6.74 (d, 1H), 3.37(s, 2H), 1.53-1.32 (m, 10H) |
| 48 | | | |
| 49 | | | 9.17 (s, 1H), 8.62 (d, 1H), 8.58 (dd, 1H), 8.31 (dd, 1H), 8.04 (d, 1H), 7.71 (d, 1H), 7.62 (dd, 1H), 7.20 (dd, 1H), 7.04 (d, 1H) |
| 50 | | | 8.59 (dd, 1H), 8.42 (dd, 1H), 8.10 (d, 1H), 7.29 (dd, 1H), 7.25 (d, 1H), 7.14 (d, 1H), 6.59 (d, 1H) |
| 51 | | | 14.08 (br, 1H), 8.57 (dd, 1H), 8.50 (dd, 1H), 8.17 (d, 1H), 7.29 (dd, 1H), 7.01 (d, 1H), 4.43 (dd, 1H), 4.29 (dd, 1H), 2.94 (m, 1H), 2.63 (m, 1H), 2.31 (s, 3H), 2.20 (dd, 1H), 1.92 (m, 1H), 1.72-1.54 (m, 3H) |
| 52 | | | 14.06 (br, 1H), 8.58 (dd, 1H), 8.49 (dd, 1H), 8.19 (d, 1H), 7.31 (dd, 1H), 7.05 (d, 1H), 4.35 (s, 2H), 2.30 (s, 6H), 1.14 (s, 6H) |
| 53 | | | 13.86 (br, 1H), 8.54 (dd, 1H), 8.47 (dd, 1H), 7.76 (d, 1H), 7.37 (br, 1H), 7.25 (dd, 1H), 6.65 (d, 1H), 4.72 (br, 1H), 3.83 (m, 1H), 3.30 (m, 2H), 1.08 (d, 3H) |
| 54 | | | |
| 55 | | | |
| 56 | | | |
| 57 | | | |
| 58 | | | |
| 59 | | | |
| 60 | | | |
| 61 | 309.11 | 2.5 | 1H NMR (400.0 MHz, DMSO) d 1.02 (m, 3H), 1.39 (m, 1H), 1.78 (m, 2H), 2.10 (m, 2H), 2.74 (m, 1H), 3.84 (m, 1H), 6.44 (m, 1H), 6.57 (NH), 7.29 (m, 2H), 7.44 (m, 1H), 8.55 (m, 1H) and 8.89 (m, 1H) ppm |
| 62 | 319 | 2.9 | (400 MHz, DMSO) 4.45 (2H, d), 6.81 (1H, d), 7.28 (1H, dd), 7.98 (1H, d), 8.07 (1H, t), 8.59-8.65 (2H, m), 14.02 (1H, brs). |
| 63 | 335 | 2.62 | (d6-DMSO, 400 MHz) 3.91-4.00 (2H, m), 4.16-4.19 (2H, m), 4.86-4.91 (1H, m), 6.71 (1H, d), 7.30 (1H, dd), 7.93 (1H, d), 8.19 (1H, d), 8.46 (1H, d), 8.60 (1H, dd), 8.77 (2H, br s), 14.00 (1H, s) |

TABLE 2-continued

| No. | M + 1 (obs) | RT (min) | 1H-NMR |
|---|---|---|---|
| 64 | 285 | 2.42 | |
| 65 | 441 | 3.32 | (d6-DMSO, 400 MHz) 0.58 (3H, t), 1.75-1.81 (2H, m), 3.21 (2H, brs), 3.86 (2H, m), 6.78 (1H, d), 7.27-7.32 (2H, m), 7.37-7.10 (5H, m), 7.63 (3H, br s), 7.86 (1H, d), 8.46 (1H, d), 8.60 (1H, dd) |
| 66 | 349 | 2.72 | (d6-DMSO, 400 MHz) 3.04-3.11 (1H, m), 3.57-3.60 (2H, m), 3.70-3.77 (2H, m), 3.91-3.98 (2H, m), 6.65 (1H, d), 7.29 (1H, dd), 7.66 (1H, t), 7.86 (1H, d), 8.42 (1H, d), 8.51 (2H, brs), 8.59 (1H, dd), 13.96 (1H, s) |
| 67 | 405 | 3.18 | (d6-DMSO, 400 MHz) 0.75 (6H, d), 1.64 (2H, d), 1.68-1.74 (1H, m), 3.61-3.70 (4H, brm), 3.84-3.89 (2H, m), 6.76 (1H, d), 7.27 (1H, dd), 7.61 (1H, t), 7.88 (1H, d) 8.36 (1H, d), 8.53 (2H, brs), 8.59 (1H, dd), 13.93 (1H, s) |
| 68 | 355 | 2.9 | (d6-DMSO, 400 MHz)0.85 (6H, d), 1.70 (2H, d), 1.76-1.82 (1H, m), 3.64-3.71 (4H, m), 3.90-3.96 (2H, m), 6.67 (1H, dd), 6.90 (1H, t), 7.28 (1H, dd), 7.57 (1H, dd), 8.54 (2H, br s), 8.60 (1H, dd), 8.68 (1H, dd), 13.93 (1H, brs) |
| 69 | | | |
| 70 | | | |
| 71 | | | |
| 72 | | | |
| 73 | | | |
| 74 | | | |
| 75 | | | 8.57 (d, 1H), 8.44 (d, 1H), 7.96 (d, 1H), 7.27 (dd, 1H), 6.88 (d, 1H), 3.94 (t, 2H), 2.84 (t, 2H). |
| 76 | | | 13.85(s, 1H), 8.55 (d, 1H), 8.40 (d, 1H), 7.23 (dd, 1H), 6.81 (d, 1H), 4.83 (s, 2H), 3.66 (d, 4H), 3.61 (t, 4H), 3.15 (s, 4H), 2.47(d, 1H). |
| 77 | | | 8.55 (d, 1H), 7.72 (s, 1H), 7.25 (d, 1H), 7.22 (s, 15H), 7.12 (d, 1H), 4.85 (t, 1H), 3.38 (s, 2H), 2.49 (m, 1H), 2.47(m, 1H). |
| 78 | | | 9.68 (s, 1H), 8.58 (d, 1H), 8.43 (d, 1H), 8.01 (d, 1H), 7.64 (s, 1H), 7.49 (d, 1H), 7.23 (m, 3H), 6.94(m, 2H), 5.10(s, 1H), 4.38(s, 2H). |
| 79 | | | 13.85 (s, 1H), 8.48 (d, 1H), 7.90 (d, 1H), 7.78 (d, 1H), 7.34 (m, 4H), 7.25 (m, 1H), 7.15 (s, 1H), 7.03 (m, 1H), 7.02(s, 2H), 6.98(s, 1H), 5.01(s, 1H), 3.64(m, 2H), 3.44(s, 1H). |
| 80 | | | 13.91 (s, 1H), 8.53 (d, 1H), 8.45 (d, 1H), 7.74 (d, 1H), 7.37 (s, 1H), 7.35 (m, 2H), 7.23 (s, 1H), 6.62 (d, 1H), 6.62(d, 1H), 4.76 (s, 1H), 3.49 (s, 1H), 3.44 (m, 3H), 1.65 (m, 1H), 1.45 (m, 1H), 0.88 (t, 3H). |
| 81 | | | 13.91 (s, 1H), 8.55 (d, 1H), 8.48 (d, 1H), 7.74 (d, 1H), 7.26 (m, 2H), 6.54 (d, 1H), 4.55 (d, 1H), 3.42 (m, 1H), 3.33 (m, 1H), 1.96 (s, 2H), 1.84 (s, 2H), 1.26 (m, 4H). |
| 82 | | | 13.90 (s, 1H), 8.54 (d, 1H), 8.46 (d, 1H), 7.76 (d, 1H), 7.45 (s, 1H), 7.37 (s, 2H), 7.25 (m, 1H), 7.03 (s, 2H), 6.63 (d, 1H), 3.56 (m, 3H), 3.43 (d, 2H). |
| 83 | | | 13.92 (s, 1H), 8.53 (d, 1H), 8.47 (d, 1H), 7.75 (d, 1H), 7.44 (s, 1H), 7.23 (m, 4H), 6.66 (d, 1H), 4.79 (br, 2H), 3.57 (br, 1H), 3.43 (br, 1H), 3.21-3.27 (m, 1H), 1.42-1.48 (m, 1H), 1.28-1.37 (m, 1H), 0.82 (t, 3H). |
| 84 | | | 13.12 (s, 1H), 8.54 (d, 1H), 8.44 (d, 1H), 7.74 (d, 1H), 7.26 (q, 1H), 7.23 (br, 1H), 6.71 (m, 1H), 4.66 (d, 1H), 3.90 (m, 2H), 1.58-1.69 (m, 5H), 1.54-1.55 (m, 1H), 1.23-1.31 (m, 3H), 0.98 (m, 1H). |
| 85 | | | 13.93 (s, 1H), 8.52 (d, 1H), 8.50 (d, 1H), 7.83 (d, 2H), 7.26 (m, 8H), 7.11 (s, 1H), 6.66 (d, 1H), 5.56 (s, 1H), 2.95 (m, 1H), (m, 1H), 1.90 (m, 1H). |
| 86 | | | 13.88 (s, 1H), 8.53 (d, 1H), 8.43 (d, 1H), 7.74 (d, 1H), 7.29 (s, 2H), 7.25 (m, 1H), 7.11 (s, 3H), 6.96 (s, 2H), 6.62 (s, 1H), 4.71 (s, 1H), 3.93 (s, 1H), 3.45 (m, 2H), 3.15 (s, 1H), 1.68 (m, 1H), 1.45 (m, 1H), 0.90 (m, 3H). |

In general, compounds of the invention, including compounds in Table 1, are effective for the inhibition of PKCtheta. Selectivity for inhibition of PKCtheta by the compounds of the invention was tested and the results are shown in the following Example. The data obtained shows values for PKCtheta isoform selectivity by showing Ki potencies for PKCtheta, PKCdelta and PKCalpha.

Example 4

PKC Theta

An assay buffer solution was prepared which consisted of 100 mM HEPES (pH 7.5), 10 mM $MgCl_2$, 25 mM NaCl, 0.1 mM EDTA and 0.01% Brij. An enzyme buffer containing reagents to final assay concentrations of 0.00001% Triton X-100, 200 µg/mL Phosphatidylserine, 20 µg/mL Diacylglycerol, 360 µM NADH, 3 mM phosphoenolpyruvate, 70 µg/mL pyruvate kinase, 24 µg/mL lactate dehydrogenase, 2 mM DTT, 100 µM substrate peptide (ERMRPRKRQGSVRRRV (SEQ ID NO: 1)) and 18 nM PKC theta kinase was prepared in assay buffer. To 60 µL of this enzyme buffer, in a 384 well plate, was added 2 µL of VRT stock solution in DMSO. The mixture was allowed to equilibrate for 10 mins at 30° C. The enzyme reaction was initiated by the addition of 5 µL stock ATP solution prepared in assay buffer to a final assay concentration of 240 µM. Initial rate data was determined from the rate of change of absorbance at 340 nM (corresponding to stoichiometric consumption of NADH) using a Molecular Devices Spectramax plate reader (Sunnyvale, Calif.) over 15 mins at 30° C. For each Ki determination 12 data points covering the VRT concentration range of 0-20 µM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.). Ki values are represented as A<0.05 µM, B<0.5 µM, B*>0.7 µM, C<2.8 µM, C*>1.25 µM, D*>µM, 2 D>2.8 µM.
A compounds are: 1, 9, 18, 36, 61, 67 and 68.
B compounds are: 2, 3, 4, 6, 10, 11, 12, 13, 14, 16, 19, 22, 24, 25, 30, 33, 37, 38, 44, 47, 65, 70, 75, and 79.
B* compounds are: 7, 8, 15, 17, 20, 21, 26, 27, 28, 29, 31, 32, 34, 35, 39, 41, 42, 43, 45, 46, 48, 49, 50, 51, 52, 53, 54, 55, 56, 57, 58, 59, 60, 62, 63, 64, 66, 69, 71, 72, 73, 74, 76, 77, 78, 80, 81, 82, 83, 84, 85, and 86.
C compounds are: 5, 23, and 40.
In general, compounds of the invention, including compounds in Table 1, are effective for the inhibition of PKCtheta.

PKC Delta

An assay buffer solution was prepared which consisted of 100 mM HEPES (pH 7.5), 10 mM $MgCl_2$, 25 mM NaCl, 0.1 mM EDTA and 0.01% Brij. An enzyme buffer containing reagents to final assay concentrations of 0.002% Triton X-100, 200 µg/mL Phosphatidylserine, 20 µg/mL Diacylglycerol, 360 µM NADH, 3 mM phosphoenolpyruvate, 70 µg/mL pyruvate kinase, 24 µg/mL lactate dehydrogenase, 2 mM DTT, 150 µM substrate peptide (ERMRPRKRQGSVRRRV SEQ ID NO. 2) and 46 nM PKC delta kinase was prepared in assay buffer. To 16 µL of this enzyme buffer, in a 384 well plate, was added 1 µL of VRT stock solution in DMSO. The mixture was allowed to equilibrate for 10 mins at 30° C. The enzyme reaction was initiated by the addition of 16 µL stock ATP solution prepared in assay buffer to a final assay concentration of 150 µM. Initial rate data was determined from the rate of change of absorbance at 340 nM (corresponding to stoichiometric consumption of NADH) using a Molecular Devices Spectramax plate reader (Sunnyvale, Calif.) over 15 mins at 30° C. For each Ki determination 12 data points covering the VRT concentration range of 0-20 µM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.).
A compounds are: 61.
B compounds are: 1, 3, 4, 9, 11, 12, 14, 16, 18, 22, 36, 67, and 68.
C compounds are 2, 5, 6, 10, 13, 19, 23 and 37.
C* compounds are: 24-35, 38-60, 62-66, and 69-86.
D* compounds are 7, 8, 15, 17, 20 and 21.

PKC Alpha

An assay buffer solution was prepared which consisted of 100 mM HEPES (pH 7.5), 10 mM $MgCl_2$, 25 mM NaCl, 0.1 mM EDTA, 100 µM $CaCl_2$ and 0.01% Brij. An enzyme buffer containing reagents to final assay concentrations of 0.002% Triton X-100, 100 µg/mL Phosphatidylserine, 20 µg/mL Diacylglycerol, 360 µM NADH, 3 mM phosphoenolpyruvate, 70 µg/mL pyruvate kinase, 24 µg/mL lactate dehydrogenase, 2 mM DTT, 150 µM substrate peptide (RRRRRKGSFKRKA (SEQ ID NO: 2)) and 4.5 nM PKC alpha kinase was prepared in assay buffer. To 16 µL of this enzyme buffer, in a 384 well plate, was added 1 µL of VRT stock solution in DMSO. The mixture was allowed to equilibrate for 10 mins at 30° C. The enzyme reaction was initiated by the addition of 16 µL stock ATP solution prepared in assay buffer to a final assay concentration of 130 µM. Initial rate data was determined from the rate of change of absorbance at 340 nM (corresponding to stoichiometric consumption of NADH) using a Molecular Devices Spectramax plate reader (Sunnyvale, Calif.) over 15 mins at 30° C. For each Ki determination 12 data points covering the VRT concentration range of 0-20 µM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.).
B compounds are: 3, 9, 18, 61, 67, and 68.
C compounds are: 1, 5, 6, 11, and 36.
C* compounds are: 2, 4, 7, 8, 10, 12, 13, 14, 15, 17, 19-35, 37-60, 62-66, 69-86.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:

1. A compound represented by a structural formula selected from the group consisting of:

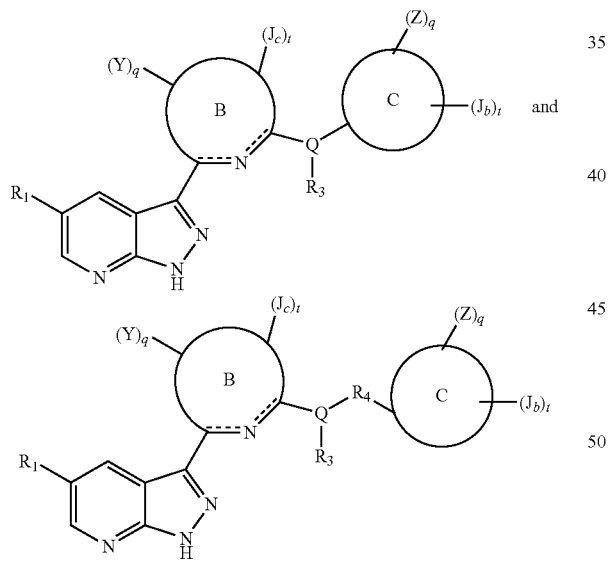

or a pharmaceutically acceptable salt thereof, wherein:
$R_1$ is —H, halogen or C1-C10 haloalkyl;
Q is —N—, —O—, or —S—;
ring B is a 6-membered monocyclic heteroaromatic ring optionally fused to an aromatic or non-aromatic ring; and ring B is optionally substituted with one Y and independently further optionally and independently substituted with one or more $J_c$;
Y is —Y1-Q1;
Y1 is absent, or C1-10 aliphatic, wherein up to three methylene units of Y1 are optionally and independently replaced with G' wherein G' is —O—, —C(O)—, —N(R')—, or —S(O)$_p$—; and Y1 is optionally and independently substituted with one or more $J_a$;
Q1 is absent, or a C3-8 membered saturated, partially unsaturated, or fully unsaturated monocyclic ring having 0-3 heteroatoms independently selected from nitrogen, oxygen, and sulfur; and Q1 is optionally and independently substituted with one or more $J_b$; wherein Y1 and Q1 are not both absent;
$R_3$ is absent, —H, or C1-C6 alkyl optionally and independently substituted with one or more $J_a$;
$R_4$ is a C1-10 aliphatic, wherein up to three methylene units of $R_4$ are optionally and independently replaced by G' wherein G' is —O—, —C(O)—, —N(R')—, or —S(O)$_p$—; and $R_4$ is optionally and independently substituted with one or more $J_a$;
ring C is a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur optionally and independently substituted with one Z or independently further optionally and independently substituted with one or more $J_b$;
Z is —Y2-Q2;
Y2 is absent, or C1-10 aliphatic, wherein up to three methylene units of Y2 are optionally and independently replaced with G' wherein G' is —O—, —C(O)—, —N(R')—, or —S(O)$_p$—; and Y2 is optionally and independently substituted with one or more $J_a$;
Q2 is absent, C3-8 membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur; and Q2 is optionally and independently substituted with one or more $J_c$; wherein Y2 and Q2 are not both absent;

each R' is independently —H, or C1-C6 alkyl optionally and independently substituted with one or more $J_a$;

each $J_a$ is independently halogen, —OR, —N(R)$_2$, —C(O)OR, —C(O)N(R)$_2$, —NRC(O)R, —NRC(O)OR, —CN, —NO$_2$, or oxo;

each $J_b$ is independently halogen, —OR, —N(R)$_2$, —C(O)OR, —C(O)N(R)$_2$, —NRC(O)R, —NRC(O)OR, —CN, —NO$_2$, oxo, or C1-C6 alkyl optionally and independently substituted with $J_a$;

each $J_c$ is independently halogen, —OR', —N(R')$_2$, —C(O)OR', —C(O)N(R')$_2$, —NR'C(O)R', —NR'C(O)OR', —CN, —NO$_2$, or C1-C10 aliphatic optionally and independently substituted with one or more $J_a$, or C3-C8 cycloaliphatic optionally and independently substituted with one or more $J_b$;

each $J_d$ is independently halogen, —CN, or —NO$_2$;

each $J_e$ is independently halogen, —CN, —NO$_2$, oxo, C1-10 aliphatic, wherein up to three methylene units are optionally and independently replaced with G' wherein G' is —O—, —C(O)—, —N(R')—, or —S(O)$_p$— and the aliphatic group is optionally and independently substituted with one or more $J_d$, or $J_e$ is C3-8 cycloaliphatic optionally and independently substituted with one ore more $J_b$;

each R is independently —H or C1-C6 alkyl;

each q is independently 0 or 1; and each t is independently 0, 1, or more.

2. The compound of claim 1 wherein:
ring B is pyridyl, pyrazinyl, pyrimidinyl, isoquinolyl, quinazolinyl, pyridopyridyl, pyridopyradazinyl, pyrrolopyridiyl, pyrazolopyridiyl, pyrolopyrimidinyl, or pyrrolopyrazinyl, wherein ring B is optionally substituted with one Y and independently further and optionally and independently substituted with one or more $J_c$.

3. The compound of claim 2 wherein:
ring B is pyridyl, pyrazinyl, pyrimidinyl, isoquinolyl, pyrrolopyridiyl, pyrazolopyridiyl, pyrolopyrimidinyl, or pyrrolopyrazinyl, wherein ring B is optionally substituted with one Y and independently further and optionally and independently substituted with one or more $J_c$.

4. The compound of claim 3 wherein:
ring B is pyridyl optionally substituted with one Y and independently further and optionally and independently substituted with one or more $J_c$.

5. The compound of claim 3 wherein:
ring B is pyrazinyl optionally substituted with one Y and independently further and optionally and independently substituted with one or more $J_c$.

6. The compound of claim 4 wherein:
ring C is selected from the group consisting of cyclopropyl, cyclopentyl, cyclobutyl, cyclohexyl, cyclohexenyl, phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, indolyl, indazolyl, benzimidazolyl, quinolyl, quinoxalyl, indolinyl, oxazolidinyl, isoxazolidinyl, thiazolidinyl, isothiazolidinyl, oxazocanyl, oxazepanyl, azabicyclopentyl, azabicyclohexyl, azabicycloheptyl, azabicyclooctyl, azabicyclononyl, azabicyclodecyl, diazabicyclohexyl, diazabicycloheptyl, azetidinyl, isoindolinyl, isoindolyl, dihydroindazolyl, dihydrobenzimidazolyl, morpholinyl, tetrahydropyridyl, dihydropyridyl, tetrahydropyrazinyl, dihydropyrazinyl, tetrahydropyrimidinyl, dihydropyrimidinyl, dihydropyrrolyl, dihydropyrazolyl, dihydroimidazolyl, octahydropyrrolopyrazyl, octahydropyrrolopyridyl, octahydropyridopyrazyl, octahydropyridopyridyl, diazabicyclooctyl, diazabicyclononyl, diazabicyclodecyl, thiazepanyl, and thiazocanyl wherein each ring is independently optionally and independently substituted with one Z and independently further and optionally substituted with one or more $J_b$.

7. The compound of claim 4 wherein
ring C is selected from the group consisting of cyclohexyl, diazabicyclooctyl, phenyl, pyridyl, pyrazinyl, pyrimidinyl, pyrrolyl, imidazolyl, pyrazolyl, oxazalolyl, oxadiazolyl, thiazolyl, azetidinyl, morpholinyl, azepanyl, diazabicycloheptyl, diazabicyclooctyl, indolyl, tetrahydropyridyl, dihydropyridyl, octahydropyrrolopyrazyl, octahydropyrrolopyridyl, octahydropyridopyrazyl, octahydropyridopyridyl, thiadiazolyl, piperidinyl, piperazinyl, pyrrolidinyl, diazepanyl, and oxazepanyl wherein each ring is independently optionally and independently substituted with one Z and independently further and optionally substituted with one or more $J_b$.

8. The compound of claim 4 wherein
ring C is selected from the group consisting of cyclohexyl, 3,8-diazabicyclo[3.2.1.]octane, phenyl, pyridyl, piperidinyl, piperazinyl, diazepanyl, pyrrolidinyl, pyrrolyl, pyrrazolyl, azetidinyl, morpholinyl, azepanyl, 2,5 diazabicycloheptyl, diazabicyclooctyl, indolyl, tetrahydropyridyl, octahydro-1H-pyrrolo[2,3-b]pyrazyl, octahydropyrrolo[1,2-a]pyrazyl, and oxazepanyl wherein each ring is independently optionally and independently substituted with one Z and independently further and optionally substituted with one or more $J_b$.

9. The compound of claim 4 wherein
ring C is selected from the group consisting of cyclohexyl, phenyl, piperidinyl, piperazinyl, diazapanyl, pyrrolidinyl, azetidinyl, and azepanyl, wherein each ring is independently optionally and independently substituted with one Z and independently further and optionally substituted with one or more $J_b$.

10. The compound of claim 5 wherein ring C is represented a structural formula selected from the group consisting of:

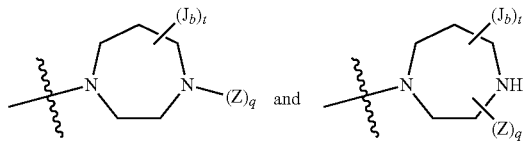

q is 0 or 1; and
t is 0, 1 or more.

11. The compound of claim 5 wherein ring C is represented by a structural formula selected from the group consisting of:

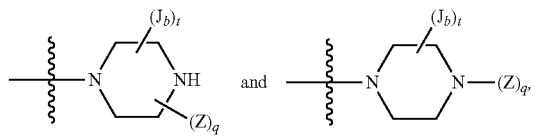

q is 0 or 1; and
t is 0, or 1-4.

12. The compound of claim 11 wherein ring C is represented by a structural formula represented by:

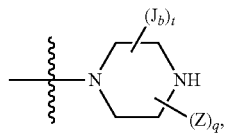

q is 0 or 1; and
t is 0, or 1-4.

13. The compound of claim 4 wherein ring C is represented by a structural formula selected from the group consisting of:

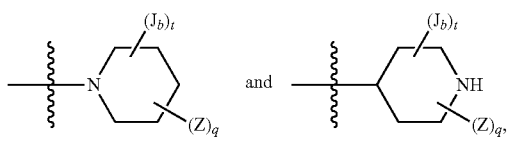

q is 0 or 1; and
t is 0, or 1-4.

14. The compound of claim 13 wherein ring C is represented by a structural formula represented by:

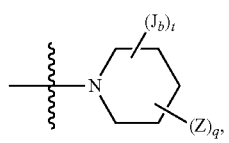

q is 0 or 1; and
t is 0, or 1-4.

15. The compound of claim 13 wherein ring C is represented by a structural formula represented by:

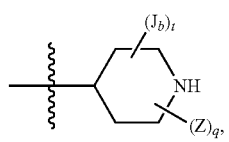

q is 0 or 1; and
t is 0, or 1-4.

16. The compound of claim 15 wherein:
$R_4$ is a C1-10 aliphatic, wherein up to three methylene units of $R_4$ are optionally and independently replaced by G' wherein G' is —O—, —C(O)—, —N(R')—, or —S(O)$_p$—; and $R_4$ is optionally and independently substituted with one or more $J_a$.

17. The compound of claim 16 wherein:
$R_4$ is a C2-10 aliphatic, wherein up to three methylene units of $R_4$ are optionally and independently replaced by G' wherein G' is —O—, or —N(R')—; and $R_4$ is optionally and independently substituted with one or more $J_a$.

18. The compound of claim 1, wherein the compound represented by a structural formula selected from the group consisting of:

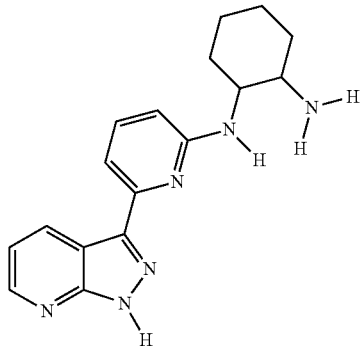
3

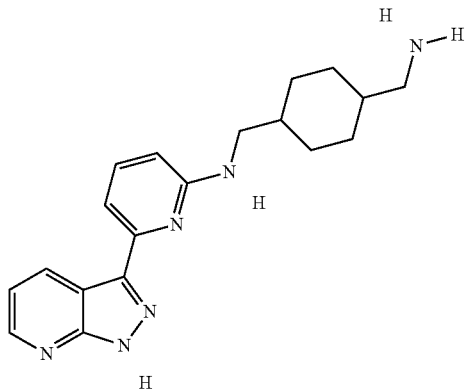
4

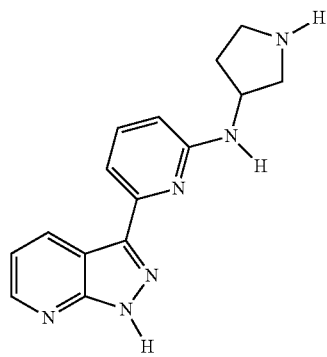
6

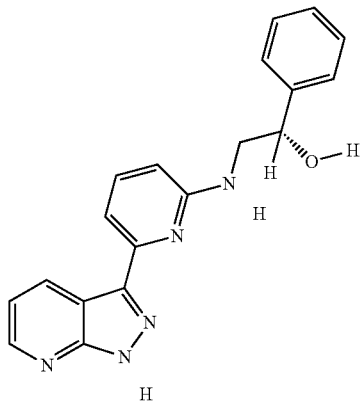
7

-continued
9
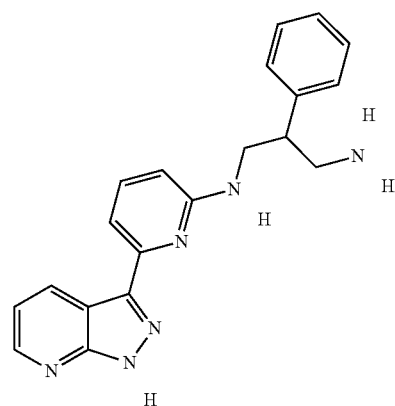
11
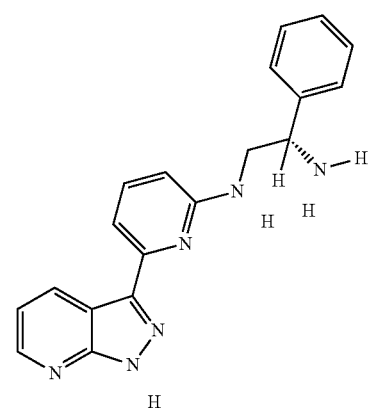
12
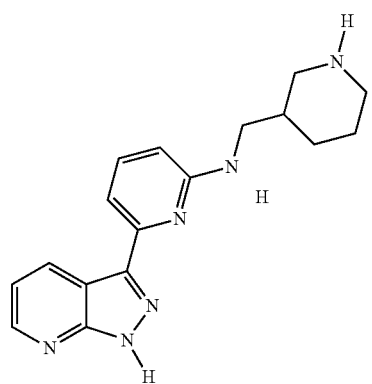
13
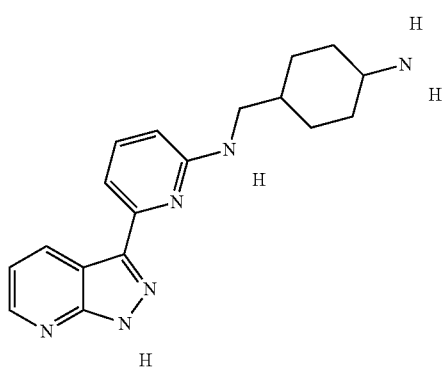
-continued
14
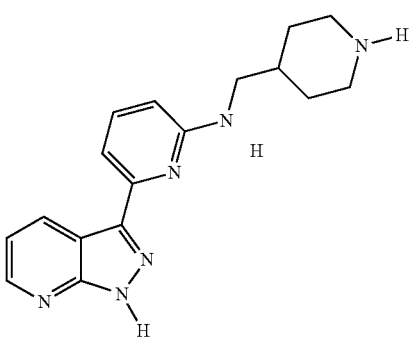
18
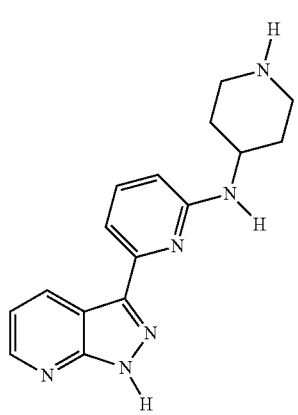
19
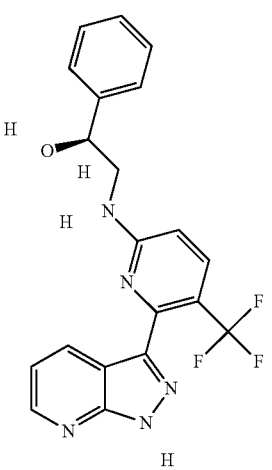
20
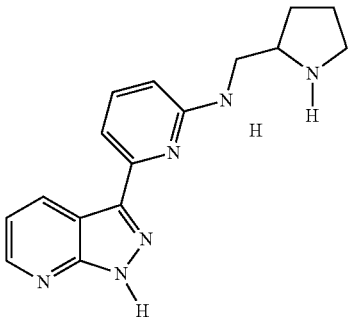

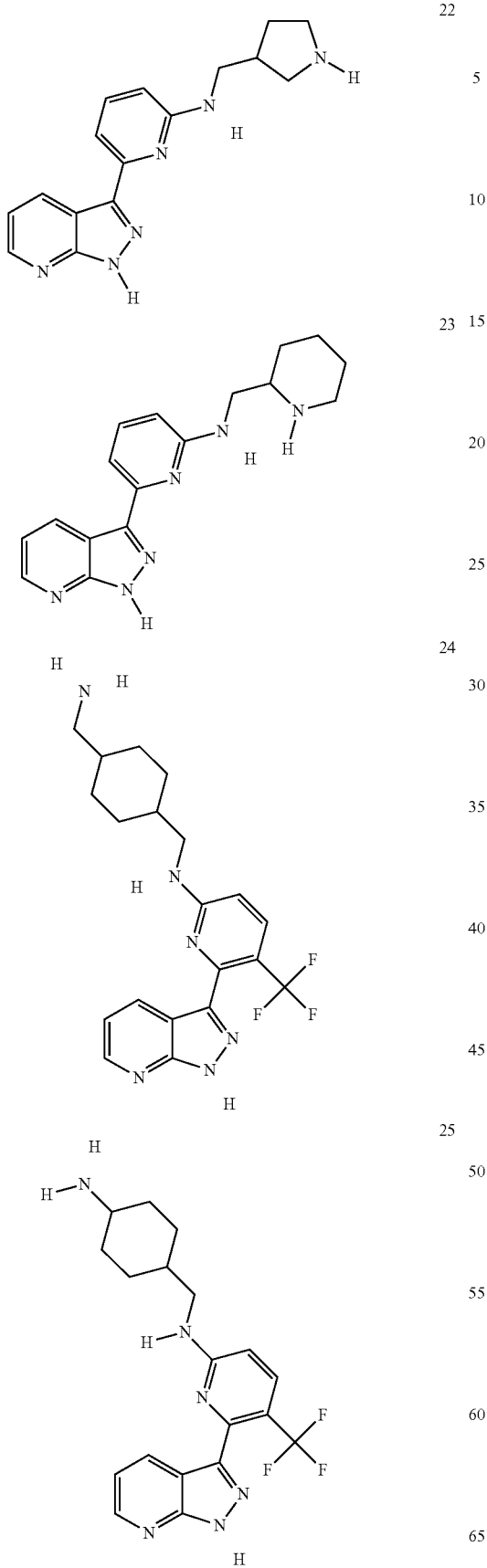
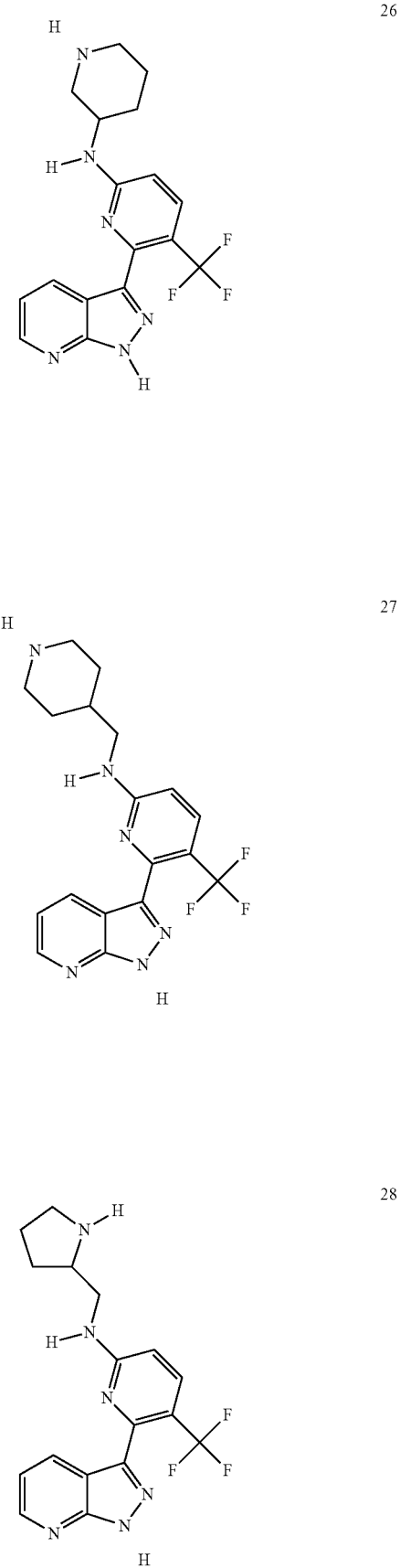

29
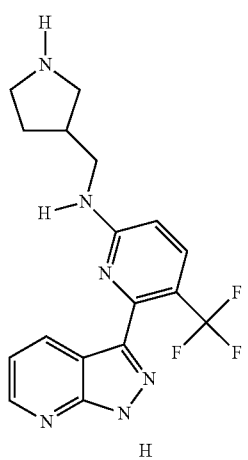
30
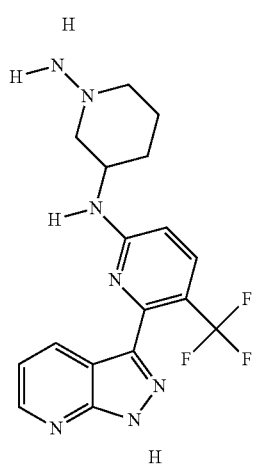
31
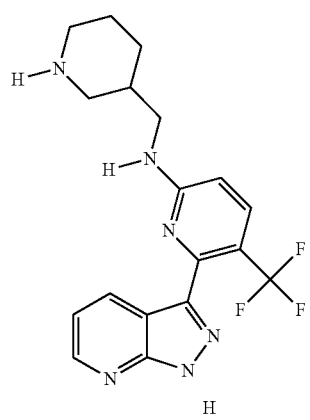
32
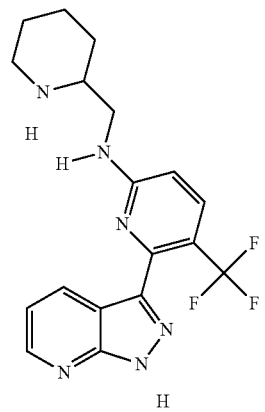
34
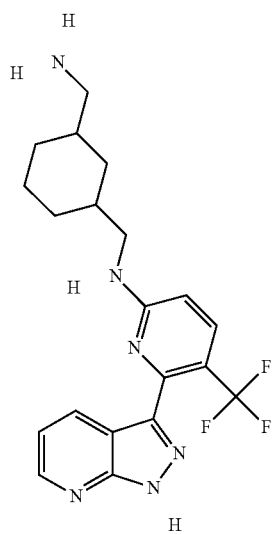
35
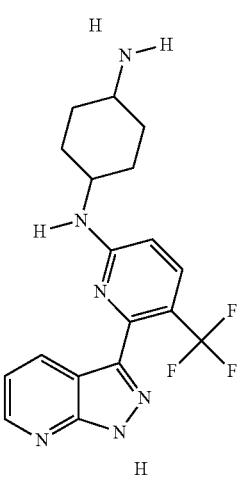

36
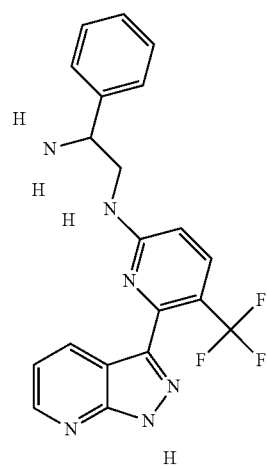
37
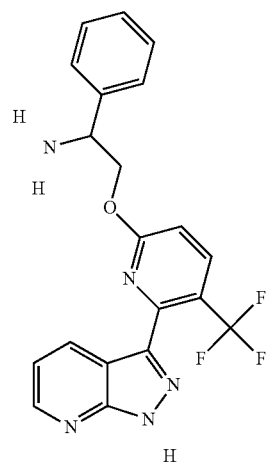
41
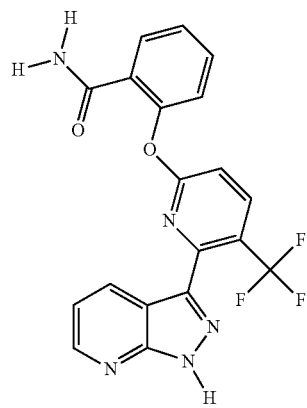
43
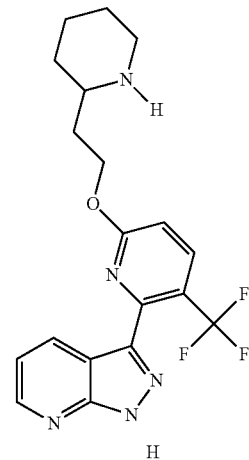
46
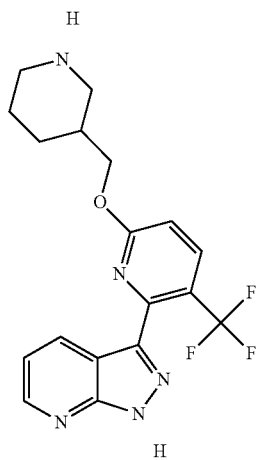
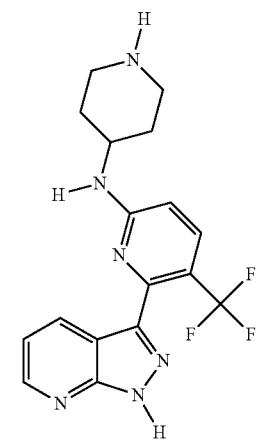

| 93 -continued | | 94 -continued | |
|---|---|---|---|
| 47 | 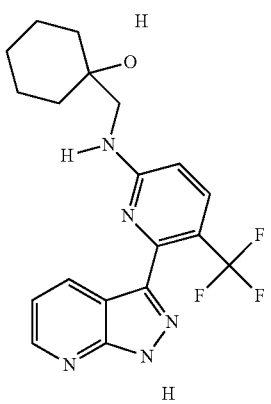 | 50 | 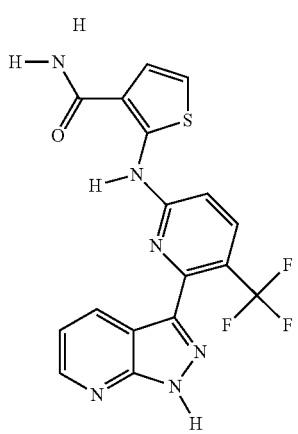 |
| 48 | | 51 | 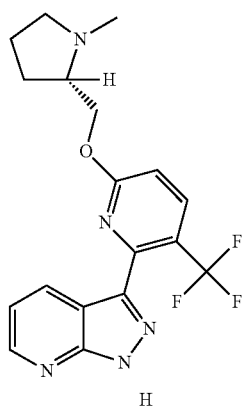 |
| 49 | | | 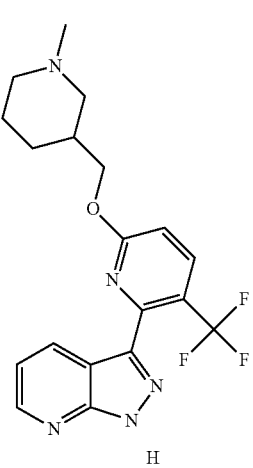 |

| 95 -continued | | 96 -continued | |
|---|---|---|---|
| | 56 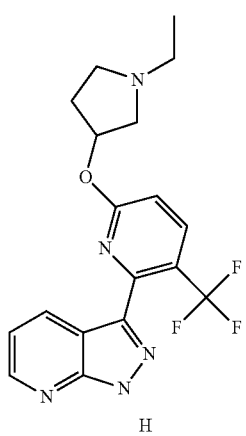 | 61 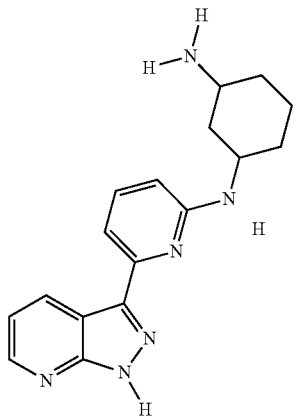 | |
| | 59 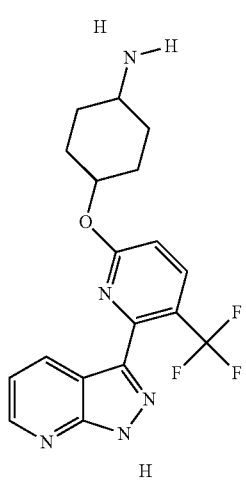 | 63 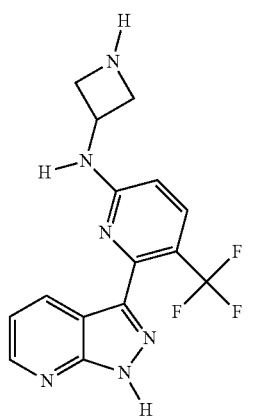 | |
| | | 64 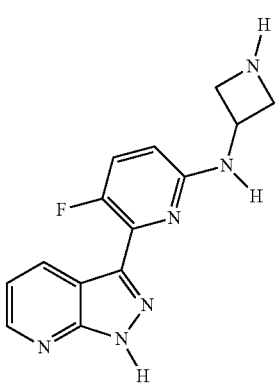 | |
| | 60 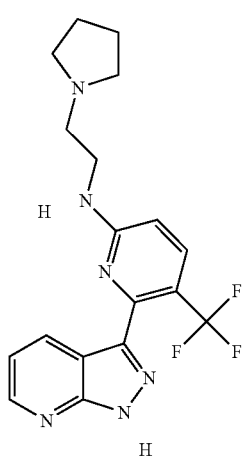 | 65 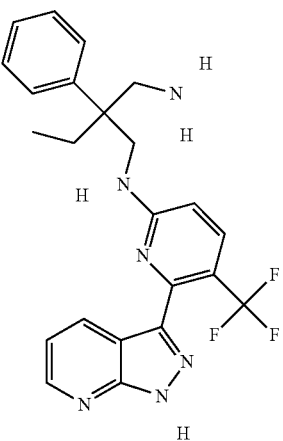 | |

97
-continued
66
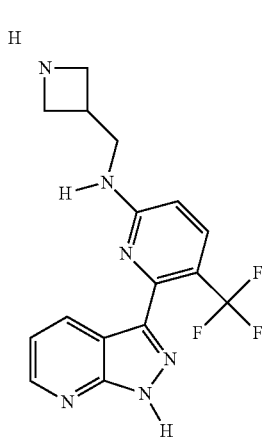
67
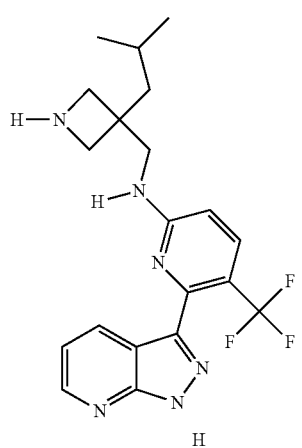
68
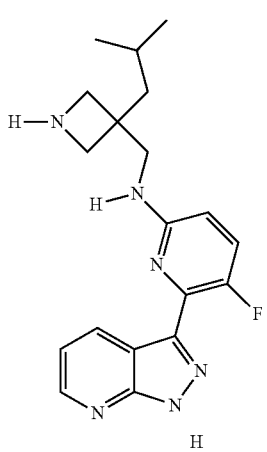
98
-continued
69
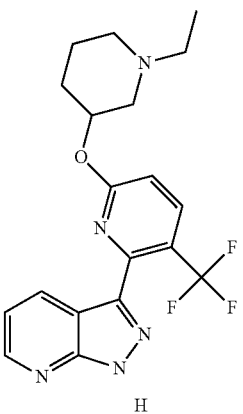
70
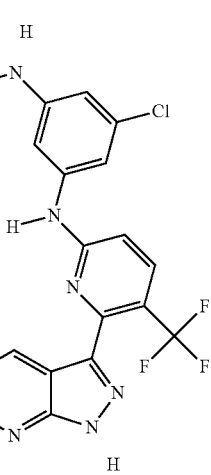
71
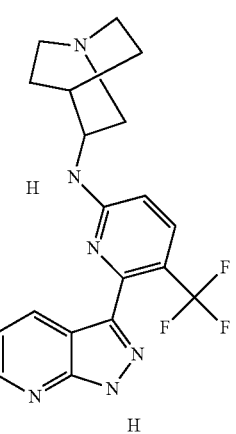

US 9,137,973 B2
74
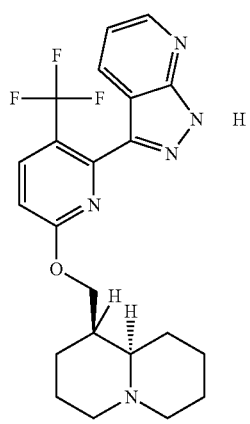
77
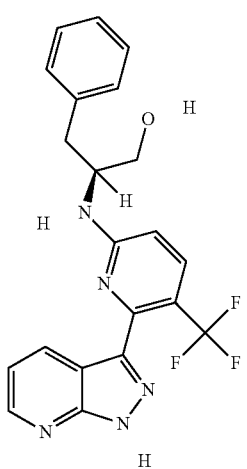
78
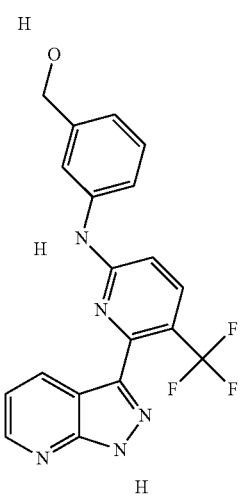
79
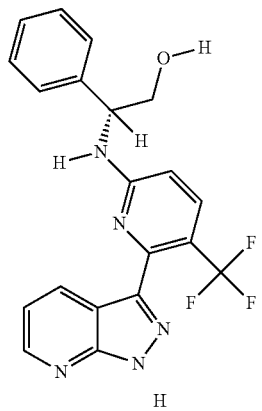
81
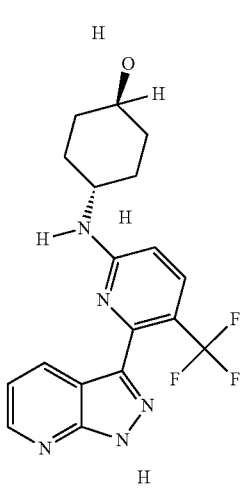
84
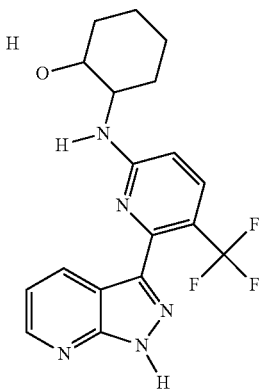

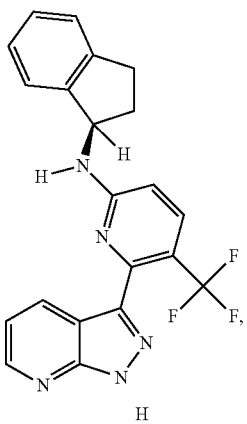

or a pharmaceutically acceptable salt thereof.

19. A composition comprising the compound of claim 1 or a pharmaceutically acceptable salt thereof, and a pharmaceutically acceptable carrier, adjuvant, or vehicle.

20. A method of treating a protein kinase c theta mediated condition in a subject, wherein the condition is selected from the group consisting of psoriasis or transplant rejection, comprising administering to the subject an effective amount of a compound or pharmaceutically acceptable salt thereof or composition of any one of claims 1-4, 6, 13 and 15-19.

* * * * *

SEQUENCE LISTING

<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Arg Met Arg Pro Arg Lys Arg Gln Gly Ser Val Arg Arg Arg Val
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Arg Arg Arg Lys Gly Ser Phe Lys Arg Lys Ala
1               5                   10